US012080425B1

(12) United States Patent
Corts et al.

(10) Patent No.: US 12,080,425 B1
(45) Date of Patent: Sep. 3, 2024

(54) EVENT TRIGGERING UTILIZING SEGMENT ASSIGNMENTS

(71) Applicant: C/HCA, Inc., Nashville, TN (US)

(72) Inventors: Andy Corts, Nashville, TN (US); Troy Gifford, Brentwood, TN (US)

(73) Assignee: C/HCA, Inc., Nashville, TN (US)

( * ) Notice: Subject to any disclaimer, the term of this patent is extended or adjusted under 35 U.S.C. 154(b) by 370 days.

(21) Appl. No.: 17/159,700

(22) Filed: Jan. 27, 2021

Related U.S. Application Data

(60) Provisional application No. 62/966,727, filed on Jan. 28, 2020.

(51) Int. Cl.
*G16H 50/20* (2018.01)
*G16H 10/60* (2018.01)
*G16H 50/30* (2018.01)

(52) U.S. Cl.
CPC ............ *G16H 50/20* (2018.01); *G16H 10/60* (2018.01); *G16H 50/30* (2018.01)

(58) Field of Classification Search
CPC ......... G16H 50/20; G16H 10/60; G16H 50/30
See application file for complete search history.

(56) References Cited

U.S. PATENT DOCUMENTS

| | | |
|---|---|---|
| 9,880,881 B1 | 1/2018 | Perez et al. |
| 10,303,519 B1 | 5/2019 | Perez et al. |
| 10,652,164 B2 | 5/2020 | Garcia et al. |
| 10,817,342 B1 | 10/2020 | Perez et al. |
| 10,847,261 B1 * | 11/2020 | Neumann .............. G16H 70/60 |
| 11,201,835 B1 | 12/2021 | Roberts et al. |
| 11,283,690 B1 | 3/2022 | Mosier et al. |
| 11,283,726 B1 | 3/2022 | Houston et al. |
| 11,381,506 B1 | 7/2022 | Jindal et al. |
| 11,422,830 B1 | 8/2022 | Hefley |
| 11,595,320 B1 | 2/2023 | Gregg et al. |
| 2008/0155386 A1 | 6/2008 | Jensen |

(Continued)

FOREIGN PATENT DOCUMENTS

CN 106999107 A * 8/2017 .......... A61B 5/0064

OTHER PUBLICATIONS

Nkweteyim, Denis Lemongew; A collaborative filtering approach to predict web pages of interest from navigation patterns of past users within an academic website; University of Pittsburgh. ProQuest Dissertations Publishing, 2005. 3192994. (Year: 2005).*

Primary Examiner — Hiep V Nguyen
(74) Attorney, Agent, or Firm — Polsinelli PC; Kory D. Christensen

(57) ABSTRACT

Techniques are disclosed for assigning a user to a particular user navigation program among a plurality of user navigation programs. The techniques include receiving user data associated with a user record of a user. The techniques further include inputting the user data into a segmentation model of a user navigation system to classify a user within a segment, whereby the segmentation model outputs a score that is determined to be in accordance with a classification threshold. The user navigation system further detects an occurrence of a trigger based in part on the user classification within the segment, and then prioritizes the user among other users based on the detected occurrence of the trigger. The user navigation system then assigns the user to a particular user navigation program based at least in part on the determined priority of the user.

20 Claims, 20 Drawing Sheets

(56) References Cited

U.S. PATENT DOCUMENTS

| | | | |
|---|---|---|---|
| 2010/0332583 A1* | 12/2010 | Szabo | G06F 16/2457 |
| | | | 709/217 |
| 2012/0065987 A1* | 3/2012 | Farooq | G16H 50/70 |
| | | | 705/2 |
| 2016/0094410 A1 | 3/2016 | Anwar et al. | |
| 2017/0310605 A1 | 10/2017 | Garcia et al. | |
| 2020/0296053 A1 | 9/2020 | Garcia et al. | |
| 2022/0385581 A1 | 12/2022 | Delos Reyes et al. | |

* cited by examiner

```
                                              ┌─ 1700
```

RECEIVE USER DATA ASSOCIATED WITH A USER RECORD OF A USER, THE USER RECORD BEING ONE OF A PLURALITY OF USER RECORDS OF USERS MAINTAINED BY A SERVICE MANAGEMENT SYSTEM OF A SERVICE ORGANIZATION 1702

↓

DETERMINE AN ASSESSMENT CORRESPONDING TO AT LEAST ONE OF: (1) A SEGMENT OF A PLURALITY OF SEGMENTS IN WHICH THE USER IS CLASSIFIED, THE SEGMENT DETERMINED BASED AT LEAST IN PART ON AN OCCURRENCE OF A TRIGGER, OR (2) AT LEAST ONE USER NAVIGATION PROGRAM FOR WHICH THE USER QUALIFIES OR IS ALREADY ASSIGNED 1704

↓

PROVIDE THE ASSESSMENT TO A USER DEVICE OF A USER NAVIGATION COORDINATOR FOR SUBSEQUENT PRESENTATION ON A DASHBOARD OF THE USER DEVICE, THE ASSESSMENT BEING ONE OF A PLURALITY OF ASSESSMENTS RESPECTIVELY DETERMINED FOR EACH OF THE PLURALITY OF USERS AND PROVIDED TO THE USER DEVICE FOR PRESENTATION 1706

┌─────────────────────────────────────────────────────────────────┐
│ RECEIVE AN INDICATION THAT A USER OF A SERVICE FACILITY IS      │
│ ASSIGNED TO A FIRST USER NAVIGATION PROGRAM AND A SECOND USER   │
│ NAVIGATION PROGRAM OF A PLURALITY OF USER NAVIGATION PROGRAMS   │
│ 1802                                                            │
└─────────────────────────────────────────────────────────────────┘
                              ↓
┌─────────────────────────────────────────────────────────────────┐
│ TRANSMIT A FIRST MESSAGE TO A FIRST USER DEVICE OF A FIRST USER │
│ NAVIGATOR OF THE FIRST USER NAVIGATION PROGRAM 1804             │
└─────────────────────────────────────────────────────────────────┘
                              ↓
┌─────────────────────────────────────────────────────────────────┐
│ RECEIVE A FEEDBACK MESSAGE INCLUDING UPDATED USER DATA          │
│ ASSOCIATED WITH AN UPDATED CONDITION OR AN UPDATED TREATMENT    │
│ STATUS OF THE USER 1806                                         │
└─────────────────────────────────────────────────────────────────┘
                              ↓
┌─────────────────────────────────────────────────────────────────┐
│ GENERATE A SECOND MESSAGE BASED AT LEAST IN PART ON THE         │
│ RECEIVED FEEDBACK MESSAGE 1808                                  │
└─────────────────────────────────────────────────────────────────┘
                              ↓
┌─────────────────────────────────────────────────────────────────┐
│ TRANSMIT THE SECOND MESSAGE TO A SECOND USER DEVICE OF A SECOND │
│ USER NAVIGATOR OF THE SECOND USER NAVIGATION PROGRAM FOR        │
│ PRESENTATION ON THE SECOND USER DEVICE 1810                     │
└─────────────────────────────────────────────────────────────────┘
```

FIG. 18

EVENT TRIGGERING UTILIZING SEGMENT ASSIGNMENTS

CROSS-REFERENCE TO RELATED APPLICATION

This application claims the benefit of and priority to U.S. Provisional Application No. 62/966,727, filed Jan. 28, 2020, which is hereby incorporated by reference in its entirety for all purposes.

BACKGROUND

The amount of data generated each day continues to grow. In some environments, some of this data may be stored, while a majority of it may be evaluated and abandoned or ignored. Users and computing devices are beginning to rely more and on this data to make decisions. This may be especially true when the data is introduced as part of an operational flow. However, the time required to sort through stored data can create inefficiencies and the fact that other data may typically be ignored or abandoned may create undesirable outcomes.

SUMMARY

Exemplary embodiments of the disclosure provide systems and methods for assigning a user to user navigation program for receiving service based in part on classifying the user into one or more segments and then determining that a trigger event occurs based on the user classification. According to an aspect of the disclosure, a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computer-implemented method for assigning a user to a user navigation program. The computer-implemented method also includes receiving, by a user navigation system, user data associated with a user record of a user of a service facility, the user record being one of a plurality of user records of users maintained by a service management system of a service organization, the service facility being one of a plurality of service facilities affiliated with the service organization. The method also includes inputting, by the user navigation system, the user data into a segmentation model of the user navigation system, the user data including at least one of structured user data or unstructured user data, and the user data associated with at least one of a present condition or a present service status of the user. The method also includes determining, by the segmentation model, a score for the user, the score corresponding to a level of confidence that a classification of the user corresponds to a segment associated with the present condition or the present service status of the user, the segment being one of a plurality of candidate segments. The method also includes classifying, by the user navigation system and using the score, the user within the segment in accordance with a classification threshold, the classification threshold associated with a level of confidence of the score. The method also includes detecting, by the user navigation system, an occurrence of a trigger of a plurality of triggers based at least in part on the classification of the user within the segment. The method also includes determining, by the user navigation system, a priority of the user among the plurality of users based at least in part on the occurrence of the trigger. The method also includes assigning, by the user navigation system, the user to a particular user navigation program among a plurality of user navigation programs based at least in part on the determined priority of the user. Other embodiments of this aspect include corresponding computer systems, apparatus, and computer programs recorded on one or more computer storage devices, each configured to perform the actions of the methods.

Other objects, advantages, and novel features of the present disclosure will become apparent from the following detailed description of the disclosure when considered in conjunction with the accompanying drawings.

BRIEF DESCRIPTION OF THE DRAWINGS

Various examples in accordance with the present disclosure will be described with reference to the drawings, in which:

FIG. 17 illustrates an example process for providing user assessment data to a GUI for coordinating assignments of users to user navigation programs, according to at least one example;

FIG. 18 illustrates an example process for transmitting a message to a user device of a user navigator based on receiving updated user data, according to at least one example;

DETAILED DESCRIPTION

Figure 1:
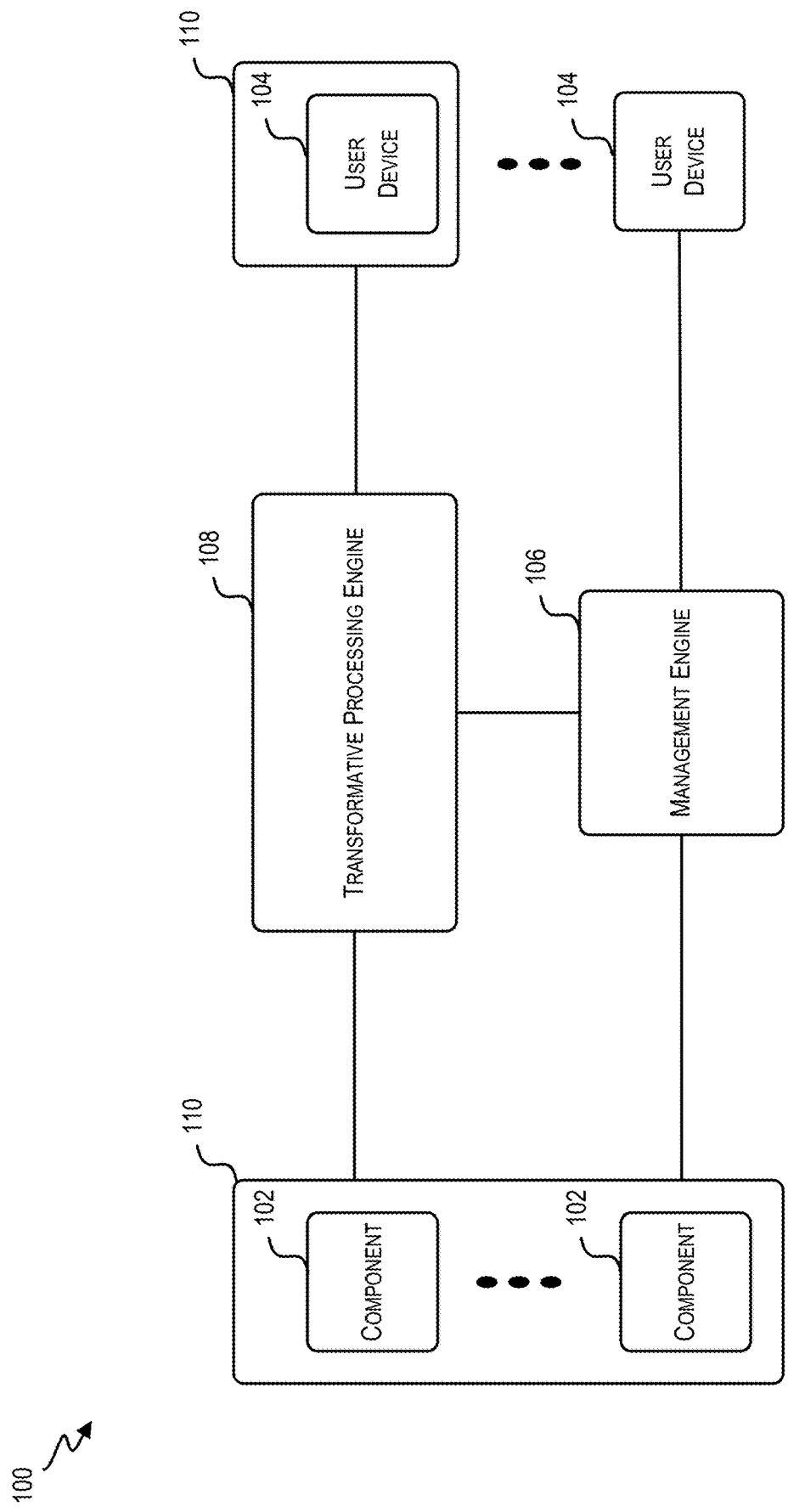
FIG. 1 is an example block diagram illustrating an interaction system in which techniques relating to assigning a user to a user navigation program may be implemented, according to at least one example.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In one example, a user navigation (UN) system provides support for a user service provider (USP) that is providing service for users within a service organization (which may also be known as a "service system" or "enterprise"). The enterprise may include a plurality of divisions, and each division may include one or more service facilities. For example, the enterprise may geographically organized within the United States (U.S.), whereby there is a division per state, county, or the like. Each division may include one or more service facilities, for example, including clinics, labs, nursing facilities, rehabilitation centers, home health agencies, and any other user service center where a user may receive service by a service provider. The service organization may maintain a service management computer system, which coordinates user service and records across the service organization (e.g., via one or multiple Electronic Medical Record (EMR) system(s)). In some examples, the service management system may further include (or be associated with) the UN system. In some cases, the USP may be an executive or administrator of the enterprise (e.g., at an enterprise level, division level, or service facility level). In some cases, the USP may be a service provider such as a clinical nurse consultant (CNC), a user navigator, a user navigation coordinator, a floor nurse, a specialty nurse, a physician, or other service professional.

Typically, a service facility will admit a user for one or more conditions. For example, a user may be admitted due to an observed lump in a part of the breast. After performing diagnostic tests, a USP may diagnose the user with stage one breast cancer. To facilitate improved user outcomes over the long-term, the service facility may assign one or more user navigators to help the user navigate the cancer service and recovery process (or "cancer journey"). In this example, the user navigator may assist the user with various tasks related to the cancer journey. For example, the user navigator may provide counseling to the user to make them aware of cancer service options available, help to facilitate and/or coordinate scheduling appointments, remind the user when appointments are upcoming, function as a liaison between the user and their physician (and/or other USPs involved in the cancer service process), educate the user regarding affordable payment options in view of the user's particular health insurance plan, coordinate ordering prescriptions to be filled with the user's preferred pharmacist on behalf of the user, etc. In some examples, by assisting the user with various tasks, the user navigator may enable a "high-touch" level of service to be provided to the user. This high-touch service model may involve using a high frequency of encounters with the user to deliver preventative services that lead to positive outcomes (e.g., cancer remission). In some examples, the user navigation process may be provided to a user in any suitable way (e.g., in-person, via the Internet, phone calls, etc.). A virtual navigation (VN) process (which, in some examples, may also enable a high-touch service model) may refer to a user navigation process that is provided to a user remotely (e.g., via the Internet), which may assist USPs in delivering service to users who are in remote geographic locations. To help coordinate the user navigation process among service facilities of the enterprise, improve user outcomes, and improve efficiencies of providing user service, the UN system may provide support to one or more USPs (e.g., user navigators) in several different forms and using various methods.

In some examples, the UN system may assign a user to a user navigation program. A service facility may desire to determine, as early as possible, the condition of the user and what type of service the user will likely need. By determining this information early in a user's service journey, the service facility may be able to more efficiently and accurately determine an appropriate user navigation program and pair a user with an appropriate user navigator, which in turn may increase the probability of a longer-term successful outcome. In one example, the UN system may receive user data associated with the user (e.g., derived from the user's service record). This user data may be received by the UN system and processed in substantially real-time (e.g., within 5 seconds, 10 seconds, 30 seconds, 1 minute, or 5 minutes of entry). The user data may include structured data (e.g., blood lab results) and/or unstructured data (e.g., clinician notes of a pathology report), as described further herein. The UN system may input the user data into a prediction model (e.g., a segmentation model) of the UN system. In some examples, the segmentation model may utilize one or more machine learning models. The segmentation model may output one or more scores (e.g., probability scores) that respectively correspond to a level of confidence of a particular classification (e.g., or "segmentation") of the user. For example, the UN system may maintain a plurality of candidate segments (or categories). In some examples, a segment may be associated with the present condition or the present service status of the user. For example, in the case where a segment refers to a present condition, a segment may defined broadly (e.g., cancer) or more narrowly (e.g., stage 1 breast cancer). In another example, where the segment may refer to the present service status of the user, the segment may indicate, for example, if the user was recently discharged, how long the user was admitted to the service facility, a stage of service (e.g., third round of chemotherapy), or other service-related information. A user may be classified within more than one segment. Also, in some cases, a given segment may represent more than one variable (e.g., both a present condition and a present service status). Upon the segmentation model outputting a score, the UN system may classify the user within a given segment based in part on the score being in accordance with a classification threshold. For example, the classification threshold may correspond to a numerical value (e.g., 0.80 or 80%) that is used to indicate a high degree of confidence in a score for a particular classification. Thus, a score of 0.85 may be in accordance with (e.g., greater than or equal to) the classification threshold, and thus, the user may be classified within the given segment with high confidence. Other suitable classification thresholds may be used (e.g., low confidence (e.g., <=0.5, moderate confidence (e.g., between 0.5-0.79), etc.). For example, the segmentation model may output a score of 0.95, corresponding to a level of confidence that the user has cancer. The segmentation model may further output a score of 0.75, corresponding to a level of confidence that the user has breast cancer. Using the example above, the UN system may classify the user within a "cancer" segment with high confidence, and a "breast cancer" segment (or sub-segment) with moderate confidence. In some examples, the classification threshold and/or segment may be associated with a level of severity. It should be understood that a given classification threshold may be represented in any suitable format (e.g., including one or more numerical or string values, percentages, sub-thresholds, etc.). Once the user is classified in one or more segments, the UN system may then detect an occurrence of one or more triggers based on the classifications. A trigger may correspond to a rule (or mechanism) that is activated when one or more conditions are met. For example, using the example above, a trigger may correspond to a rule that activates upon detecting a user classified with a particular type of cancer (e.g., breast cancer, stage 1 breast cancer, stage 2 breast cancer, etc.). In some cases, a trigger may be associated with a level of confidence in the particular classification (e.g., high, moderate, or low confidence). Based on the occurrence of one or more triggers, the UN system may determine a priority of the user among a plurality of users of the service facility. In some examples, the priority of the user may indicate the user's position within a queue of users who are candidates for being assigned to a user navigation program (e.g., which may have a finite number of user navigators available for pairing with users). Then, based in part on the priority of the user, the UN system may assign the user to a particular user navigation program (e.g., a breast cancer navigation program) among a plurality of candidate user navigation programs (e.g., breast cancer navigation program, colon cancer navigation program, lung cancer navigation program, complex gastroenterology (GI) navigation program, etc.). The assignment may also involve pairing the user with a particular user navigator and/or determining one or more interactions between the user and the assigned user navigator over the course of the user's journey within the program.

In another example, the UN system may determine further service for a user that is already assigned to a user navigation program. For example, the UN system may receive an indication that a user has already been assigned to a first user navigation program among a plurality of user navigation programs (e.g., a breast cancer navigation program), for example, due to a previous occurrence of a first trigger. For example, the user may have been previously diagnosed with breast cancer and may have begun a series of chemotherapy services as part of their cancer journey. At least partially as a side-effect of the chemotherapy services, blood labs may indicate that the user has developed a certain level of cardiovascular (e.g., or "cardiac") toxicity (e.g., damage to the heart by harmful chemicals). The UN system may receive updated user data (e.g., including the updated blood labs) associated with the user's updated condition and/or updated service status. Similar to as described above, a segmentation model of the UN system may determine one or more scores related to a classification of the user. In this example, in addition to being classified as presenting breast cancer, the UN system may further determine that the user should be classified as presenting cardiovascular toxicity with a moderate level of severity. This classification may further cause the occurrence of a second trigger, which may be associated with a cardiac navigation program. In this case, however, instead of assigning the user to another program (i.e., the cardiac toxicity navigation program) in addition to the currently assigned breast cancer navigation program, the UN system may determine to suppress the second trigger (e.g., not assigning the user to the cardiac toxicity navigation program). For example, the UN system may determine (e.g., partially by comparing the scores output by the segmentation model) that the cardiac toxicity is likely a byproduct of the breast cancer chemotherapy services. As such, instead of assigning the user to a new navigation program, the UN system may determine to integrate navigation service related to the cardiac toxicity into the currently assigned breast cancer navigation program. For example, messages that would otherwise be directed to a second user navigator of the cardiac navigation program may instead be directed to a first user navigator of the breast cancer navigation program. In this way, the UN system may deliver holistic navigation service to the user, for example, reducing the number of separate communication channels between USPs of the service organization and the user.

In another example, the UN system may present user assessment data to a dashboard of a USP user device for coordinating assignments of users to one or more user navigation programs. In an example, the UN system may determine an assessment for each user of a plurality of users of a service organization. An assessment may correspond to at least one of: (1) a segment in which the user is classified, whereby the segment is associated with the occurrence of a trigger, or (2) at least one user navigation program for which the user qualifies or is already assigned. In an example for generating an assessment, the UN system may receive user data of a user. The user data may be received as streaming data (e.g., in real-time) and be input by the UN system into a segmentation model, as described above. One or more triggers may occur for the user, based on segment classifications determined at least in part by the segmentation model, which in turn is incorporated into the assessment for the user. The UN system further determines one or more user navigation programs for which the user may be already assigned and/or may qualify for (e.g., based on the trigger that occurred). The UN system may then provide assessments for each of the users of the service organization to the user device of the USP (e.g., a user navigation coordinator) for subsequent presentation on the user device (e.g., on a user interface (UI) such as a dashboard). The dashboard may be used by the user navigation coordinator for coordinating assignments of users to one or more navigation programs. For example, the dashboard may indicate users who are already assigned to more than one navigation program, and may indicate opportunities for re-channeling the user into a single navigation program that covers service for multiple conditions. In another example, the dashboard may indicate which triggers have the most common overlap for users. The coordinator may use this information to determine opportunities for coordinating service between navigation programs that are respectively associated with the triggers that most commonly overlap.

In another example, the UN system may facilitate updating a user interface of a user device of a user navigator. In an example, a service organization may maintain plurality of user navigation programs (e.g., breast cancer navigation program, colon cancer navigation program, cardiac navigation program, etc.). Each of these user navigation programs may be staffed with one or more user navigators, each of whom may be assigned to one or more users that are assigned to the particular navigation program. In some examples, the UN system may receive an indication that a user is assigned to more than one user navigation program. For example, the user may be assigned to a first navigation program (e.g., breast cancer navigation program), and accordingly may be paired with a first user navigator staffed with the first navigation program. The user may also be assigned to a second navigation program, and accordingly may be paired with a second user navigator staffed with the second navigation program (e.g., cardiac navigation program). The UN system may transmit a message to a first user device of the first user navigator, whereby the message may be associated with an aspect of the user's journey through the first navigation program. For example, the message may indicate to the first user navigator that they should remind the user about an upcoming chemotherapy appointment that is scheduled in the course of the user's service. The first user navigator may then coordinate with the user following the chemotherapy appointment to schedule blood labs. The results of the blood labs may indicate an updated condition (or an updated service status) of the user (e.g., increased levels of cardiac toxicity). These results may be transmitted (e.g., from a user device of the first user navigator or other suitable device) to the UN system as a feedback message for further processing. The UN system may utilize the feedback message to generate a second message for transmission to a second user device of the second user navigator, whereby the message may be associated with a second aspect of the user's journey through the second navigation program. For example, the second message may indicate to the second user navigator (from the cardiac navigation program) that the user should schedule follow up appointments with the cardiologist to discuss the increased cardiac toxicity level determined from the blood labs. It should be understood that messages may be transmitted/received to/from the UN system in substantially real-time. For example, feedback generated based on blood lab results may be received by the UN system (e.g., from the first user navigator's user device, the service management system, etc.), processed, and then a subsequent message may be generated and transmitted by the UN system to another (or the same) user navigator in real-time (e.g., within seconds, minutes, etc.). In this way, the UN system may efficiently coordinate user service for users who may be assigned to multiple user navigators (and/or navigation programs).

In another example, the UN system may determine a customized user navigation program for a user. The UN system may then present a user navigation task to a user interface of a user navigator assigned to the user enrolled in the customized user navigation program. For example, the UN system may receive user data associated with a user of a service facility. The UN system may detect a first occurrence of a first trigger based in part on the user being classified within a first segment (e.g., stage 1 breast cancer) associated with the first trigger. The UN system may further detect a second occurrence of a second trigger based in part on the user being classified within a second segment (e.g., high level of cardiac toxicity) associated with the second trigger. The first and second segments may further be respectively associated with first and second priorities, which may be used to prioritize a user among other users for being assigned to a user navigation program. A priority may be based on one or more factors, including, but not limited to, a severity of a condition associated with the segment, a determined relevance of a navigation program for a given stage of condition, a number of other users that are already in queue to be assigned to a navigation program, etc. The UN system may determine a customized navigation program for the user based on at least one of multiple factors, including: (1) the first segment, (2) the second segment, (3) the first priority, or (4) the second priority. For example, the UN may determine the customized navigation program by assigning the user to one or more user navigators. A user navigator may be assigned to the user based on one or more factors, including a specialty of the navigator (e.g., trained to handle breast cancer cases), a level of case complexity the navigator is trained to handle (e.g., associated with a higher or lower severity of the user's condition), an availability of other user navigators, etc. Upon assigning a particular user navigator to the user, the UN system may thereafter route tasks to the particular user navigator that are curated for the particular navigator (e.g., relevant subject matter, level of complexity, etc.). In this way, the UN system may efficiently coordinate among available user navigators to provide a high quality of service for the user (e.g., avoiding collisions of messages between user navigators, and/or between different user navigators and the user).

In another example, the UN system may be utilized to procure service resources. For example, the UN system may receive a plurality of user data respectively associated with a plurality of user records of users of a service organization. The UN system may determine an assessment for each user of the plurality of users. In some examples, the assessment may include a determination of one or more triggers that occur based in part on the user data. In some examples, the assessment may include a determination of whether the user is already assigned and/or qualifies to be assigned to at least one user navigation program. The UN system then utilizes the plurality of assessments to determine (e.g., forecast) a need for one or more service resources in the future. For example, the plurality of assessments may indicate that a number of users are candidates for being assigned to a breast cancer navigation program. In some examples, the users may be associated with a particular service facility of the service organization. The UN system may determine that one or more additional user navigators may be needed in the near future to meet the increased demand. In some examples, the user navigators may be relocated to the particular service facility, for example, if it is determined that a non-virtual (e.g., in-person) and high-touch navigation program is appropriate. In some examples, the UN system may determine other service resources that may be procured to meet forecasted demand (e.g., service equipment, a particular type of medication, other USP resources). The UN system may then provide a procurement recommendation associated with the determined number of service resources to a user device of a user navigation coordinator for presentation on the user device.

The present disclosure provides several technical advantages over existing solutions that improve the functioning of the computer system in which a UN system is implemented. For example, conventional techniques include utilizing a significant amount of computing and/or human resources to transmit messages for coordinating and managing user service. For example, often a user may be assigned to more than one user navigation program, and thus be assigned to more than one user navigator. Each user navigator may transmit and/or receive a series of messages from the user. Typically, each user navigator program may be independent of other user navigation programs (e.g., effectively siloed), resulting in duplicated (and even conflicting) messages transmitted between respective user navigators and the user (which may collectively be known as "message collisions"). This may lead to reduced quality of service (e.g., user frustration), and may even result in the user dropping out of the user navigation program(s). When the user navigators do coordinate amongst each other, this often leads to a substantial number of message exchanges between the user navigators (and/or other USPs) to ensure that a unified message (e.g., non-redundant and consistent) is delivered to the user. However, embodiments of the present disclosure may reduce the total number of message required per user. For example, the UN system may facilitate coordination between user navigators of different user navigation programs. This may result in fewer message exchanges used to communicate with the user. In another example, the UN system may be utilized to reduce and/or simplify the number of independent navigation programs. For example, instead of assigning a user to a new navigation program (who is already assigned to one program), the UN system may route messages to a user navigator of the currently assigned program. This may, in turn, lead to better communication with the user, fewer messages being transmitted or received, and increased user satisfaction. By reducing the total number of messages required per user, multiplied over a large number of users in a service system, this may improve network efficiency (e.g., increasing available bandwidth) and increase computing resources available to the computer system. This may also lead to improved memory utilization because the number of messages required for processing and storage is reduced. Additionally, because the system and associated prediction models (e.g., the segmentation model) are trained using the largest and most relevant datasets available (i.e., those maintained in the world's largest clinical data warehouse), the predictions made using the described system (segmentations and resulting triggers) are more precise and more accurate than those made by prior art systems trained using smaller datasets. For example, these datasets may be drawn from user data including a large corpus of user records, clinician notes, blood samples, etc. Additionally, because of the higher quality of the prediction models, fewer computing resources are required to make the predictions as would be required using conventional techniques.

Referring first to FIG. 1, a block diagram of an example of an interaction system 100 is illustrated. Generally, in interaction system 100, data can be generated at one or more system components 102 and/or user devices 104. Management engine 106 can manage the flow of communications within interaction system. Transformative processing engine 108 can receive, intercept, track, integrate, process, and/or store such data.

Data flowing in interaction system 100 can include a set of communications. Each of one, some of all communications can include (for example) an encoding type, authentication credential, indication of a content size, identifier of a source device, identifier of a destination device, identifier pertaining to content in the communication (e.g., an identifier of an entity), a processing or reporting instruction, a procedure specification, transmission time stamp, and/or sensor measurement. Data may, or may not, selectively pertain to a particular entity and/or client. Data can, depending on the implementation, include individually identifiable information and/or de-identified information as it pertains to an entity and/or client. Data may, but need not, include protected information.

For example, a system component 102 can include, for example, a sensor to detect a sensor measurement and can thereafter generate and transmit a communication that reflects the sensor measurement. The communication may be transmitted at routine times and/or upon detecting a threshold (e.g., one or more) number of measurements or a measurement satisfying a transmission condition (e.g., exceeding a threshold value). In some instances, the sensor measurement corresponds to one reflecting a property of an object or entity (e.g., person) near the sensor. The communication may then include an identifier of the object or entity. The identifier can be determined, for example, based on detection of a nearby electronic tag (e.g., RFID tag), a detected user input received at a user interface of component 102, and/or data in a corresponding communication received from a user device.

As another example, a user device 104 can be configured to detect input received at an interface of the device. The input can include, for example, an identifier of an object or entity, an instruction, a characterization of an object or entity, an identification of an assessment to be performed, a specification of an aggregation or data processing to be performed, and/or an identification of a destination for a data-analysis report. User device 104 can further be configured to detect input requesting particular data, to generate a request communication (e.g., to be sent to transformative processing engine), to receive the requested data and/or to present the received data.

The depicted engines, devices and/or components can communicate over one or more networks. A network of one or more networks can include a wired network (e.g., fiber, Ethernet, powerline ethernet, ethernet over coaxial cable, digital signal line (DSL), or the like), wireless network (e.g., Zigbee™, Bluetooth™, WiFi™, IR, UWB, WiFi-Direct, BLE, cellular, Long-Term Evolution (LTE), WiMax™, or the like), local area network, the Internet and/or a combination thereof. It will be appreciated that, while one or more components 102 and one or more user devices 104 are illustrated as communicating via transformative processing engine 108 and/or management engine 106, this specification is not so limited. For example, each of one or more components 102 may communicate with each of one or more user devices 104 directly via other or the same communication networks.

A component 102 can be configured to detect, process and/or receive data, such as environmental data, geophysical data, biometric data, chemical data (e.g., chemical composition or concentration analysis data), and/or network data. The data can be based on data detected, for example, via a sensor, received signal or user input. A user device 104 can include a device configured to receive data from a user and/or present data to a user. It will be appreciated that, in some instances, a component 102 is also a user device 104 and vice-versa. For example, a single device can be configured to detect sensor measurements, receive user input and present output.

A component 102 can be configured to generate a communication that is in one or more formats, some of which can be proprietary. For example, an imaging machine (e.g., one of one or more components 102) manufactured by company A, located within a first facility (e.g., facility 110), and belonging to a first client, may save and transfer data in a first format. An imaging machine (e.g., one of one or more components 102) manufactured by company B, located within the first facility (e.g., facility 110), and belonging to the first client, may save and transfer data in a second format. In some examples, data from certain components is transformed, translated, or otherwise adjusted to be recognizable by transformative processing engine 108. Thus, continuing with the example from above, when the imaging machines manufactured by companies A and B are located within the first facility belonging to the first client, they may nevertheless save and transfer data in different formats. In some examples, one or more components 102 communicate using a defined format.

In some examples, each of one or more components 102 are each associated with one or more clients within a same or different interaction systems. For example, certain ones of one or more components 102 may be associated with a first client, while other ones of one or more components 102 may be associated with a second client. Additionally, each of one or more components 102 may be associated with a facility 110 (e.g., client facility). Each facility 110 may correspond to a single location and/or focus. Exemplary types of facilities include server farm facilities, web-server facilities, data-storage facilities, telecommunication facilities, service facilities, and/or operational facilities. For example, a first facility may include a structure at a first location at which one or more resources (e.g., computational resources, equipment resources, laboratory resources, and/or human resources) are provided. Each of the one or more resources may be of a first type in a first set of types. A resource type can be identified based on, for example, a characteristic of the resource (e.g., sensor inclusion) and/or a capability of providing each of one or more services. Thus, for example, resources at a first facility may be better configured for handling a particular type of service requests compared to those in another facility. As another example, different facilities may include resources of similar or same types but may vary in terms of, for example, accessibility, location, etc.

Transmission of data from one or more components 102 to transformative processing engine 108 may be triggered by a variety of different events. For example, the data may be transmitted periodically, upon detection of an event (e.g., completion of an analysis or end of a procedure), upon detection of an event defined by a rule (e.g., a user-defined rule), upon receiving user input triggering the transmission, or upon receiving a data request from transformative processing engine 108. Each transmission can include, e.g., a single record pertaining to a single entity, object, procedure, or analysis or multiple records pertaining to multiple entities, objects, procedures, or analyses.

In some examples, at least some of one or more user devices 104 are associated with facility 110. In some examples, at least some of one or more user devices 104 need not be associated with facility 110 or any other facility. Similar to one or more components 102, one or more user devices 104 may be capable of receiving, generating, processing, and/or transmitting data. Examples of one or more user devices 104 include, for example, a computer, a mobile device, a smart phone, a laptop, an electronic badge, a set-top box, a thin client device, a tablet, a pager, and other similar user devices). One or more user devices 104 may be configured to run one or more applications developed for interacting with data collected by transformative processing engine 108. For example, those user devices of one or more user devices 104 that are not associated with facility 110 may be configured to run one or more third-party applications that may rely in part on the data gathered by transformative processing engine 108.

Each of one or more components 102 and one or more user devices 104 may be utilized by one or more users (not shown). Each of the one or more users may be associated with one or more clients. For example, one of the one or more users can be associated with a client as a result of being employed by the client, physically located at a location of the client, being an agent of the client, or receiving a service from the client.

In some examples, one or more components 102 and one or more user devices 104 may communicate with transformative processing engine 108 and management engine 106 via different information formats, different proprietary protocols, different encryption techniques, different languages, different machine languages, and the like. As will be discussed with reference to FIG. 2, transformative processing engine 108 is configured to receive these many different communications from one or more components 102, and in some examples from one or more user devices 104, in their native formats and transform them into any of one or more formats. The received and/or transformed communications can be transmitted to one or more other devices (e.g., management engine 106, an entity device, and/or a user device) and/or locally or remotely stored. In some examples, transformative processing engine 108 receives data in a particular format (e.g., the HL7 format) or conforming to any other suitable format and/or is configured to transform received data to conform to the particular format.

One or more components 102 of facility 110 can include and/or has access to a local or remote memory for storing generated data. In some examples, the data is stored by one or more servers local to facility 110. The record service can be granted access to the data generated and/or transmitted by one or more components 102. In some examples, the record service includes a server or a plurality of servers arranged in a cluster or the like. These server(s) of the record service can process and/or store data generated by one or more components 102. For example, one or more records can be generated for each entity (e.g., each record corresponding to a different entity or being shared across entities). Upon receiving a communication with data from a component (or facility), the record service can identify a corresponding record and update the record to include the data (or processed version thereof). In some examples, the record service provides data to transformative processing engine 108.

Irrespective of the type of facility, facility 110 may update data, maintain data, and communicate data to transformative processing engine 108. At least some of the data may be stored local to facility 110.

A user interacting with a user device 104 can include, for example, a client customer, client agent and/or a third party. A user may interact with user device 104 and/or component 102 so as to, for example, facilitate or initiate data collection (e.g., by a component 102), provide data, initiate transmission of a data request, access data and/or initiate transmission of a data-processing or data-storage instruction. In some instances, one or more user devices 104 may operate according to a private and/or proprietary network or protocols. In other examples, one or more user devices 104 may operate on public networks. In any case, however, transformative processing engine 108 can have access to the one or more components and can communicate with them via a public, private, and/or proprietary network or protocols. The use of one or more private and/or proprietary protocols can promote secure transfer of data.

Figure 2:
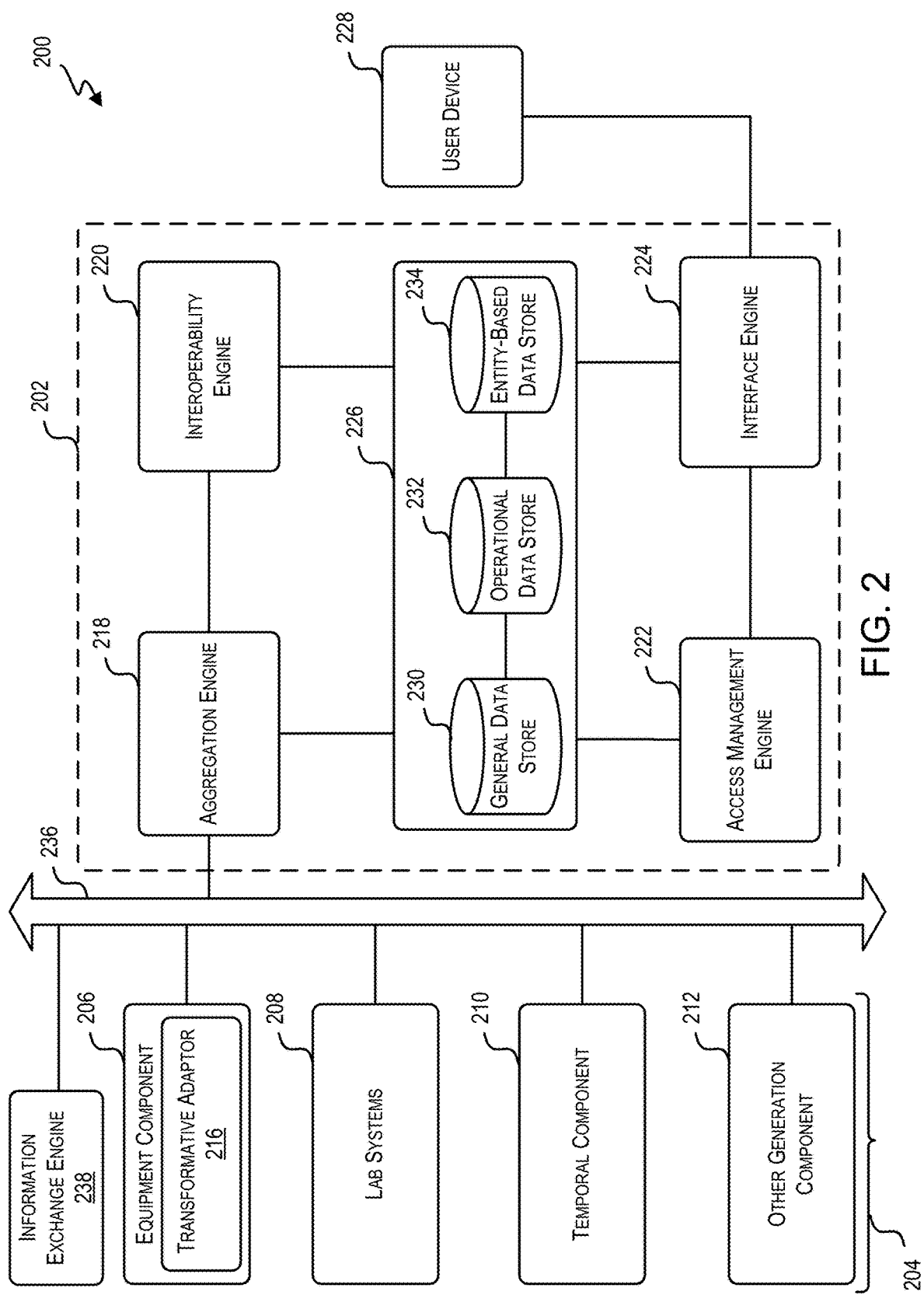
FIG. 2 is an example block diagram illustrating an interaction system in which techniques relating to assigning a user to a user navigation program may be implemented, according to at least one example.

Referring next to FIG. 2, a block diagram of an example of an interaction system 200 is shown. Interaction system 200 includes a transformative processing engine 202. Transformative processing engine 202 is an example of transformative processing engine 108 discussed with reference to FIG. 1. Interaction system 200 also includes one or more generation components 204. In particular, one or more generation components 204 include an equipment component 206, a lab systems component 208, a temporal component 210, and other generation component 212. One or more generation components 204 are examples of one or more components 102 discussed with reference to FIG. 1. In some examples, the data may pass to the transformative processing engine 202 via an information exchange service bus 236 (e.g., an enterprise service bus). In some examples, only a portion of the is passed via the information exchange service bus 236, while other portions are passed directly to the transformative processing engine 202 without first passing over the information exchange service bus 236.

Generally, one or more generation components 204 includes any suitable device or system capable of generating data in the context of an interaction system. For example, the other generation component 212 may include a sensor on a door, and equipment component 206 may include a sophisticated computer-controlled laser device. In either case, each generation component generates some type of data. For example, the data provided by the sensor may be used to address security concerns or assessing heating, ventilating, and air conditioning (HVAC) costs for an institution. The data provided by the laser device may have been provided while engaged in a procedure and may then be used by other entities in the future to decide how to use the device.

As discussed in further detail herein, data generated by one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical interaction system includes thousands of generation components producing data in hundreds of formats. In order to harness the power that comes from such a large amount of data to make informed decisions, it is desirable that all, or at least a large portion of the data, is shared. Use of transformative processing engine 202 in accordance with techniques described herein may achieve this design-making large amounts of data, in many different originating formats available to various types of users, via one or more interfaces. At least a portion of the data generated by the generation components 204 may be provided to the transformative processing engine 202. In some examples, each generation component 204 includes an agent that executes on the generation components 204 and determines which data to send to the transformative processing engine 202 and other engines described herein. In some examples, the generation components 204 provide data to the transformative processing engine 202 via a messaging bus (e.g., an information exchange service bus 236). The messaging bus, which may be included in the transformative processing engine 202 or separate, is able to see data that moves throughout the interaction system 200. The information exchange service bus 236 also includes a subscription registry that can be used to manage subscriptions to the information exchange service bus 236 for certain data (e.g., data having certain characteristics). The information exchange service bus 236 may send and/or direct data to certain other entities when appropriate as indicated by subscription records in the registry.

While one or more generation components 204 are illustrated adjacent to each other, it is understood that each may be located within one facility or that the components may be spread out among many facilities. In addition, in some examples, one or more generation components 204 belong to different clients.

Turning now to equipment component 206, this component includes any machine, contrivance, implant, or other similar related article, that is intended to aid in reaching a particular objective. In some instances, equipment component 206 includes one or more sensors to detect environmental or other stimuli. Equipment component 206 can include, for example, equipment to monitor a stimulus, detect stimulus changes, detect stimulus-indicative values, and so on. Exemplary equipment components 206 include an imaging device, a device that detects and characterizes electrical signals, a device that detects pressure, and/or a device that detects concentration of one or more particular elements, compounds and/or gases.

As illustrated, equipment component 206 includes transformative adaptor 216. In some examples, transformative adaptor 216 is a device that transforms, translates, converts, or otherwise adjusts output data from equipment component 206. For example, an equipment component 206 can be a scanner that outputs its results in format A, but the majority of other scanners in the interaction system output their results in format B. Transformative adaptor 216 may be implemented to convert or otherwise adjust the results in format A to conform closer to format B. For example, the conversion from format A to format B may be performed using a conversion rule, which may be user-define or learned. Transformative processing engine 202 may perform similar tasks as it relates to all data generated within interaction system 200. In this manner, transformative adaptor 216 can perform an initial step in the process of transformation, translation, conversion, or adjustment of the output of equipment component 206. In some examples, transformative adaptor 216 is implemented in hardware, software, or any suitable combination of both. In some examples, other transformative adaptors (not shown) may be implemented within others of one or more generation components 204. In some examples, equipment component 206 may not include transformative adaptor 216.

Lab systems component 208 includes any suitable laboratory equipment or system that is intended to analyze material, such as biological material. This includes, for example, laboratory equipment that analyzes biological samples; electric microscopes; ultracentrifuges; data collection devices, including Kymographs, sensors connected to a computer to collect data; monitoring devices; computers used to report results of lab tests, and other similar laboratory equipment. Each of the above-listed components generates data that is provided (directly or indirectly) to transformative processing engine 202.

Temporal component 210 may include any suitable computing devices used with respect to interaction system 200. For example, temporal component 210 can be configured to allocate a resource to a particular entity during a particular temporal window. Temporal component 210 can monitor a schedule for the resource and can identify one or more available temporal windows that may be secured by a particular entity. Upon receiving an indication, temporal component 210 may update a schedule of a resource to reflect that a particular temporal window is to be allocated for service of a particular entity.

Each of one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with transformative processing engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or transformative processing engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive data from one or more sensors. The sensors may be any suitable type of sensor to capture data. Such captured data may be shared with transformative processing engine 202 in accordance with techniques described herein. In some examples, the sensors may also be configured to detect the location and other details about the component or the user device. In some examples, the component and the user device may include global positioning chips that are configured to determine a geolocation.

Transformative processing engine 202 includes an aggregation engine 218, an interoperability engine 220, an access management engine 222, an interface engine 224, and a data store 226. Generally aggregation engine 218 is configured to collect data from multiple communications. The data may be from one or multiple generation components 204 and/or may be of same or different formats. Aggregation engine 218 may be configured to perform one or more operations on the collected data. For example, aggregation engine 218 may tag data, log data, perform protocol conversion, and may support one-to-many communications. The collection may be asynchronous. In some examples, the data has been saved locally in connection with one or more generation components 204 in many different formats having many different data structures.

Aggregation engine 218 can identify data to be aggregated based on, for example, intra-communication data, a current time, a source generation component, and/or one or more aggregation rules. For example, an aggregation rule may specify that data is to be aggregated across all communications that include content with a same entity identifier. An aggregation may be dynamic. For example, aggregated data may reflect that from within a most recent 12-hour period. Thus, an aggregation may be updated in time to exclude older data from the aggregation and to include newer data.

Aggregation engine 218 can be configured to provide data from one or more communications to interoperability engine 220. Interoperability engine 220 can be configured to perform one or more operations on the received data and store it in data store 226. For example, interoperability engine 220 may perform semantic tagging and indexing of data. This may include extracting field values from data, categorizing data (e.g., by type of data, characteristic of an entity, location of facility, characteristic of facility, and the like), anonymizing or partially-anonymizing data, and the like. Interoperability engine 220 may also include a high availability cache, an alerts engine, and a rules engine. In some examples, interoperability engine 220 operates synchronously.

From interoperability engine 220, data flows to data store 226. Data store 226 (and any other data store discussed herein) may include one or more data stores, which may be distributed throughout two or more different locations (e.g., present on different devices, which can include devices of different entities and/or a cloud server). In some examples, data store 226 includes a general data store 230, an operational data store 232, and an entity-based data store 234. Within each of the data stores 230, 232, and 234 is stored data. Depending on the structure of the particular data store, certain data stores may include rules for reading and writing. The data stores 230, 232, and 234 may include records, tables, arrays, and the like, which may be relational or non-relational. Depending on the data store, records for individual entities, business and analytics information, output data from one or more generation components 204, and the like may be retained. The data within the data stores 230, 232, and 234 include elements or tags such that a particular data (e.g., for a single entity, protocol, etc.) can be retrieved.

Access management engine 222 is configured to manage access to features of transformative processing engine 202, including access to the data retained in data store 226. For example, access management engine 222 may verify that a user device such as user device 228 is authorized to access data store 226. To verify the user device 228, access management engine 222 may require that a user of the user device 228 input a username and password, have a profile associated with the interaction system, and the like. Access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

Interface engine 224 is configured to retrieve the data from data store 226 and provide one or more interfaces for interacting with elements of transformative processing engine 202. For example, interface engine 224 includes an interface by which an application running on user device 228 can access portions of data within data store 226.

As described herein, an information exchange engine 238 shares a network connection with the information exchange service bus 236. The information exchange engine 238 is configured to monitor data (e.g., messages) that is passed over the information exchange service bus 236 and, from the monitored data, select certain portions to provide to one or more authorized user devices. The information exchange engine 238 is also configured to route inbound messages and route outbound messages, as described herein. The information exchange engine 238 is also configured to generate customized messages based on dependent user data.

Figure 3:
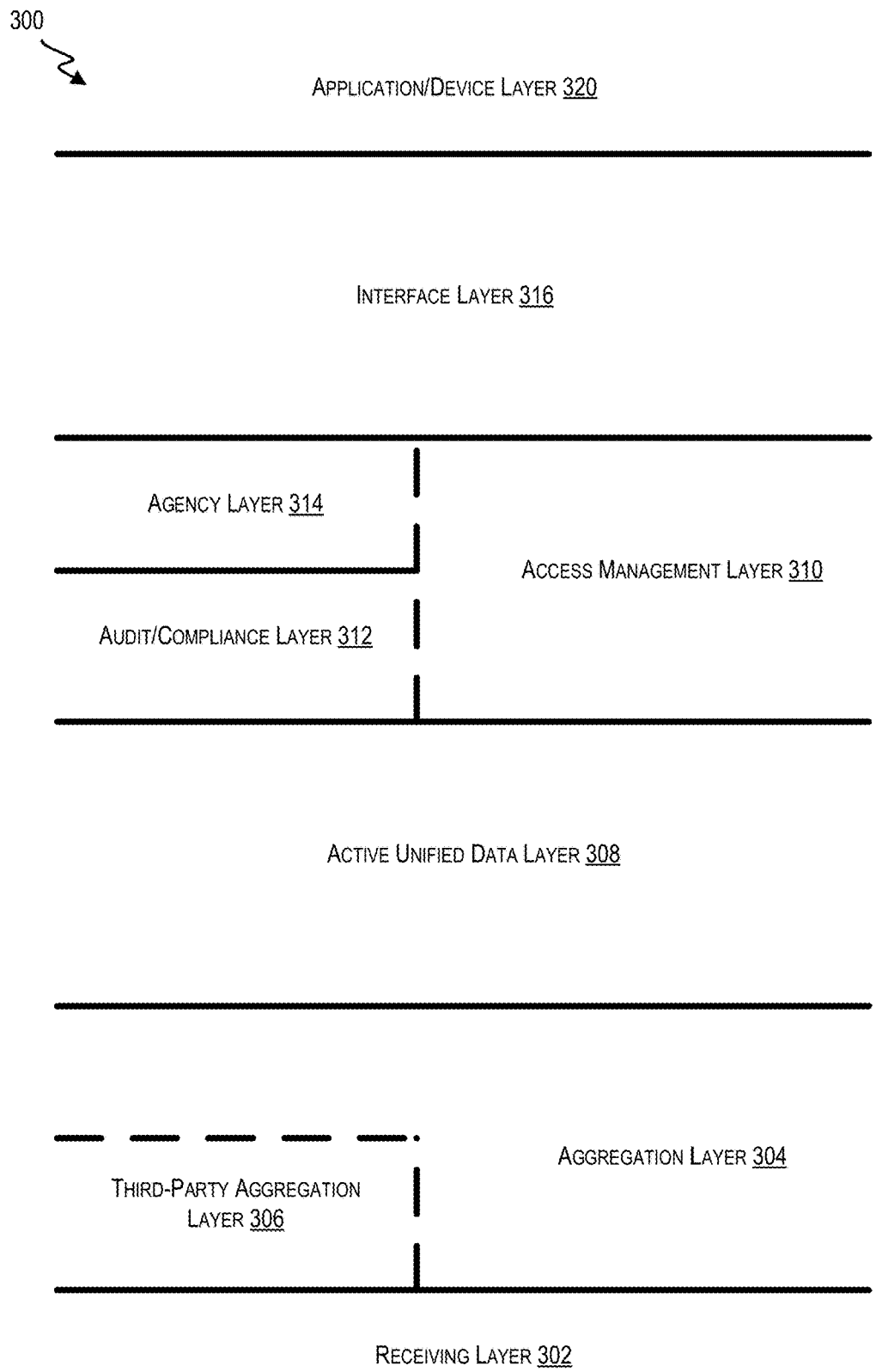
FIG. 3 is an example schematic model illustrating a network communication model in which techniques relating to assigning a user to a user navigation program may be implemented, according to at least one example.

Turning next to FIG. 3, an architecture stack 300 is shown. In some examples, techniques relating management of data are implemented in accordance with architecture stack 300. And while architecture stack 300 is illustrated as having a particular structure, it is understood that other structures, including those with more or less layers than illustrated, is within the scope of this specification. In some examples, architecture stack 300 is implemented across an interaction system having a plurality of systems belonging to the same client or spread across different clients. Thus, architecture stack 300 can be used to integrate different systems of different organizations, entities, and the like and to provide a fluid sharing of information among elements within the interaction system and without the interaction system. In some instances, a multi-layer part of architecture stack 300 is implemented at a single system or device within an interaction system.

The different layers of architecture stack 300 will be described generally with reference to FIG. 3 and in detail with reference to subsequent figures. Architecture stack 300 includes a receiving layer 302 as the bottom-most layer. Receiving layer 302 includes receiving data from elements that share data with other elements within an aggregation layer 304. For example, as detailed herein, receiving layer 302 can include receiving data from generation components that generate data. As such, receiving layer 302 is where data that has been created is received. In some examples, the data within receiving layer 302 may be in its raw formats. The output may then be transmitted to aggregation layer 304. In some examples, components of receiving layer 302 may have complimentary layers to facilitate data transfer. For example, the components may include a data generation and/or a data transmission layer for providing data to receiving layer 302.

Elements of aggregation layer 304 aggregate the data generated by the elements of receiving layer 302. For example, the elements of aggregation layer 304 may include aggregation engines that collect data from generation components located within receiving layer 302. Such aggregation may be performed periodically, in response to a user request, according to a schedule, or in any other suitable manner. In some examples, data of aggregation layer 304 may be aggregated according to input and/or rules and may aggregate across records pertaining to, e.g., a facility, entity, time period, characteristic (e.g., demographic characteristic or condition), outcome, and any other suitable input and/or rules. The aggregation may include compiling the data, generating a distribution, generating a statistic pertaining to the data (e.g., average, median, extremum, or variance), converting the data, transforming the data to different formats, and the like.

Next, architecture stack 300 includes an active unified data layer 308. Elements of active unified data layer 308 receive data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of active unified data layer 308 may receive information collected or generated within aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within active unified data layer 308.

Architecture stack 300 also includes an access management layer 310, which can include an audit/compliance layer 312 and/or an agency layer 314. Access management layer 310 includes elements to manage access to the data. For example, access management layer 310 may include elements to verify user login credentials, IP addresses associated with a user device, and the like prior to granting the user access to data stored within active unified data layer 308.

Audit/compliance layer 312 includes elements to audit other elements of architecture stack 300 and ensure compliance with operating procedures. For example, this may include tracking and monitoring the other elements of access management layer 310.

Agency layer 314 includes an access location (e.g., a virtual private network, a data feed, or the like) for elements of agencies that are interested in the operations of the interaction system in which architecture stack 300 is implemented. For example, agency layer 314 may allow a governmental entity access to some elements within architecture stack 300. This may be achieved by providing the governmental entity a direct conduit (perhaps by a virtual private network) to the elements of access management layer 310 and the data within active unified data layer 308. Audit/compliance layer 312 and agency layer 314 are sub-layers of access management layer 310.

Architecture stack 300 also includes interface layer 316. Interface layer 316 provides interfaces for users to interact with the other elements of architecture stack 300. For example, clients, entities, administrators, and others belonging to the interaction system may utilize one or more user devices (interacting within application/device layer 320) to access the data stored within active unified data layer 308. In some examples, the users may be unrelated to the interaction system (e.g., ordinary users, research universities, for profit and non-profit research organizations, organizations, and the like) and may use applications (not shown) to access the elements within architecture stack 300 via one or more interfaces (e.g., to access data stored within active unified data layer 308). Such applications may have been developed by the interaction system or by third-parties.

Finally, architecture stack 300 includes application/device layer 320. Application/device layer 320 includes user devices and applications for interacting with the other elements of architecture stack 300 via the elements of interface layer 316. For example, the applications may be web-based applications, entity portals, mobile applications, widgets, and the like for accessing the data. These applications may run on one or more user devices. The user devices may be any suitable user device as detailed herein.

Figure 4:
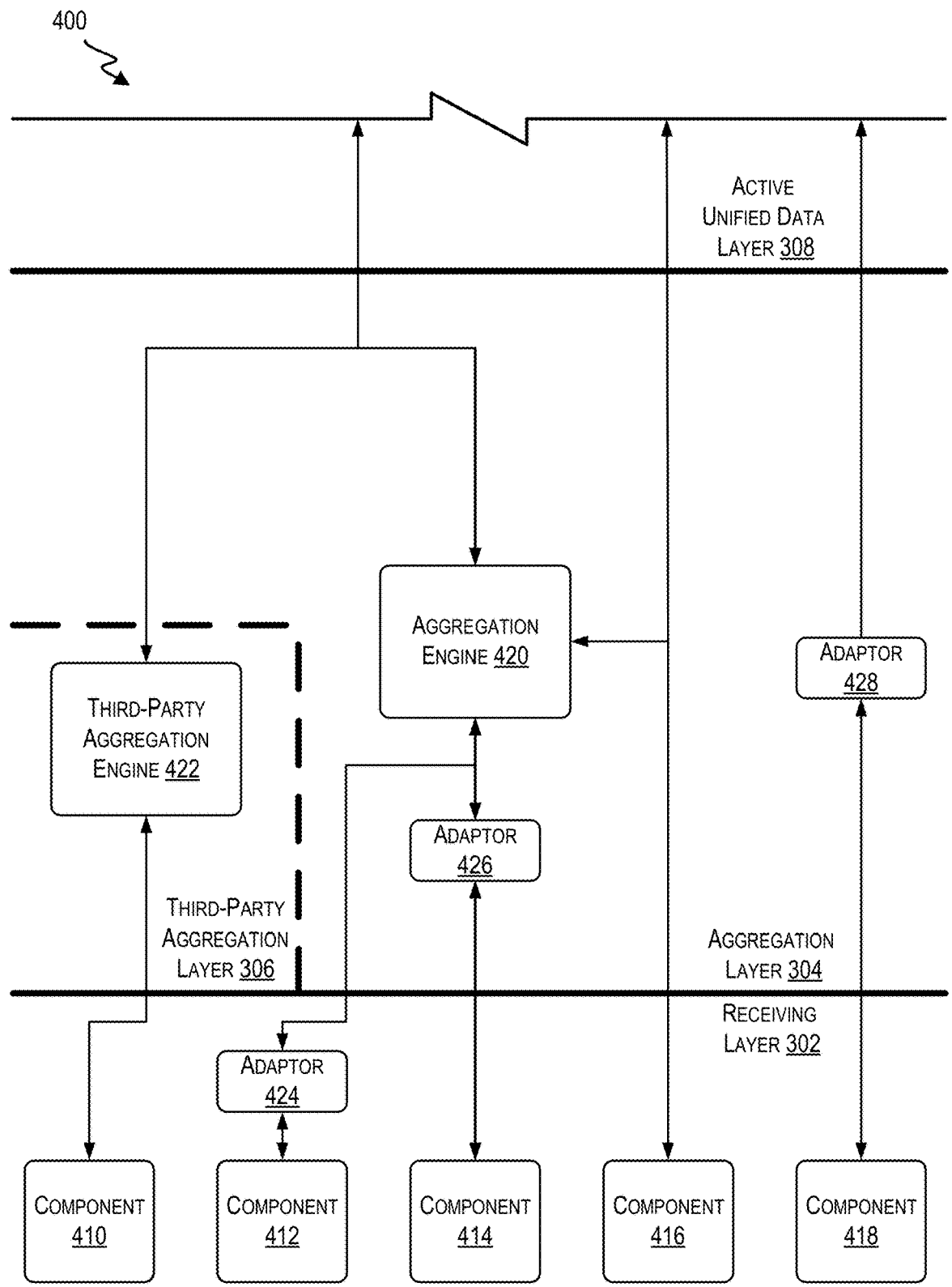
FIG. 4 is an example schematic model illustrating an aspect of the network communication model of FIG. 3 in more detail.

Turning next to FIG. 4, a diagram 400 is shown that depicts a portion of architecture stack 300 according to at least one example. In particular, the diagram 400 includes receiving layer 302, aggregation layer 304, aggregation layer 306, and a portion of active unified data layer 308. Receiving layer 302 receives data from one or more components 410-418. Components 410-418 are examples of one or more generation components 204. Components 410-418 may be spread across multiple facilities within a single or multiple clients. In some examples, components 410-418 may include complimentary layers to facilitate data transmission. For example, components 410-418 may include a transmission layer, generation layer, and/or a receiving layer to communicate data at receiving layer 302 and, in some examples, receive data from receiving layer 302.

In some instances, two or more of components 410-418 generate data according to different formats. The data can then be transformed, translated, or otherwise adjusted before an aggregation engine 420 (e.g., aggregation engine 218) or a third-party aggregation engine 422 (e.g., aggregation engine 218) collects the data. In some examples, the adjustment takes place within receiving layer 302. Thus, an adaptor 424 is associated with component 412 located in receiving layer 302. Adaptor 424 is an example of transformative adaptor 216. Adaptor 424 is implemented, as appropriate, in hardware, software, or any suitable combination of both. For example, transformative adaptor 216 may be a bolt-on adaptor that adjusts data as such data leaves component 412.

Other adaptors, such as adaptor 426 and adaptor 428, are implemented within aggregation layer 304. These adaptors can function in a similar manner as adaptor 424. In some examples, the data provided by component 414 is transmitted through adaptor 426 prior to being directed to aggregation engine 420. The data provided by component 416 is transmitted through aggregation layer 304 and/or enters aggregation engine 420 without having first traveled through an adaptor. The data provided by component 418 is transmitted through aggregation layer 304 and through adaptor 428. In some examples, component 418 provides for streaming of data. The data provided by component 410 is transmitted directly to third-party aggregation engine 422.

Aggregation engine 420 and third-party aggregation engine 422 function in a similar manner. In some examples, third-party aggregation engine 422 is operated by a different entity than the entity that operates aggregation engine 420 and may belong to different clients or a different interaction system. This may be because the data collected by third-party aggregation engine 422 differs in some way from the data collected by aggregation engine 420. In any event, aggregation engine 420 is configured to perform integration of data, including generic integration. For example, aggregation engine 420 performs one or more operations on data including tagging, logging, and protocol conversion. Aggregation engine 420 also supports one-to-many communications of data. In some examples, data flows between aggregation engine 420, the third-party aggregation engine 422, and some of components 410-418 and elements of active unified data layer 308.

The diagram 400 also includes the information exchange service bus 236 and the information exchange engine 238.

As introduced herein, messages passing through the aggregation layer 304 can pass over the information exchange service bus 236. In this manner, the information exchange engine 238 can access the messages, route the messages, and/or customize the messages.

Figure 5:
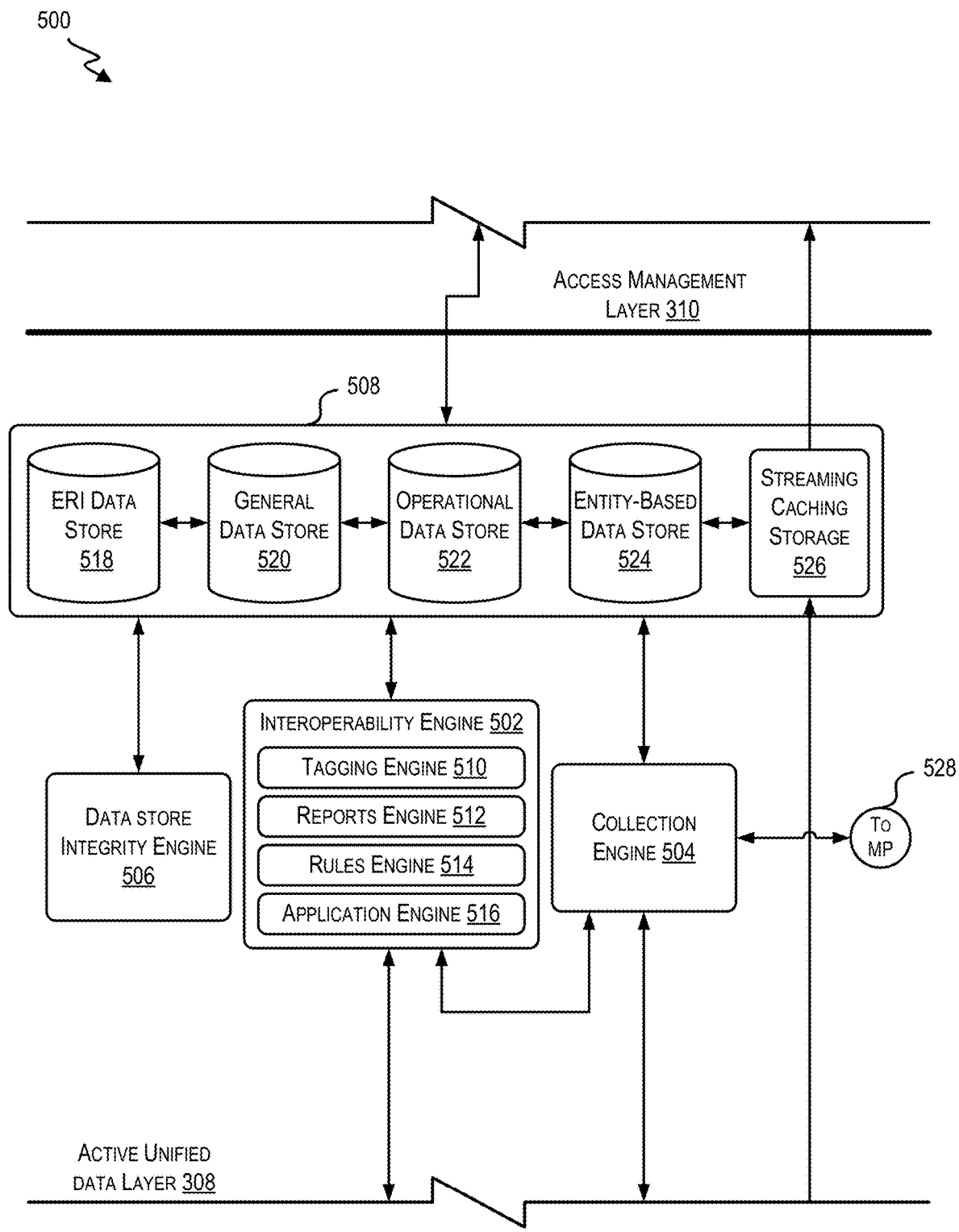
FIG. 5 is an example schematic model illustrating an aspect of the network communication model of FIG. 3 in more detail.

Referring next to FIG. 5, a diagram 500 is shown that depicts a portion of architecture stack 300 according to at least one example. In particular, diagram 500 includes active unified data layer 308 and a portion of access management layer 310. Active unified data layer 308, as illustrated in diagram 500, includes an interoperability engine 502 (e.g., interoperability engine 220), a collection engine 504, a data store integrity engine 506, and a data store 508 (e.g., data store 226). Generally, interoperability engine 502 receives data from elements within aggregation layer 304 (e.g., from aggregation engine 420) and performs one or more operations with respect to the data. Interoperability engine 502 also facilitates storage of at least a portion of the processed information in data store 508.

Collection engine 504 is configured to generate message indicators identifying flows of data by and between elements of an interaction system implemented using the techniques described herein. The flows of information include messages which include data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including data are transmitted from aggregation layer 304.

In some examples, the table also includes information for tracking the progress of the message from an origination node to a destination node. For example, typically when a message (e.g., any communication of data) is first received by transformative processing engine 108 (e.g., interoperability engine 502), management engine 106 (e.g., collection engine 504 of management engine 106) may generate a unique identifier for the message in order to track that message as it moves throughout the interaction system. The unique identifier may be included in the header of the message such that when the next node (e.g., component, device, server, etc.) after transformative processing engine 108 receives the message, that node can report back to management engine 106 that it saw the message. In this manner, management engine 106 may track messages from end-to-end for the life of the message.

In one example, the messages are requests. The requests may be generated based om user input at one of the components. The requests may be received by transformative processing engine 108 and integrated into the system. In some examples, management engine 106 may be notified that the requests have been received and may therefore be configured to generate message IDs for each request. These message IDs may then be associated with each of the requests. As the requests continue to move throughout the interaction system (e.g., away from transformative processing engine 108), management engine 106 may track their movement using the message IDs. If one of the requests does not arrive at its destination, management engine 106 may determine why the request was stopped. In some examples, this cause may be hardware related (e.g., an unplugged Ethernet cable, a broken router, etc.), software related (e.g., a router routing to the wrong location), or any other reason for orders not arriving at their correct destination.

In some examples, management engine 106 (e.g., collection engine 504 of management engine 106) may receive the message and/or message identifier directly from one of components 410-418. For example, one of components 410-416 may be configured to generate the unique message identifier and/or communicate directly with management engine 106. The message also may travel via one or more intermediate nodes on its way to the destination node. In some examples, a node is a component such as components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, collection engine 504 provides unique message identifiers to other elements of the interaction system to monitor the messages as they move throughout the interaction system. Collection engine 504 also provides a portion of the unique message identifiers to a management platform (indicated by a circle 528) for further analysis of the message identifiers. Such analyses may include reconciliation of lost messages, latency reporting, audit management and compliance, and other such analyses.

As mentioned previously, interoperability engine 502 is configured to store data in data store 508. A plurality of sub-engines 510-516 of interoperability engine 502 are configured to perform operations relating to storing data in data store 508.

Interoperability engine 502 includes a tagging engine 510 configured to perform semantic tagging and indexing of data. Tagging engine 510 therefore is configured to receive data, read metadata associated with the data, semantically scan the content of the data, and associate one or more tags with the data. Tagging engine 510 may therefore have access to hundreds, thousands, or even more possible tags. These tags may have been input by users, learned, pre-defined, generated by outside third-party mapping sources, and/or gathered from other components and/or data stores of the interaction system. For example, if the data is a chart for an entity, the tagging engine may be configured to read any metadata associated with the chart to determine which tags may be appropriate to associate with the chart. From the metadata, tagging engine 510 may determine that the chart is for a type of entity by reading metadata indicating that an author field is populated with the name of another particular type of entity. Tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the client or facility where the data originated, and other similar fields. The tags may be stored in association with the data (e.g., the chart) and/or may be stored independent from the data but include an identifier such that when searching tags the data may be capable of population.

Continuing with the example from above, if the data is a chart for a first type of entity, tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of data. This meaning and/or context may assist tagging engine 510 to determine one or more tags to associate with the data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, tagging engine 510 may also index portions of the data within one or more data stores of data store 508. In some examples, such indexing may be based in part on the selected tags.

Interoperability engine 502 also includes a reports engine 512 configured to generate one or more reports or alerts based on data. For example, reports engine 512 may generate reports when certain types of data are received or when data with certain characteristics is received. Reports engine 512 may also generate alerts. The reports and/or alerts generated by reports engine 512 may be outputted in the form of one or more communications to an administrator, an authorized user, or other similar user via a user device. Such communications can include, for example, signals, sirens, electronic notifications, popups, emails, and the like. Content of such communications may include information characterizing a performance metric, efficiency and/or outcomes; identifying concerning patterns; identifying losses of data; and the like. In some examples, the content is presented in the form of one or more documents, tables, figures, charts, graphs, and the like.

Interoperability engine 502 also includes a rules engine 514 configured to create and manage condition-response rules, alert/reports rules, data-formatting rules, data-sharing rules, transmission rules, aggregation rules, user authorization rules, and other similar rules. Such rules may be user-defined, fixed, learned by elements of the interaction system, and any combination of the foregoing. Finally, interoperability engine 502 includes an application engine 516 configured to provide service-oriented architecture web services.

Data store 508 includes an electronic record information data store 518 ("ERI data store 518"), a general data store 520, an operational data store 522, an entity-based data store 524, and a streaming caching storage 526. While data store 508 is illustrated as including a fixed number of data stores and storage elements, it is understood that data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables but that differ in one or more other variables. Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within ERI record data store 518 is retained data. In some examples, the information within ERI record data store 518 is organized according to entity identifying information. Thus, ERI record data store 518, in some examples, includes individually identifiable information. But it may also include de-identified information.

Within general data store 520 is retained data. The data may be stored in a relational database format or in any other suitable format. Thus, the data within general data store 520 may be retained in a data structure that includes one or more tables capable of accessing each other. In some examples, general data store 520 includes a subset of the information that is included in operational data store 522.

Within operational data store 522 is retained data in a relational database format. Thus, the data within operational data store 522 may be retained in a data structure that includes one or more data structures (e.g., tables) capable of accessing each other. Operational data store 522 is an example of an operational data warehouse. In operational data store 522 is joined many different types of data. In some examples, the operational data store 522 includes data pertaining to decision making as discussed herein and other data typically used.

Within entity-based data store 524 is retained data in a non-relational database format. Thus, the data within entity-based data store 524 may be retained in a structure other than tables. Such structure may be appropriate for large and complex data sets. In some examples, entity-based data store 524 (or any other data store) may be a unified system, which may include: a document-centric, schema-agnostic, structure-aware, clustered, transactional, secure, database server with built-in search and a full suite of application services. An example of such a unified system may be Marklogic. Entity-based data store 524 can support data aggregation, data organization, data indexing, data tagging and mapping to semantic standards, concept matching, concept extraction, machine learning algorithms, concept discovery, concept mining, and transformation of record information. In some examples, entity-based data store 524 includes data pertaining to decision making (similar to general data store 520) as discussed that is organized and accessed in a different manner. For example, the data within entity-based data store 524 may be optimized for providing and receiving information over one or more information exchanges. In some examples, entity-based data store 524 includes a subset of the information that is included in operational data store 522.

Finally, in some examples, streaming caching storage 526 is a streaming data cache data store. As discussed previously, certain components of components 410-418 may support streaming data to other components or user devices. Streaming caching storage 526 is a location where streaming data can be cached. For example, assume that component 418 is a piece of equipment operating at Location A and that a user using a computer in Location B desires to view a live of substantially live stream of outputs of the piece of equipment. Component 418 can send a portion of data to streaming caching storage 526 which can retain the portion of the data for a certain period of time (e.g., 1 day). Thus, streaming caching storage 526 is configured to cache data that can be streamed.

Diagram 500 also includes data store integrity engine 506. In some examples, data store integrity engine 506 is configured to ensure integrity of the information within data store 508. For example, data store integrity engine 506 applies one or more rules to decide whether information within all or part of data store 508 should be scrubbed, removed, or adjusted. In this manner, confidence is increased that the information within data store 508 is accurate and current.

Figure 6:
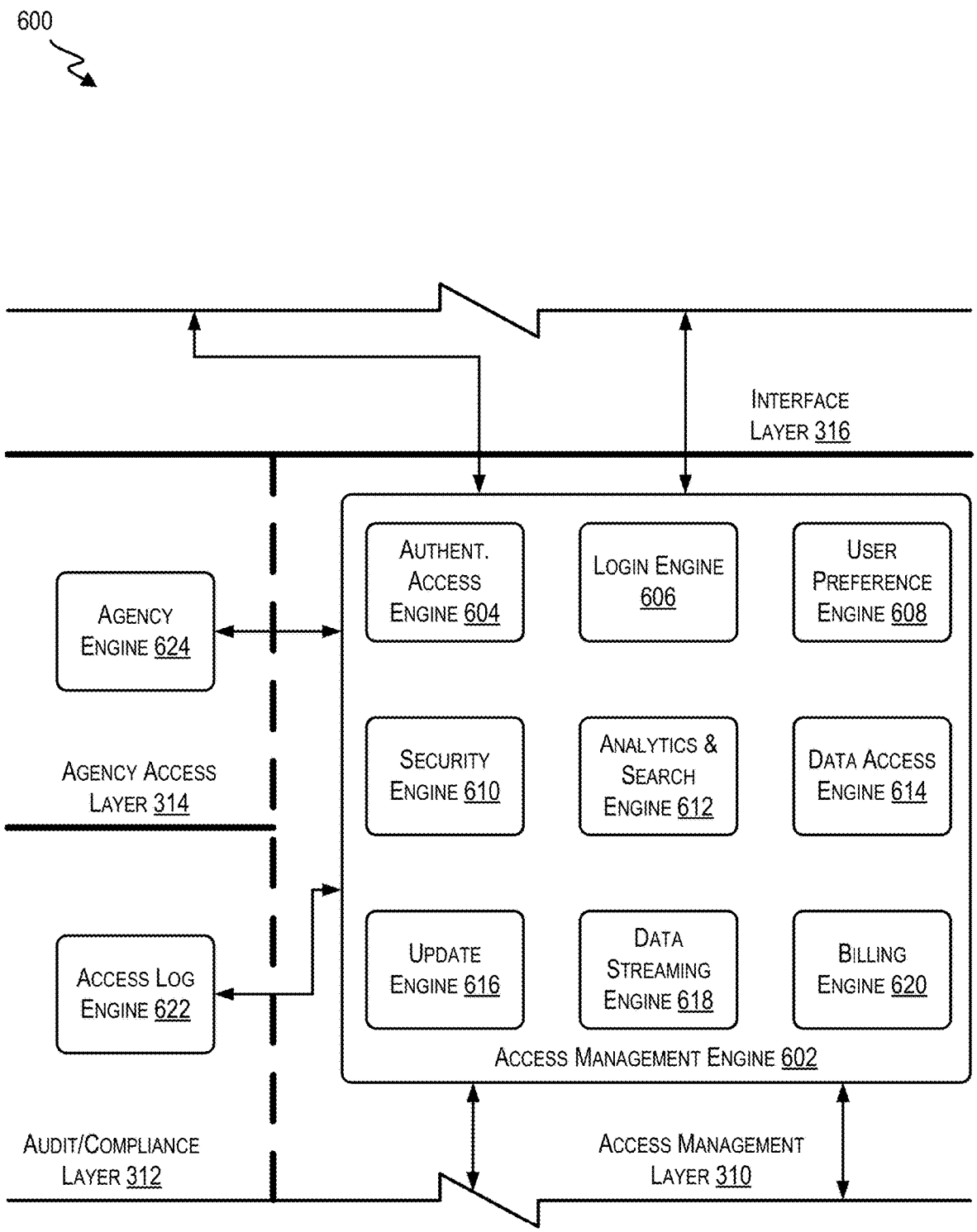
FIG. 6 is an example schematic model illustrating an aspect of the network communication model of FIG. 3 in more detail.

FIG. 6 shows a diagram 600 which depicts a portion of architecture stack 300 according to at least one example. In particular, the diagram 600 includes access management layer 310, audit/compliance layer 312, agency layer 314, and a portion of interface layer 316.

Access management layer 310, as illustrated in the diagram 600, includes an access management engine 602. Access management engine 602 is an example of access management engine 222. Generally, access management engine 602 can be configured to manage access to elements of transformative processing engine 202 by different components, applications, and user devices.

Access management engine 602 within access management layer 310 also provides functionality similar to an operating system. For example, access management engine 602 includes a plurality of engines configured to manage different aspects of interacting with elements of the interaction system. For example, a user who desires to access portions of data retained in data store 508, may do so by interacting with access management engine 602 using one or more applications (not shown). Thus, access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, and a streaming data engine 618. The different engines of access management engine 602 can define routines, protocols, standards, and the like for interacting with elements of the interaction system.

Beginning first with authentication access engine 604, authentication access engine 604 evaluates the rules and conditions under which users may access elements of the interaction system; in particular, the conditions under which users may access data within data store 508. These rules and conditions may be user-defined (e.g., by an administrator or reviewer), learned over time, and/or may be dynamically updated and/or evaluated based on characteristics of the user or the user's device attempting to access the interaction system. The rules and conditions may indicate the types of users who have particular types of access within the interaction system. The type of access may also relate to the degree to which data is identified/de-identified. In some examples, a user desiring access to data provides certain identifying information and authentication access engine 604 authenticates an identity of the user.

Login engine 606 evaluates the rules and conditions under which users are able to log in to the interaction system or access applications associated with the interaction system. These rules and conditions may be user-defined (e.g., by an administrator), learned over time, and also may be dynamically updated and/or evaluated based on characteristics of the user or the user's device attempting to access the interaction system. Thus, while authentication access engine 604 evaluates the rules to determine which users may access the interaction system, login engine 606 evaluates the particular credentials, profiles, etc. of the users. For example, login engine 606 can confirm that an entered username (e.g., and password), provided biometric data or code or identifier in a scanned tag or badge matches that in an authorized user data structure.

Login engine 606 evaluates one or more user profiles associated with each authenticated user. In some examples, a user profile includes a username, password, and other information associated with the user. For example, a user profile may indicate characteristics about the user.

User preference engine 608 evaluates the rules and conditions under which user are able to store and update one or more user preferences corresponding to access of the interaction system or access to applications associated with the interaction system. These rules and conditions may be user-defined (e.g., by the user or administrator), and may include rules for default preferences. For example, using user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

Security engine 610 evaluates the rules and conditions for ensuring the security of access to the elements of the interaction system. In some examples, these rules and conditions are determined by administrators of the interaction system. In some examples, security engine 610 provides a plurality of computer virus protection services. These services can be called up and implemented when accessing the interaction system or accessing applications associated with the interaction system. The rules and conditions may be based on roles, based on profiles, based on domains, and any other suitable security configuration. For example, because the interaction system may include sensitive data, security engine 610 may enforce a domain-based rule that protects certain sensitive information (e.g., identifying information).

Analytics and search engine 612 evaluates the rules and conditions under which users can search for data within the interaction system and access analytics relating to the interaction system. In some examples, these rules and conditions are user-defined or learned over time in accordance with search engine optimization techniques. For example, analytics and search engine 612 is used to search within data store 508 for particular data. Analytics and search engine 612 supports any conventional searching algorithms. For example, search engine 612 can be used to search within various fields and potential field values. In some examples, search engine 612 can provide analytics, such as statistics, graphs, distributions, and/or comparative analysis pertaining to particular entities and/or characteristics. Such information may be selected by a user and presented on a user interface.

Data access engine 614 evaluates the rules and conditions under which users may operation in order to access particular data within data store 508. In some examples, these rules and conditions are user-defined or learned over time. For example, data access engine 614 may indicate the routines, subroutines, or other logic needed for an application to access certain portions of data store 508. For example, while authentication access engine 604 and login engine 606 may manage which users can access parts of the interaction system, data access engine 614 may manage how authenticated users access data within data store 508. To this end, data access engine 614 may enforce and/or evaluate certain rules managing how users access different components of the interaction system. In some examples, data access engine 614 may be used to actually access data within data store 508 (e.g., extract, download, or otherwise access). In some examples, data access engine 614 may define procedures, protocols, and the like for accessing data. The protocols and procedures for accessing data access engine 614 (like the other engines of access management engine 602) may be provided to developers in the form of a software development kit (SDK). SDKs may enable developers write applications that can effectively communicate with elements (e.g., data store 508) of the interaction system. In particular, applications that can access a portion of the data stored within active unified data layer 308.

Update engine 616 evaluates the rules and conditions for providing updates to other engines within access management engine 602, plug-ins for applications that access the interaction system, and for other similar elements of the interaction system. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

Streaming data engine 618 defines the rules and conditions for enabling streaming of data between components and user devices of the interaction system. For example, streaming data engine 618 may enable component 414 to stream data. Streamed data may include live or substantially live audio or video feeds, results of tests, output from equipment or devices, and any other suitable type of data capable of being streamed. In some examples, the data may be streamed to other components or user devices within the network or outside the network. In order to establish a streaming transmission, streaming data engine 618 may identify a streaming destination and a streaming origin. Next, streaming data engine 618 may pair the two and enable streaming. This may include allocated bandwidth within one or more network devices associated with the interaction system. Streaming data engine 618 may also adjust the quality of the streaming data based on the availability of bandwidth. In some examples, streaming data engine 618 may receive incoming streams (and continuously present the stream or monitor for particular data (e.g., exceeding a threshold, exhibiting an above-threshold change, having a particular value)).

Within audit/compliance layer 312 is located an access log engine 622. Access log engine 622 evaluates the rules and conditions for logging access to the interaction system by users, applications, devices, and the like. Logging access includes, in some examples, logging data conventionally collected by access log engines running in similar environments. Access log engine 622 can use this data to generate and transmit reports, for example, to stakeholders of the interaction system such that they can make informed decisions regarding that is accessing the interaction system and for what purposes.

Within agency layer 314 is located an agency engine 624. Agency engine 624 evaluates the rules and conditions under which agencies can access the interaction system. In some examples, agency engine 624 may be used to track one or more performance indicators identified by a government agency and/or to provide report instances of defined types of events. In some examples, a university is an agency that uses agency engine 624 to collect data pertaining to one or more studies. Agency engine 624 can collect the pertinent data, potentially format and/or analyze the data, and facilitate transmission of the data to the appropriate agency.

Figure 7:
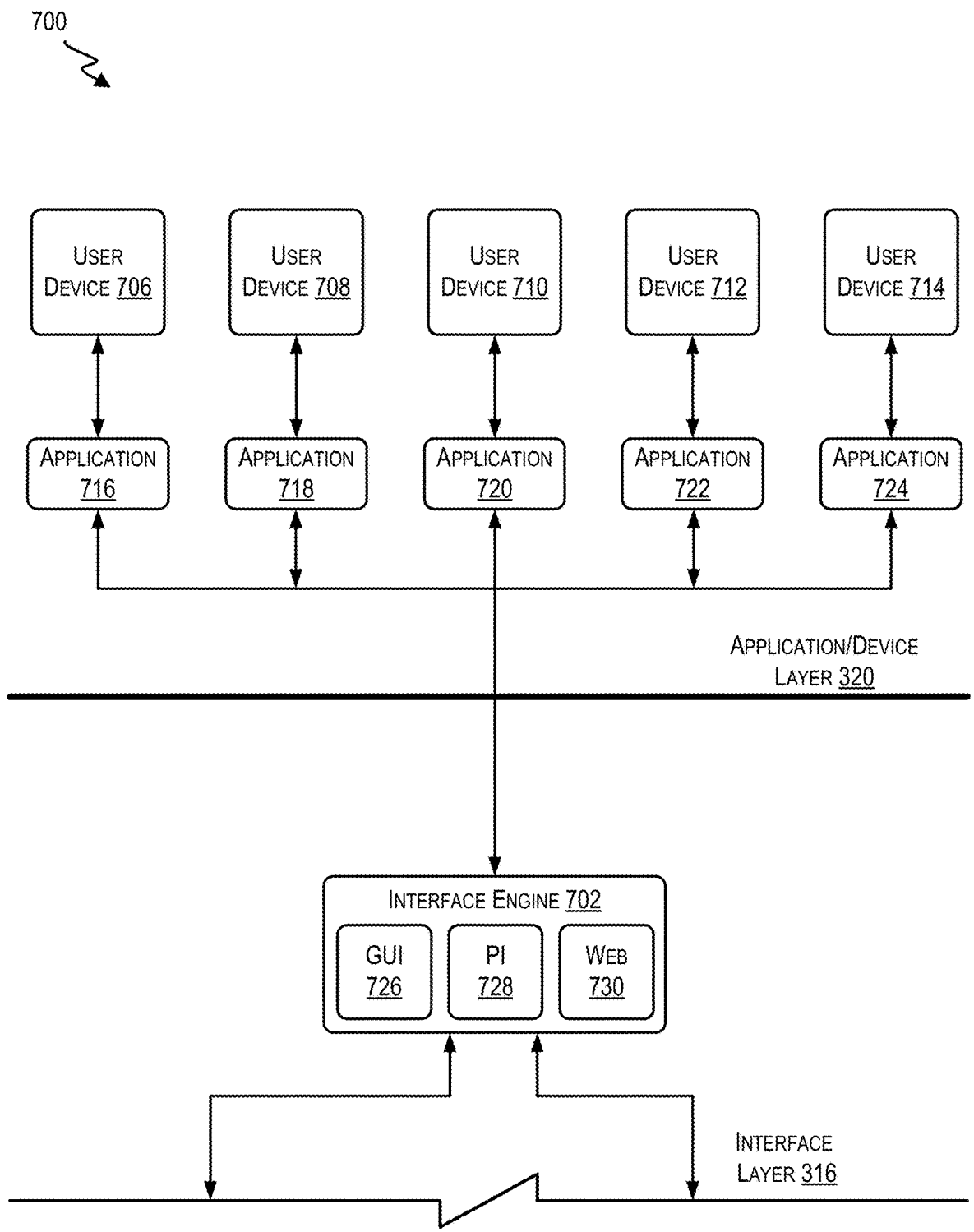
FIG. 7 is an example schematic model illustrating an aspect of the network communication model of FIG. 3 in more detail.

FIG. 7 shows a diagram 700 which depicts a portion of architecture stack 300 according to at least one example. In particular, diagram 700 includes interface layer 316, and application/device layer 320. Within interface layer 316 is located interface engine 702 (e.g., interface engine 224). Interface engine 702 is configured to generate one or more interfaces (e.g., graphical user interface 726, programmatic interface 728, and/or web interface 730) to enable data to flow to user devices 710, 712, and 714 via respective applications 720, 722, and 724. In some examples, the interfaces of interface engine 702 are embodied in hardware, software, or some combination of both. Within interface layer 316 communications and inputs directed to interacting with elements of access management layer 310 may be embodied.

Graphical user interface 726 is any suitable graphical user interface configured to interact with elements of the interaction system. Programmatic interface 728 includes an application programming interface, a programmatic user interface, and other similar interfaces for defining core functions for accessing elements of the interaction system. For example, programmatic interface 728 may specify software components in terms of their operations. Web interface 730 is any suitable web interface configured to interact with elements of the interaction system. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, devices capable of capturing inputs, and the like) operated by one or more users of user devices 706-714. Output may be provided via one or more output devices (e.g., a display or speaker).

Interface engine 702 is utilized by applications internal to the interaction system and external to the interaction system to access data. In some examples, the applications that are internal include applications that are developed for internal use by various entities associated with the interaction system. In some examples, the applications that are external to the interaction system include applications that are developed for external use by those that are not associated with the interaction system.

Generally, within application/device layer 320, applications 716-724 which communicate with other elements of architecture stack 300 using the interfaces generated by interface engine 702 are defined. This includes detailing how applications 716-724 are to interact with the interfaces generated by interface engine 702 for accessing data. For example, interacting may include accepting inputs at user devices 706-714 to access data and, in response, providing the data, prompts, or other types of interaction with one or more users of the user devices 706-714. Thus, applications 716-724 may be related to one or more of the interfaces generated by interface engine 702. For example, application 720 may be interact with a graphical user interface (whether generated by interface engine 702 or otherwise) to interact with other elements of the interaction system. Interacting may include receiving inputs at the graphical user interface via application 720, providing output data to the graphical user interface application 720, enabling interaction with other user devices, other applications, and other elements of the interaction system, and the like. For example, some of the inputs may pertain to aggregation of data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of applications 720, 722, and 724. In some examples, applications 720, 722, and 724 include a variety of different applications that can be designed for particular users and/or uses. In one example, application 720 includes dashboards, widgets, windows, icons, and the like that are customized for a particular entity. In some examples, application 720 may present different data depending on a focus of the entity and protected information associated with the entity. In this manner, application 720 adapts and automatically adjusts depending on the context in which the entity is using the application. Application 720 may be configured to receive input, adjust presentations, present unprompted alerts, adjust display of content, move more relevant content to the foreground, move less relevant content to the background, and/or populate forms for the entity.

In another example, application 722 may be specific for nurses or types of nurses. In this example, application 722 may include dashboards, widgets, windows, icons, and the like that are customized to individual nurses. Similar to the example discussed above pertaining to the user, in some examples, application 724 may present different data depending on a position of the nurse. In this manner, application 722 adapts and automatically adjusts depending on the context in which the nurse is using the application. For example, the nurse may receive data, such as test results.

In some examples, application 724 may be a multi-role application for administrators and is used to manage entities constitute the population of the entities or organizations within the interaction system. Similar to the other examples discussed, in some examples, application 724 may present different data depending on a role of the user who is using application 724. In this manner, application 724 adapts and automatically adjusts depending on characteristics of the user who is using application 724. In this manner, application 724 can provide different data depending on the role of the user. For example, whether data presented includes identifiable or de-identified information may depend on a position of the user.

Applications 716 and 718 shown in connection with interface engine 702 are applications developed by third-parties. In some examples, such applications include any suitable application that benefits from accessing data. The interaction system may include data pertaining to hundreds of thousands of entities. Having data pertaining to so many entities presents security concerns. For example, much of the data may be identifying data. Accordingly, data that may be accessed by applications 716 and 718 may be limited. In some examples, an entity of the interaction system may use one of applications 716, 718 to access his or her own data. In this example, the identity of the entity may be verified in accordance with techniques described herein.

User devices 706-714 are any suitable user devices capable of running applications 716-724. User devices 706-714 are examples of the user device 228. In some examples, the user devices include: mobile phones, tablet computers, laptop computers, wearable mobile devices, desktop computers, set-top boxes, pagers, and other similar user devices. In some examples, at least some of user devices 706-714 are the same devices as at least some of the one or more components 410-418. In some examples, user devices 706-714 may include complementary layers to application/device layer 320 and/or receiving layer 302. For example, user devices 706-714 may include a transmission layer, a generation layer, and/or a receiving layer to communicate data at application/device layer 320 and at receiving layer 302.

Figure 8:
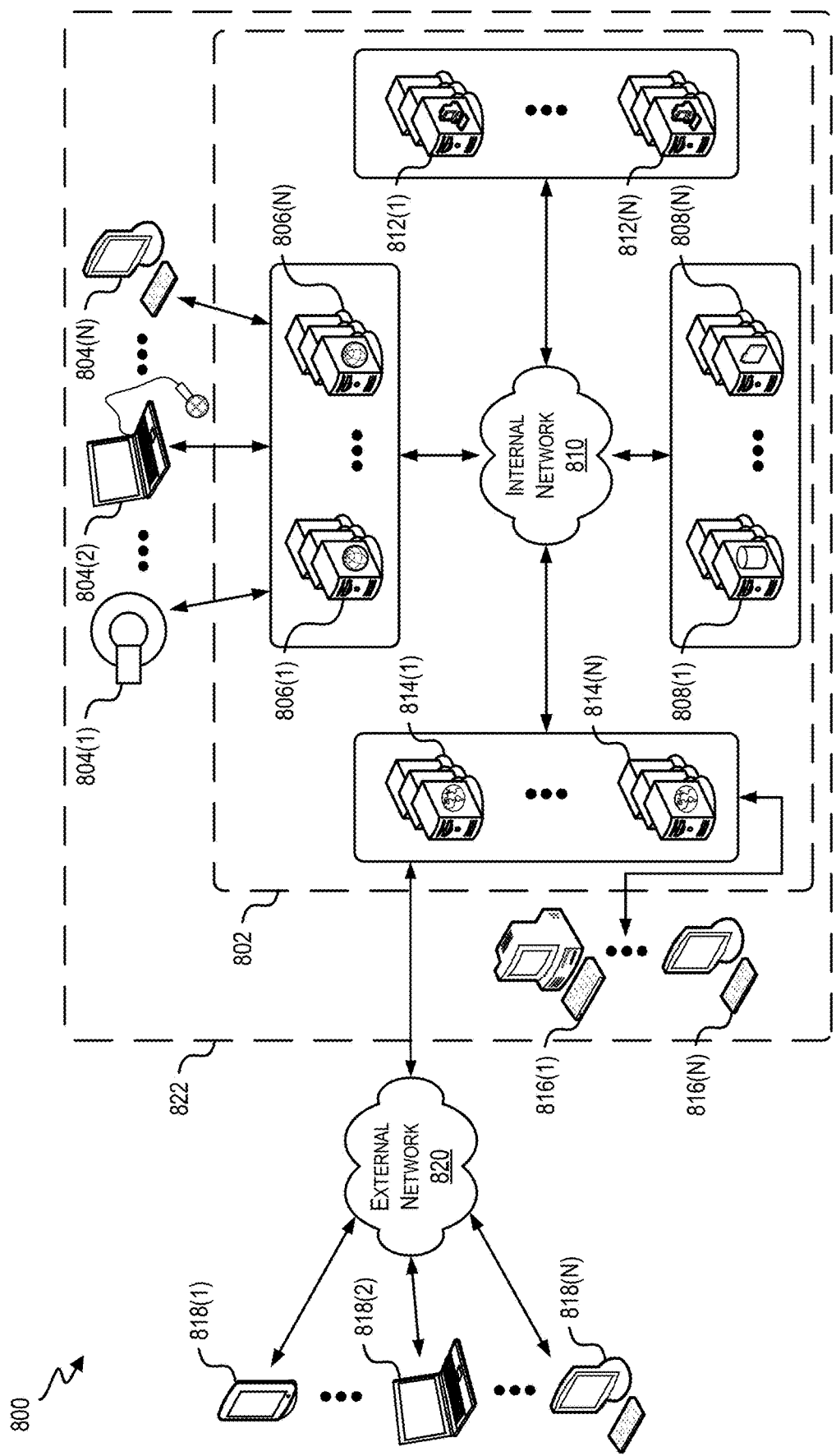
FIG. 8 is an example schematic architecture illustrating an interaction system in which techniques relating to assigning a user to a user navigation program may be implemented, according to at least one example.

Turning now to FIG. 8, an interaction system 800 is shown according to at least one example. Interaction system 800 includes an internal organization 822 including a transformative processing engine 802. The transformative processing engine 802 is an example of transformative processing engine 202 previously discussed. Interaction system 800 is illustrated as an example configuration for implementing the techniques described herein. In particular, a configuration of elements as illustrated in FIG. 8, at least in some examples, communicates according to the layers of architecture stack 300. For example, internal organization 822 includes generation components 804(1), 804(2), and 804(N) which provide data to aggregation servers 806(1)-806(N).

Generation components 804(1), 804(2), and 804(N) operate in accordance with receiving layer 302. In some examples, generation component 804(1) is a piece of equipment, generation component 804(2) is computer with a data collection device, a type of lab system, and generation component 804(N) is a terminal. Aggregation servers 806(1)-806(N) operate in accordance with aggregation layer 304. Aggregation servers 806(1)-806(N) share data with data storage servers 808(1)-808(N) via one or more internal network(s) 810. In some examples, internal network 810 is any suitable network capable of handling transmission of data. For example, internal network 810 may be any suitable combination of wired or wireless networks. In some examples, internal network 810 may include one or more secure networks. Data storage servers 808(1)-808(N) are configured to store data in accordance with active unified data layer 308. Data storage servers 808(1)-808(N) include database servers, file storage servers, and other similar data storage servers.

Access management servers 812(1)-812(N) manage access to the data retained in the data storage servers 808(1)-808(N). Access management servers 812(1)-812(N) communicate with the other elements of interaction system 800 via internal network 810 and in accordance with access management layer 310.

Interface servers 814(1)-814(N) provide one or more interfaces applications to interact with the other elements of interaction system 800. Interface servers 814(1)-814(N) provide the one or more interfaces and communicate with the other elements of interaction system 800 via internal network 810 and in accordance with interface layer 316. The interfaces generated by the interface servers 814(1)-814(N) can be used by internal user devices 816(1)-816(N) and external user devices 818(1), 818(2), and 818(N) to interact with elements of interaction system 800.

Internal user devices 816(1)-816(N) are examples of user devices 706-714. In some examples, internal user devices 816(1)-816(N) run applications via the interfaces generated by interface servers 814(1)-814(N). As an additional example, external user devices 818(1), 818(2), and 818(N) can run applications developed by third parties that access the other elements of interaction system 800 via the interfaces generated by interface servers 814(1)-814(N).

External user devices 818(1), 818(2), and 818(N) access the interfaces via external network 820. In some examples, external network 820 is an unsecured network such as the Internet. External user devices 818(1), 818(2), and 818(N) are examples of user devices 706-714. External user device 818(1) is a mobile device. In some examples, the mobile device may be configured to run an application to access interaction system 800. Similarly, the other external user devices 818(2)-818(N) run applications that enable them to access interaction system 800. While interaction system 800 is shown as implemented using discrete servers, it is understood that it may be implemented using virtual computing resources and/or in a web-based environment.

Figure 9:
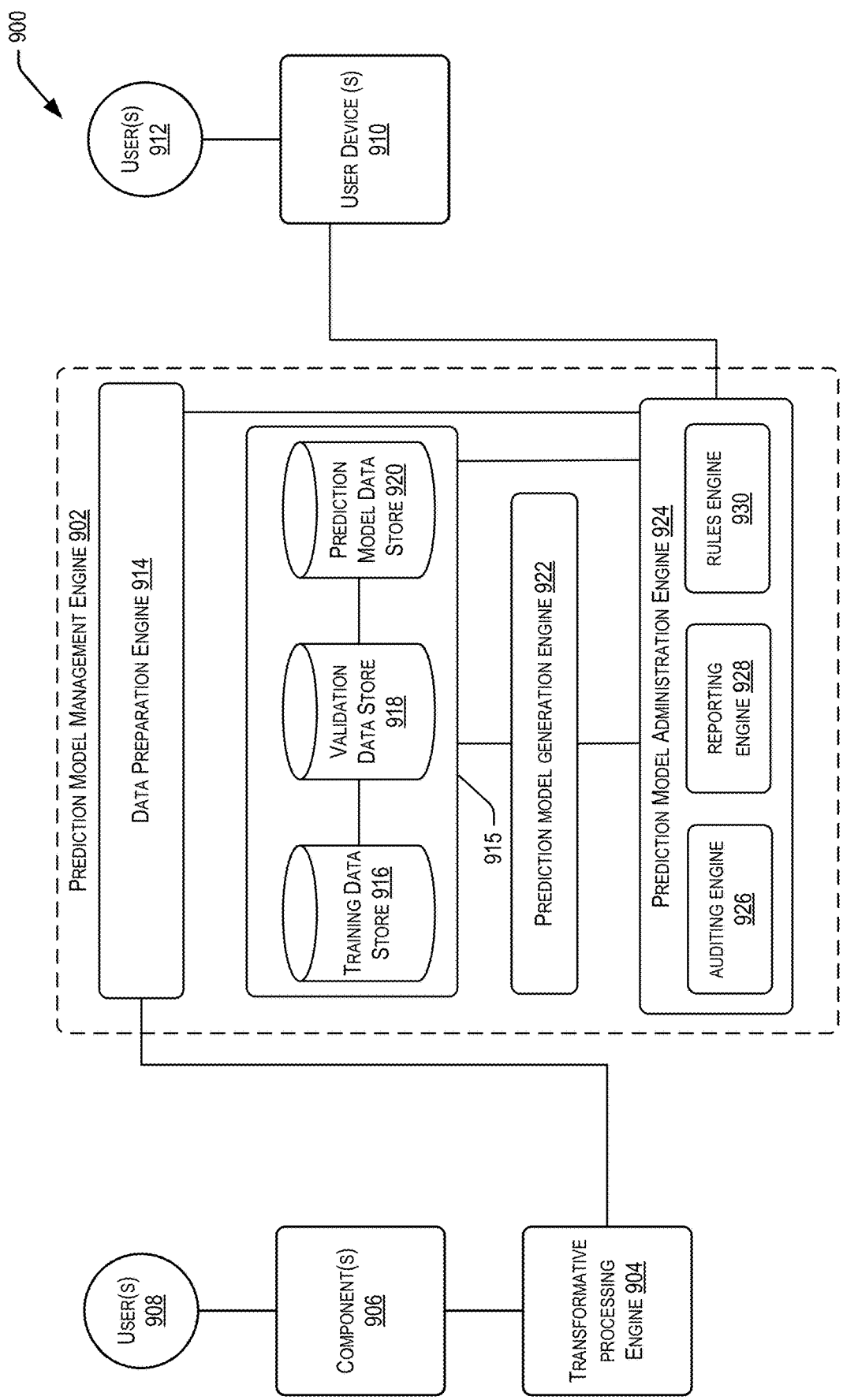
FIG. 9 is an example architecture illustrating a system in which techniques relating to assigning a user to a user navigation program may be implemented, according to at least one example.

Turning now to FIG. 9, a block diagram of an example of a service provider prediction system 900 is shown, according to at least one example. In some examples, the service provider prediction system 900 may be a component of (or connected to) a service management system (e.g., a service provider network) that is affiliated with a service organization. The service organization may include one or more service (e.g., service) facilities, which may each transmit data to the service management system. The service management system, as described in the systems and methods depicted in later figures, may include one or more other components as described in FIGS. 1-8 described herein. For example, the service provider prediction system 900 of FIG. 9 includes a prediction model management engine 902. The service provider prediction system 900 further includes a transformative processing engine 904. The transformative processing engine 904 is an example of the transformative processing engine 108 discussed with reference to FIG. 1. The service provider prediction system 900 also includes one or more generation components 906, which may be similar to the one or more generation components 204 discussed with reference to FIG. 2. In some examples, the generation components 906 may receive data input from one or more users 908 (e.g., clinicians, service technicians, etc.). The service provider prediction system 900 also includes one or more user devices 910 used by users 912 (e.g., USPs such as clinical nurse consultants). The user device(s) 910 may be similar to user device 228 of FIG. 2 and/or user device 104 of FIG. 1. The transformative processing engine 904 and the user device(s) 910 may communicate with the prediction model management engine 902 using any suitable network connectivity device, as described earlier.

In some examples, the transformative processing engine 904 may receive service-related data generated by the generation components 906 (e.g., a lab systems component 208, service equipment component 206, clinical component 212, etc.). The service-related data (e.g., lab results) may be collected from one or more service facilities of a service organization (e.g., from one or more EMR databases respectively associated with different service facilities). The data can further include an identification of a user and/or other user-pertinent information (e.g., user service records, service history, genetic data, biometric data, actual or suspected diagnosis, and/or demographic information). The transformative processing engine 904 may receive the data in any suitable format and may transform the data into a format that is suitable for reception by the prediction model management engine 902. For example, the prediction model management engine 902 may access the transformed data via the interface engine 224 of the transformative processing engine 904. Data may be received by the prediction model management engine 902 using any suitable cadence (e.g., once a day, once an hour, once every minute, every few seconds, etc.). The data may be received (directly or indirectly) via either push or pull technology. In some examples, newly received data may be used to update (e.g., retrain) one or more prediction models of the prediction model management engine 902.

The prediction model management engine 902 includes a data preparation engine 914, a prediction model generation engine 922, a prediction model administration engine 924, and a data store 915. Generally, the data preparation engine 914 is configured to receive and process service-related data from the transformative processing engine 904. In some examples the data preparation engine 914 may prepare (e.g., further transform and/or segment) service-related data so that the data may be used to train and validate a prediction model. For example, a data set of service-related data may be split into different subsets by the data preparation engine 914. A training data subset may be generated that is used to train a particular prediction model (e.g., by adjusting the weights between interconnected nodes of a neural network). In some examples, the same (or similar) training data subset may be used to train one or more prediction models utilizing different algorithms, and then a best model may be chosen. A cross-validation subset may also be generated and used to compare the performances of prediction algorithms that were created based on the training set. The cross-validation subset may be a separate set of data that is held back from training the model, and may be used to minimize over-fitting of data (e.g., verifying that any increase in accuracy achieved over the training data set is not due to over fitting). A test subset (e.g., separate from the training subset and cross-validation subset) may also be used to determine how a particular prediction algorithm will perform on new data. In some examples, any suitable segmenting of data received from the transformative processing engine 904 may be determined by the data preparation engine 914 for training a prediction model.

As discussed further herein, different types of algorithms (e.g., machine learning algorithms, heuristic algorithms, etc.) may be used to generate prediction models. For example, the prediction model management engine 902 may perform supervised or unsupervised learning to generate prediction models. Typically, especially in the case of supervised learning, as part of the training and validation processes, ground truth labels may be created for data samples and included in (or alongside) one or more of the subsets of data determined by the data preparation engine 914. A ground truth label may refer to information that is provided by direct observation, as opposed to information provided by inference. The ground truth label may be used to measure the accuracy of a training data set's classification. For example, a prediction model may be trained to predict whether a user has a particular condition (e.g., cancer). A ground truth label for a particular user may be determined based on an actual observed outcome of the particular user's condition (e.g., a physician confirms that the user has cancer). The training sample for that user may include other data (e.g., blood analysis, biometric data, etc.), which may be used as input to train a prediction model. The prediction that is output by the prediction model may be compared against the ground truth label to determine the accuracy of the prediction, and the comparison results may be used to adjust (e.g., learn) weights and/or parameters of the model accordingly.

In some examples, the data preparation engine 914 may perform semantic tagging and indexing of service-related data (e.g., categorizing data). The data preparation engine 914 may also determine if gaps exist in the pool of data samples, whereby new data should be obtained to increase training coverage. For example, some users' service records may omit an attribute (e.g., Body Mass Index (BMI)) which may be determined to be an important feature for training a particular prediction model. In this case, the data preparation engine 914 may tag these records as requiring attention and transmit a notification to a user device of a system administrator for further action. The data preparation engine 914 may also perform feature engineering, which may involve further transforming and/or extracting the data into a different form that is suitable for training a particular prediction model. For example, the data preparation engine 914 may receive raw data corresponding to pixels of an image (e.g., of a portion of a user's body). The data preparation engine 914 may then perform one or more operations to analyze the pixels of the image to generate a new feature from the raw data (e.g., a level of skin redness). This new feature may then be used as one of the inputs to a machine learning algorithm (e.g., predicting a type of condition). It should be understood that, in some cases, the data preparation engine 914 may execute a previously generated prediction model in order to engineer a feature that may in turn be used to train another prediction model.

From the data preparation engine 914, data may flow to the data store 915. The data store (and any other data store discussed herein) may include one or more data stores, which may be distributed throughout two or more different locations (e.g., present on different devices, which can include devices of different entities and/or a cloud server). In some examples, the data store 915 includes a training data store 916, a validation data store 918, and a prediction model data store 920. Within each of the data stores 916, 918, and 920 is stored prediction model-related data. In some examples, the structure of one or more of the data stores 916, 918, or 920 may be similar to data store 226. The training data store 916 may contain training data that is used to train a prediction model. The training data may include multiple samples (e.g., based on user service records), and may include ground truth data for each sample. Different sets of training data may be created from the multiple samples (e.g., generating a new training data set on a predetermined time interval). The different training data sets may also be training data subsets that are randomly generated from an overall pool of training data samples, so as to reduce the risk of overfitting. The validation data store 918 may contain training data that is used to validate a prediction model. For example, the validation data store 918 may contain cross-validation and/or test data subsets that are generated from the pool of training data samples. The training data stored in the validation data store 918 may be determined and further curated based at least in part on the composition of the training data sets in the training data store (e.g., generating disjoint sets of data for increased accuracy during validation and testing). The prediction model data store 920 may contain one or more prediction models, which may be either trained or untrained prediction models. The trained prediction models may be generated from the prediction model generation engine 922, discussed further below. The prediction model data store 920 may further include parameters that may be used to train (or update) a prediction model. As a non-limiting example, this may include a type of loss function, a learning rate (e.g., how much to adjust data weights after each training iteration), a subsample size (e.g., indicating how many training samples should be used to train a new model), a number of nodes (e.g., in the case of a neural network), a number of leaves/levels (e.g., in the case of a decision tree), a number of trees (e.g., in the case of a boosted decision tree model), etc.

The prediction model generation engine 922 is configured to generate one or more trained prediction models based at least in part on data from the data store 915. A trained prediction model may be trained to identify which set of one or more categories a new observation (e.g., data from user's service record) belongs. In the case of supervised learning, this may be based on the training set of data containing observations whose category membership is known (e.g., a user who is known to have a particular cancer, which observation may be recorded as a ground truth label). In the case of unsupervised learning, this may be based on grouping data into categories based on some measure of inherent similarity or distance (e.g., clustering). In either type of learning, a trained prediction model may classify an observation as a binary classification (e.g., patent has or does not have an injury) or a multiclass classification (e.g., user has a particular type injury of several possible injury types). In some examples, a trained prediction model may use observation data to output one or more classifications (e.g., assessments) about one or more respective aspects regarding a user's condition (e.g., a likelihood of injury, a type of injury, a severity of injury, etc.). Each of these one or more classifications may be either binary or multiclass classifications. The classifications may include one or more values (e.g., a binary value, or a real number (between 0-1)) that indicate a likelihood of a particular classification being an accurate assessment.

The prediction model generation engine 922 may utilize one or more artificial intelligence techniques to generate a prediction model. As used herein, the term "artificial intelligence" (AI) refers to any suitable computer-implemented artificial intelligence technique including, but not limited to, machine learning (ML) (supervised or unsupervised), natural language processing, machine perception, computer vision, affective computing, statistical learning and classification, Bayesian network models and Kalman filters, reinforcement learning including neural networks, search algorithms and optimization algorithms (including evolutionary computing), heuristic-based algorithms, and automated reasoning. Non-limiting examples of classification algorithms include use of hidden Markov models, decision trees (e.g., boosting decision trees, random forests), support vector machines, etc.

The prediction model administration engine 924 may be utilized to configure the prediction model management engine 902. In some examples, the prediction model administration engine 924 may include an auditing engine 926, a reporting engine 928, and a rules engine 930. The auditing engine 926 may include elements for tracking and monitoring the performance of a prediction model. For example, the auditing engine 926 may be configured (e.g., by a user device 910) to monitor precision and recall values (and/or sensitivity, specificity, F1 values) for a prediction model over time, as new data is received and input into the prediction model. The reporting engine 928 may include elements for generating one or more reports that are consumable by a user 912 via a user device 910. For example, the reporting engine 928 may execute one or more trained prediction models to generate a report for a one or more users. The report may indicate, for each user, a predicted classification of the user based on current user data (e.g., whether the user has a particular condition or not). The report may include other information (e.g., user demographics, user admission data, etc.), which may assist a user service coordinator in determining a course of service for the user. The reports engine 928 may also output reports on a periodic basis that indicate the performance of one or more prediction models, which may be used to determine whether a model should be retrained with updated data. The rules engine 930 may determine one or more rules for managing aspects of the prediction model management engine. For example, the rules engine 930 may receive input from a user device 910 that is used to configure the data preparation engine (e.g., add a new feature to the list of predictive features being tagged). The rules engine 930 may also be used to configure aspects of the data store 915 (e.g., controls for determining which data should be grouped into a training subset versus a test and/or cross-validation subset, how large a training sample subset should be, etc.). The rules engine 930 may also be used to configure aspects of the prediction model generation engine 922. For example, the rules engine 930 may receive input indicating when a new prediction model should be generated (e.g., on a predetermined cadence, using one or more ML algorithms with particular parameters, etc.). The rules engine 903 may also be used to determine one or more heuristics that may be used as input to the prediction model generation engine 922. For example, one heuristic may indicate that if a user has previously missed more than one scheduled appointment, then they may be more likely to miss future appointments (e.g., and thus may be a good candidate for receiving a reminder call from a USP about future appointments). The heuristics may be determined by a human (e.g., a USP) and input into the rules engine 930, or may be determined automatically (e.g., by the prediction model generation engine 922). For example, the prediction model generation engine 922 may be trained to recognize patterns and make inferences based on those patterns (e.g., if a person misses more than three appointments, they are highly likely to miss future appointments). These inferences may be formulated into rules used to generate a prediction model.

Figure 10:
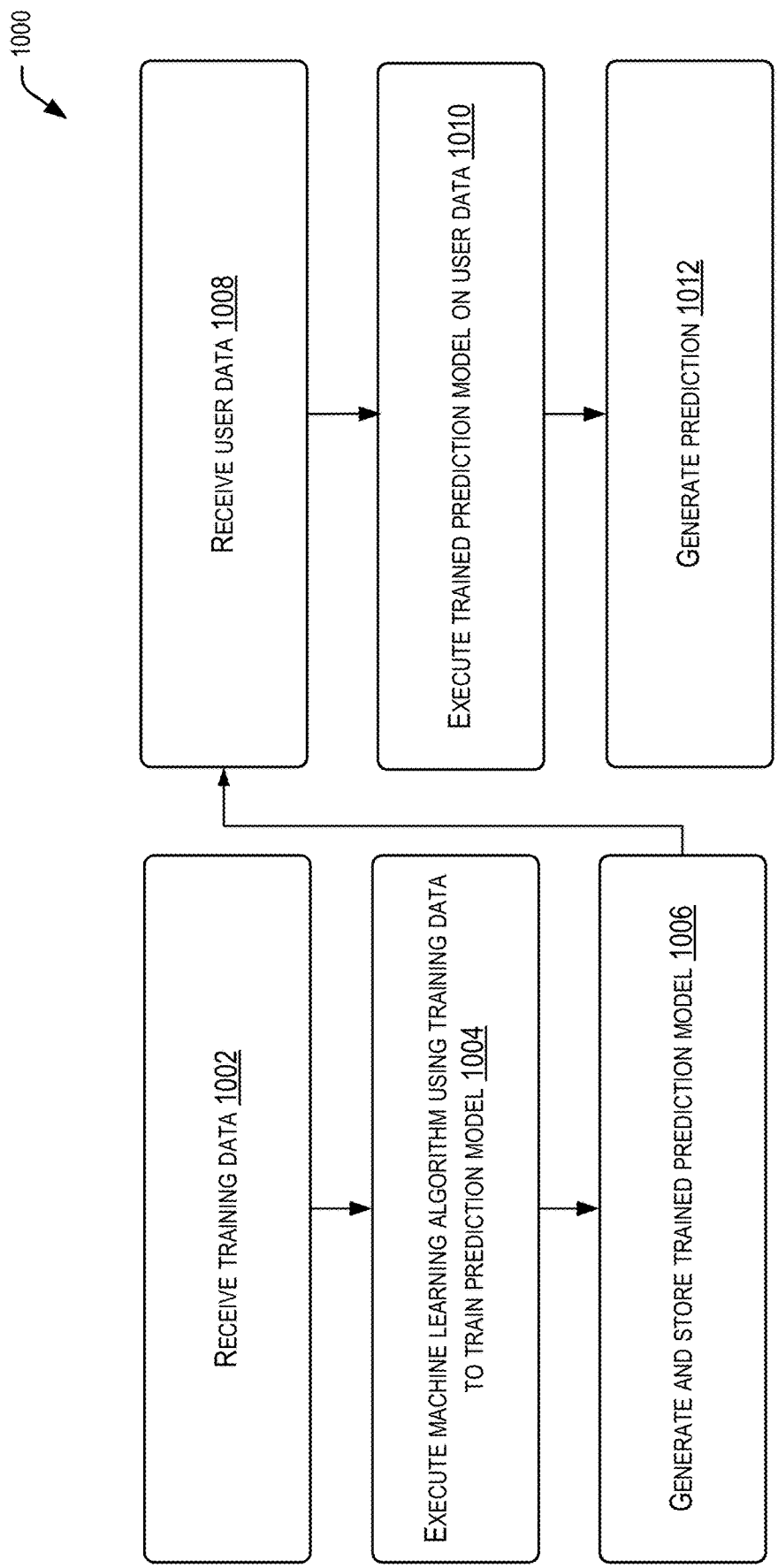
FIG. 10 is an example flowchart illustrating a process for assigning a user to a user navigation program, according to at least one example.

Turning to FIG. 10, an example flow diagram 1000 is depicted for a computer system training a prediction model and executing the trained prediction model. The flow diagram may proceed in two phases: a training phase (blocks 1002-1006) and an execution phase that follows the training phase (blocks 1008-1012). In some embodiments, the computer system that performs the process 1000 may correspond to the service provider prediction system 900 of FIG. 9.

Some or all of the flow 1000 (or any other processes described herein, or variations, and/or combinations thereof) may be performed under the control of one or more computer systems configured with executable instructions and may be implemented as code (e.g., executable instructions, one or more computer programs, or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Additionally, these processes are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

The example flow 1000 may start at block 1002, whereby the system may receive training data. In some examples, the training data may be generated from one or more generation components 204 (e.g., lab systems, clinical components, etc.). In some examples, the one or more generation components 204 may belong to different service providers (e.g., different service facilities) within a service organization. In some examples, the training data may be received from other sources outside the service organization (e.g., third party entities, government organizations). The training data may be associated with and/or derived from user data of users, for example, derived from user electronic service records. In some examples, a training data sample of the training data may include a plurality of data points that identify characteristics of a user, diagnoses made by service providers, associated service plans for the user made by the providers, associated outcomes of the user based on those service plans, health indicators for the user, laboratory test results (e.g., from blood, urine, and/or other tests), a service status of the user (e.g., recently discharged, completed round three of chemotherapy service, recently was administered a particular medication, etc.), and other suitable information. In some examples, the training data may indicate not only historical service data, corresponding to previous admissions of the user, but may also include present admission data, corresponding to a present admission of the user for a condition. The user data may be received in any suitable form, including structured and/or unstructured user data. Structured data may be data that is organized and formatted in a way that is directly searchable (e.g., in a relational database). Examples of structured user data may include user service records, test results, chart information, etc. Unstructured data may have no (or limited) pre-defined format or organization. Examples of unstructured data may include a clinician's notes, service images, user feedback/correspondence, etc. In general, both structured and unstructured data may be formatted in any suitable way, including, but not limited to, text, audio, video, digital images, and numerical values. The training data may be processed and/or transformed into a suitable form for training a prediction model, for example, by data preparation engine 914. In some examples, this may involve semantically tagging the data, segmenting the data into different subsets (e.g., training sets, cross-validation subsets, testing subsets, etc.), performing feature engineering to generate one or more features for training the prediction model, etc. The training data may be stored in a data store (e.g., data store 915) for future use in training a prediction model.

At block 1004, the system may execute a machine learning algorithm using the training data to train a prediction model. Any suitable machine learning algorithm may be used to train the prediction model, including supervised learning algorithms (e.g., logistic regressions, neural networks), unsupervised learning algorithms (e.g., K-means, Apriori algorithm), and/or reinforcement learning algorithms (e.g., Markov decision processes).

In a first non-limiting example of a supervised learning algorithm, a neural network machine learning algorithm may be used to generate a prediction model using a set of inputs (e.g., training data) that includes one or more features, which in some cases may be measurable properties derived from user data (e.g., blood cell count, blood pressure, age, etc.). Any suitable number of features may be used as input to generate the prediction model. Using this technique, the set of inputs may be used as an input layer and the set of outputs may be used as an output layer. In this technique, the input layer may be connected to the output layer via one or more hidden layers. Each layer may include a set of one or more nodes, whereby each node may represent a piece of information. The generated prediction model may include a number of interconnections between the hidden layers and the input layer and/or output layer (e.g., between nodes of the different layers), each of which may be assigned a numeric weight generated based on a pattern identified between the set of input values and the set of output values. The weight may be tuned (e.g., based on a training dataset), rendering the artificial neural network adaptive to inputs and capable of learning. Generally, the hidden layer(s) allows knowledge about the input nodes of the input layer to be shared among the output nodes of the output layer. To do so, a transformation f is applied to the input nodes through the hidden layer. The artificial neural network may also use a cost function to find an optimal solution (e.g., an optimal transformation function). The optimal solution represents the situation where no solution has a cost less than the cost of the optimal solution. In an example, the cost function includes a mean-squared error function that minimizes the average squared error between an output f (x) (e.g., a prediction, given training data input x) and a target value y (e.g., a ground truth value) over the example pairs (x, y). In some embodiments, a backpropagation algorithm that uses gradient descent to minimize the cost function may be used to train the artificial neural network. In this example, one or more parameters (e.g., which also may be known as "hyper-parameters") may be used to administer the training process. For example, these parameters may include determining how many hidden layers of nodes to use between the input layer and the output layer, and how many nodes each layer should use. In this example, the collection of nodes and determined weights (e.g., based on training data) between interconnections of nodes between the different layers may form the trained model. Once the artificial neural network (i.e., prediction model) has been generated, it may be used to predict one or more events (e.g., regarding a user's present and/or future condition) upon receiving input (e.g. user data).

In a second non-limiting example, a boosted decision tree technique may be used to generate a prediction model using a set of inputs (e.g., training data) that includes one or more features. Each feature may directly correspond a data point (e.g., BMI, blood pressure, etc.), or be derived from one or more data points, similar to as described earlier. This technique is also a supervised learning method and may utilize a labeled dataset with ground truth data. A pre-trained decision tree may receive a set of input features as input and then split the input data based on those features. For example, a given node in a decision tree may split (e.g., determine an outcome) based on the respective values of one or more input features input to the given node. The selection at each node of what is the next best feature to split on may be performed based at least in part on determining which features maximize information gain and/or to minimize entropy, and may be chosen as part of a (e.g., recursive)

learning/training process used to generate the decision tree. The process may be repeated until a stop condition is met (e.g., the process reaches the depth of the tree, no more information gain, etc.). Terminal nodes of the decision tree may represent a class (e.g., segment) label (e.g., the user has a particular condition) or probability (e.g., probability that user has a particular condition), which may correspond to a prediction outcome. In some examples, the outcome may be a continuous variable.

Using a boosted decision tree technique, multiple weak learners (e.g., an ensemble of decision trees) may be combined into a strong classifier. In some examples, each new decision tree may be created iteratively with respect to a distribution (e.g., associated with ground truth data from a training data set), and new trees may be generated based at least in part on previous trees. On each iteration, the new tree's prediction from a data sample may be given a weight relative to its accuracy. In some examples, the ensemble output (from the multiple trees) may be a weighted sum that may be compared against the ground truth. Additionally, after each iteration, each data sample (e.g., including one or more features from the data sample) may also be given a weight based the decision tree's misclassification. In this way, the more often a data sample is misclassified, the more important the data sample (and/or individual features of the data sample) becomes. The process of training the ensemble of decision trees that collectively predict an outcome (i.e., "boosting") may also include minimizing a cost function, which, similar to above, may include a function that measures the distance between the ground truth (y) and an output f(x) (e.g., to minimize the mean-squared error).

Based at least in part on the relative weight of the output of each decision tree in an ensemble and/or the relative weights of data samples, the system may be able to determine a relative importance of features among the set of features that are represented in the ensemble of decision trees (e.g., represented by the positioning of each node within a respective decision tree and the splitting behavior assigned to the node). In some examples, the relative importance among features may represent which feature is likely to result in the most information gain among other features. The system may also be able to determine, based at least in part on the splits determined for each node in the ensemble of trees, classifier decision boundaries. A classifier decision boundary is a decision boundary that partitions an underlying vector space into two sets (e.g., user has the condition, or the user does not have the condition). In some examples, a classifier decision boundary may be determined by an ensemble of classifiers (e.g., a boosted decision tree model) based at least in part on respective values (e.g., a range of values) for one or more features of the plurality of features that are input into the model. In a simplified example, one feature may be age, and another feature may be BMI of a user. For a particular condition, the model may determine that for an age range of 60 years old or more, and a BMI range 15-17, a user would be classified as having a particular condition. In some examples, multiple classifier decision boundaries may be determined from a boosted decision tree model, which may be collectively used as input to determine a final prediction. For example, one classifier decision boundary may determine, from one set of features, that the user is likely to have a condition with a first probability. Another classifier decision boundary may determine, from another set of features, that the user is likely to have (or not have) the condition with a second probability. The first and second probabilities may be combined together to determine a final probability (e.g., prediction). In some examples, this combining process may be represented within the trained boosted decision tree model using ensemble modeling. Similar to the neural network example, one or more parameters may be used to administer the training process. For example, these parameters may include determining a maximum depth of a tree, a maximum number of leaves, a maximum number of features (e.g., from the full set of features) that may be used to build a given tree, a minimum number of samples required to make a new leaf, etc.). Once the (boosted) decision tree prediction model has been generated, it may be used to predict one or more events (e.g., regarding a user's present and/or future condition).

While two possible examples of prediction models were mentioned above, it should be understood that any suitable prediction model may be utilized. Typically, the system will receive training data (e.g., user data received from the service organization) that is used to train the prediction model by learning characteristics (e.g., patterns and/or relationships, for example via heuristic algorithms) from the training data and thereby determining properties (e.g., weights) of the model. The system may also determine one or more parameters that may be used in training the model, whereby the parameters may be determined based on the type (e.g., structure) of model chosen (e.g., neural network, decision tree, linear regression, naive Bayes, etc.). In some examples, one or more prediction models may be chained together using an ensemble modeling to obtain better predictive performance. Additionally, in some examples, the output of one prediction model may be used as an input (e.g., as a feature) to another predictive model. For example, a first prediction model may be a neural network that predicts and/or classifies a type of skin injury. The output of the first prediction model may be used as a feature input to a second prediction model (e.g., a boosted decision tree model) that may predict a particular stage of the skin injury with a certain probability.

At block 1006, the system may generate and store the trained prediction model 1006. The generated prediction model may include any suitable data structures utilized from block 1004 to train the prediction model, as well as learned information during the training process (e.g., a meaning assigned to a node, a position of the node within the model, a weight value for a node, etc.). In some examples, the parameters used to train the given prediction model may also be stored, for example, to be later used in updating the model. For example, the prediction model administration engine 924 may perform an audit of the prediction model, and, based on the results of the audit, determine that one or more parameters used to train the model should be adjusted (e.g., increasing the maximum number of leaves). The trained prediction model may be stored in the prediction model store 920.

At block 1008, at a later time following the generation/ storage of the prediction model at block 1006, the system may receive user data (e.g., including structured or unstructured user data) for use in generating a prediction about a user (e.g., for classifying (or "segmenting") the user). In some examples, the user data may correspond to current information about a particular user (e.g., service records for a present admission to a service facility). Similar to the training data, the user data may also include a plurality of data points that identify characteristics of the particular user. In this case, however, instead of the data being used to train a prediction model, it will be used as input into the already-trained prediction model for use in generating a prediction about the condition of the user (e.g., for the present admission). In some examples, one or more of the plurality of data points of the user data may correspond to (and/or be used to derive) features by which the prediction model was trained to make predictions.

At block 1010, the system may execute the trained prediction model on the received user data. As described earlier, the system may use the user data for the particular user to extract features that are used as input to the prediction model (e.g., to an input layer of a neural network, root node of a decision tree, etc.).

At block 1012, the system may execute the trained prediction model to generate a prediction about the user (e.g., classifying the user as having a particular condition or service status). In some examples, the prediction may correspond to an assessment about a present condition or potential future condition (or service status) of the user. In some examples, the assessment may include data associated with a plurality of conditions of the user (e.g., multiple injuries on the body). In the case where the prediction corresponds to an assessment about a present condition, the prediction may indicate a likelihood that the user has a particular present condition. In the case where the prediction corresponds to an assessment about a potential future condition, the prediction may indicate a likelihood that the user will develop the potential future condition. As a non-limiting example, a potential future condition may correspond to the existence an illness affecting the user, a severity and/or stage of the illness, a likelihood that another related illness or condition may develop, etc. In some examples, the prediction may correspond to a probability score (e.g., between 0-1). In some examples, the prediction may correspond to a classification of a likely group to which the user belongs (e.g., Stage 1, Stage 2, Stage 3, etc.). For example, the prediction may include a plurality of probabilities that respectively correspond to a likelihood of the user's illness being at a particular stage (e.g., Stage 1=0.23, Stage 2=0.64, Stage 3=0.13). As referenced herein, depending on the context, a "prediction" may be used interchangeably with a "probability score." In some examples, the prediction may be classified based on whether or not a probability score included within the prediction matches (e.g., equals or exceeds) a predefined threshold value. For example, a user with a probability score of at least 80% may be deemed to be "High Risk." In another example, a user with a probability score of at least 80% may be determined to be classified with a particular condition with high confidence. This classification based at least in part on the predefined threshold value may be built into the trained prediction model (e.g., part of the training process), or may be a separate computation that follows the prediction model outputting one or more scores. In some examples, the trained prediction model may output different probability scores respectively for varying degrees of specificity for a particular condition. For example, the trained prediction model may output a score of 85% that corresponds to a confidence level that the user has "cancer." The model may further output a score of 70% that the corresponds to a confidence level that the user has "breast cancer." The model may further output a score of 55% that corresponds to a confidence level that the user has "stage 3 breast cancer." As updated user data is received by the trained prediction model, the respective scores may be updated accordingly.

The systems, processes, and models described with reference to FIGS. 1-10 may be used to implement the techniques described herein with reference to later figures. For example, data communication may be performed within the aggregation layer 304 or the active unified data layer 308. In some examples, messages originate at one of the components 410-418 (e.g., generation components 204) and are streamed to the data store 508. These messages may be intercepted by the collection engine 504 or any other suitable interceptor device and shared with the user navigation (UN) system described herein.

Figure 11:
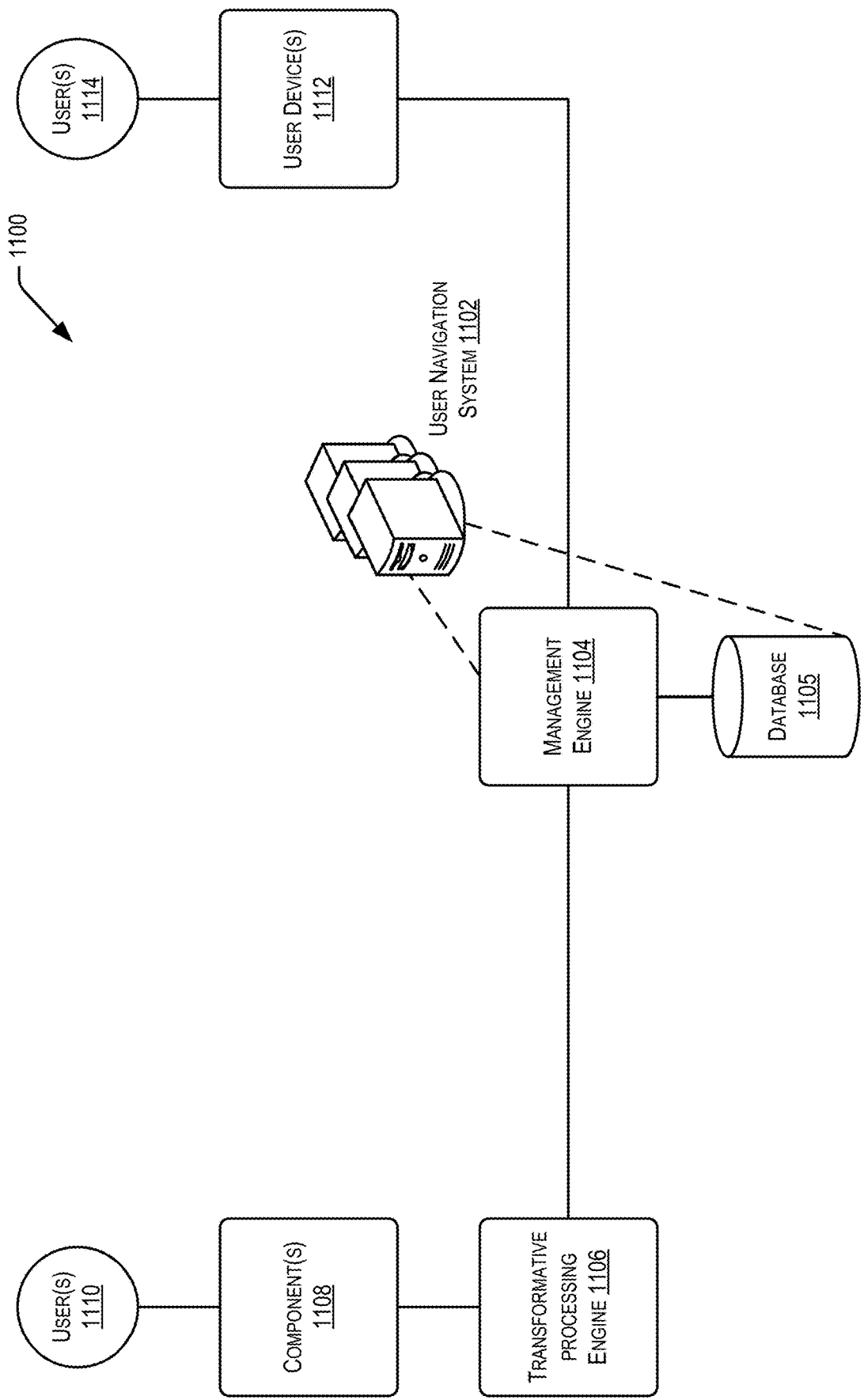
FIG. 11 is an example architecture illustrating a system in which techniques relating to assigning a user to a user navigation program may be implemented, according to at least one example.

Turning now to FIG. 11, a user navigation (UN) architecture 1100 is shown, in accordance with at least one example. The UN architecture 1100 may be implemented using elements of the systems, networks, and models of FIGS. 1-10. For example, the UN architecture 1100 may include similar elements as service provider prediction system 900 of FIG. 9. For example, the UN architecture 1100 may include a UN system 1102, which includes a management engine 1104 (e.g., prediction model management engine 902) and a database 1105 (e.g., included within data store 915). The UN architecture 1100 may further include a transformative processing engine 1106 (e.g., similar to transformative processing engine 202 of FIG. 2). The transformative processing engine 1106 may be configured to receive and process data from one or more generation components 1108 (e.g., similar to generation components 204 of FIG. 2), which may in turn receive input from one or more generation users 1110 (e.g., user service providers (USPs), users, and/or other service professionals) to generate service-related data. The UN architecture 1100 may further include one or more user devices 1112 (e.g., similar to user device 228), which may be used to interact with users 1114 (e.g., USPs and/or other service professionals).

In some examples, the UN system 1102 may be configured to receive data from the transformative processing engine 1106 and utilize the data to generate one or more predictions (e.g., a user "classification" (also referred to as a "segmentation")). In some examples, these predictions may be used as input for further action/analysis by the UN system 1102 (e.g., facilitating a user navigation process). The transformative processing engine 1106, described in detail herein, can process and store data used by a UN system 1102 to implement the techniques described herein. For example, the management engine 1104 of the UN system 1102 may receive user data from the transformative processing engine 1106 and use the user data to train one or more prediction models. The user data may include user service records, interaction data (e.g., between the user and a USP), feedback data, outcome data, and the like. The user data may be representative of users within a population. At a later time, the management engine 1104 may receive current user data (e.g., for a currently admitted user) which is input into one of the trained prediction models. The trained prediction model may then output a prediction (e.g., a score for a user corresponding to a level of confidence of a classification of the user). The UN system 1102 may further analyze the prediction to determine, for example, if the user should be assigned to a particular user navigation program. In some examples, the predictions (and/or the resulting analysis based on the predictions) may be displayed on a user device 1112 of a user 1114.

The database 1105 is accessible by the management engine 1104, and may be similar to (or connected to) data store 915 of FIG. 9 and/or data store 226 of FIG. 2. The database 1105 may access user data from a transformative processing engine 1106, and the management engine 1104 may use such data to generate a score for a user. For example, the user data may include training data and testing data (e.g., to test the prediction models). The database 1105 can be distributed or otherwise made available to multiple users. In some examples, the database 1105 may be centralized. In other examples, the database 1105 may be decentralized (e.g., a database per division or per service facility). In some examples, the database 1105 may store multiple prediction models. It should be understood that, although in the embodiments described herein, multiple types of prediction models may be described, the functions performed by the one or more prediction models may also be performed within a single prediction model or any suitable combination of models, as described with reference to FIGS. 9 and 10. The prediction models, as described herein, can be initialized using data mined from the data store of the transformative processing engine 1106.

The UN system 1102 may be affiliated with a service management system of a service organization (e.g., enterprise), whereby the service management system may also be implemented using similar elements of the systems, networks, and models of FIGS. 1-10. For example, the service management system may be a centralized system for performing techniques described herein. The centralized system may aggregate user data (e.g., via the transformative processing engine 1106) from a plurality of affiliated service facilities of the service organization into a data store (e.g., data store 226) for further processing by the UN system 1102. For example, individual service facilities of the plurality of affiliated service facilities of the service organization may, respectively, be associated with one or more data stores (e.g., EMRs, emergency department discharge systems, etc.). User data from one or more of these data stores may be aggregated and processed by the centralized system.

Examples described herein provide different systems and methods for supporting a USP (e.g., a nurse, user navigator, user navigation coordinator, physician, administrator, service facility executive) in the process of coordinating user service. The systems and methods provided are suitable to support a USP in a variety of environments and contexts. For example, some environments may involve coordinating user service across an entire enterprise or a division of the enterprise that contains multiple service facilities. Another environment involves coordinating service among users in a single service facility, and/or users within a particular department within the single service facility. In another example of a particular context, the system may help the USP coordinate service for a user at the time of admission to a service facility, while the user is receiving service during their stay, or post-discharge. These various environments and contexts will be discussed herein below.

Figure 12:
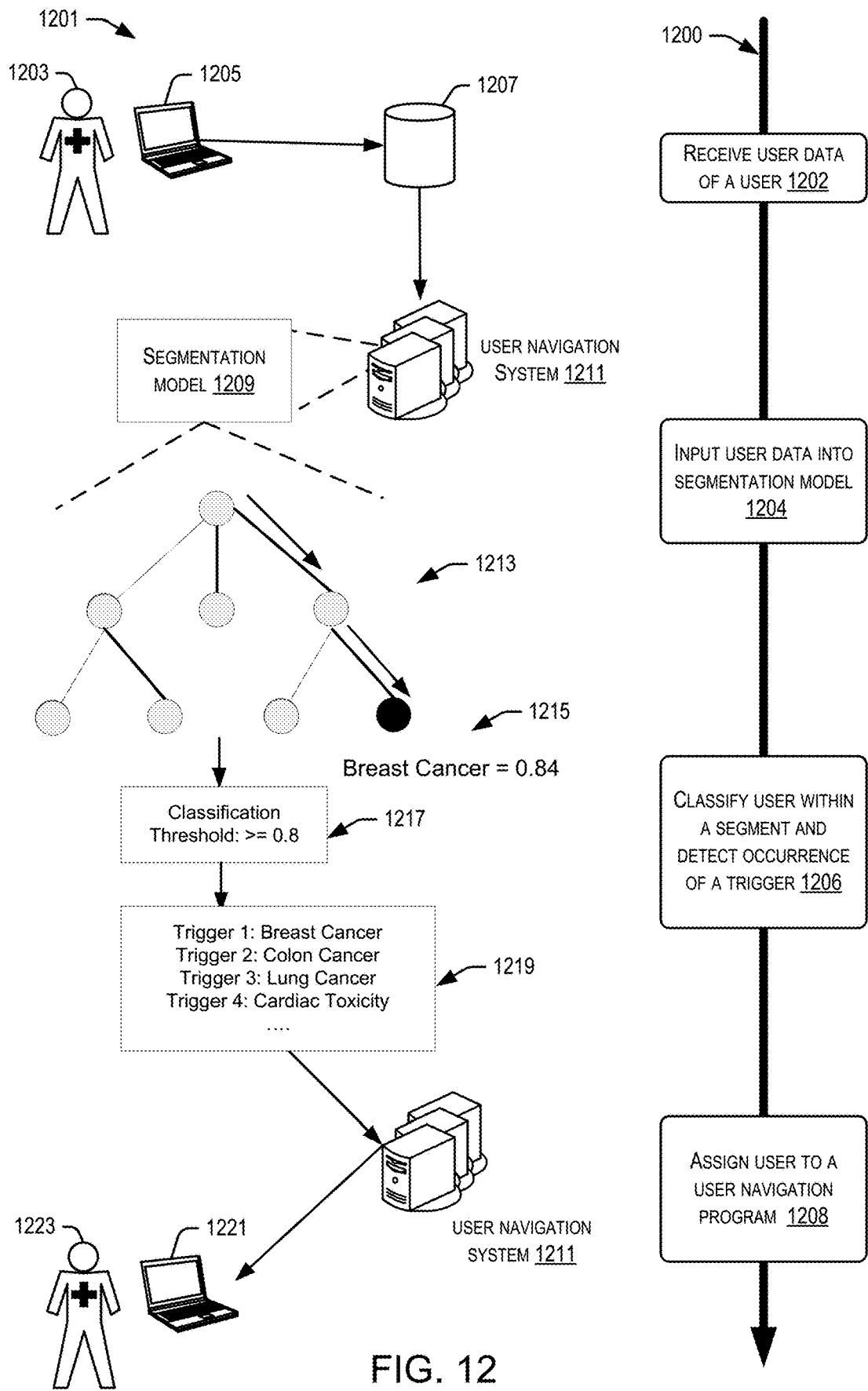
FIG. 12 is an example flowchart illustrating a process for assigning a user to a user navigation program, according to at least one example.

FIG. 12 illustrates a simplified block diagram 1201 depicting an example process 1200, in accordance with at least one example. The process 1200 is an example process for assigning a user to a user navigation program using a prediction model. The prediction model (also referred to as a "segmentation model") may be trained to classify users into one or more segments. The diagram 1201 depicts example states that correspond to the blocks of the process 1200. The diagram 1201 includes devices 1205 and 1217, a data store 1207 (e.g., which may be similar to data store 226 of the transformative processing engine 202), and UN system 1211 (e.g., which may be similar to UN system 1102 of FIG. 11), that perform at least a portion of the process 1200.

The process 1200 begins at block 1202 whereby a UN system receives, from a device, user data for a particular user. For example, device 1205 may be operated by a USP of a service facility and may receive input related to the particular user's service/condition. For example, the device 1205 may correspond to a generation component (e.g., generation component 906 of FIG. 9), such as a blood chemistry analyzer, a laptop, a service imaging device, etc. As described herein, the user data may include structured or unstructured user data, and may be associated with a present condition (e.g., breast cancer) or a present service status (e.g., results from first round of chemotherapy) of the user. Upon receiving input, the device 1205 may transmit the user data for the particular user over a network to the UN system 1211 (and/or an affiliated service management system) for storage in data store 1207 of the service management system. The user data may be incorporated into a new or existing user service record of the user. The service facility may be one of several service facilities maintained by a service organization. The service organization may maintain the service management system that is configured to receive data (e.g., user service records, lab test results, etc.) from each of the service facilities (e.g., into the centralized data store 1207 of the service management system). It should be understood that, although in this example, a user data for a single user is described, in other examples, user data for multiple users may be received (e.g., for an entire service facility, department within a facility (e.g., Emergency Department), division, or enterprise). The user data may be received according to any suitable cadence (e.g., in substantially real-time, whenever a user's record is updated, or on a predetermined schedule).

At block 1204, the UN system 1211 may input the received user data into a trained segmentation model 1209 of the PIP system 1211. The trained segmentation model 1209 may be trained to output a score based in part on the received user data, whereby the score corresponds to a level of confidence of a classification of the user into a particular segment (among a plurality of candidate segments). In some examples, the particular segment may be associated with the present condition or the present service status of the user. In some examples, the segment may be associated with a predicted future condition or future service of the user. As described above, in some examples, UN system 1211 may be affiliated with the service management system. In some examples, the UN system 1211 may be a component of the service management system. In some examples, the UN system 1211 may retrieve the user data from the data store 1207 of the service management system for input into the trained segmentation model 1209. The trained segmentation model 1209 may be trained based at least in part on features derived from user training data from multiple users previously collected by the service management system (across the different service facilities of the service organization). Each training data sample of the training data may include multiple data points drawn from one or more sources, including, but not limited to, blood lab data, vital signs (e.g., body temperature, blood pressure, etc.), user age, user body mass index (BMI), etc. The data points may also be associated with past, present or anticipated future service (e.g., chemotherapy service) and/or conditions of the user (e.g., breast cancer). The segmentation model may be trained according to one or more machine learning algorithms, as described with reference to FIG. 10 (e.g., blocks 1002-1006). For example, as depicted in FIG. 12, the segmentation model 1209 may utilize one or more decision trees 1213 (e.g., a boosting decision tree model). The training data may be used to configure nodes and interconnections between nodes of each decision tree 1213, in order to maximize information gain, balance variance and bias, and improve precision and recall values (e.g., for achieving a target F1 value). Although a decision tree 1213 is depicted in FIG. 12, it should be understood that any suitable algorithm may be used to generate the segmentation model, for example, as described with reference to FIG. 10.

In some examples, the segmentation model 1209 may utilize one or more models (e.g., sub-models of an ensemble of models) to generate one or more scores. For example, a neural network model (e.g., a natural language processing (NLP) model) may be trained to receive as input clinician notes of a pathology report (e.g., text-based unstructured data input). In some examples, the NLP model may utilize a word2vec model (e.g., a continuous bag-of-word (CBOW) model or a skip-gram (SG) model). The word2vec model may be used to learn word embeddings in order to determine semantic meanings of words within the clinician notes. The NLP model may utilize the neural network that is trained and executed similar to as described with reference to FIG. 10 (e.g., based on a corpus of clinicians notes compiled from clinicians throughout the enterprise). The neural network may be trained to recognize words from the pathology report and predict a likelihood of a particular condition (e.g., breast cancer). In another example, another neural network may be trained to receive as input clinician notes of a radiology report, and may be similarly (or differently) trained. It should be understood that different models may be trained using different training data, and may accordingly assign different weights to interconnections between nodes for the respective model. Also, each model may be associated with one or more classification thresholds (discussed further below), which may differ between models. The output of a given neural network model (e.g., a probability and/or classification of a particular condition) may be a feature (of a plurality of features) that is input to the trained segmentation model 1209 for generating a score. In another example, the trained segmentation model 1209 may be used to generate more than one score for a given set of user data (e.g., utilizing one or more sub-models), as described further below. The received user data for the particular user may include similar data points as the training data samples that were used to train the segmentation model 1209.

At block 1206, the UN system 1211 may classify the user within a particular segment, and then detect an occurrence of a trigger based at least in part on the classification of the user. In an example, the segmentation model 1209 of the UN system 1211 may determine a score for the particular user based at least in part on the received user data. For example, continuing with the boosted decision tree model 1213 example, the plurality of data points of the user data may be mapped to features by which the segmentation model 1209 was previously trained. Based on values for each of these features, the boosted decision tree model 1213 may output a score (e.g., a probability of a particular classification) at a leaf node 1215 (e.g., 84%). In the example of leaf node 1215, the particular score may be associated with a classification of "breast cancer." The UN system 1211 may then classify the user as having breast cancer based at least in part on the score being in accordance with (e.g., greater than or equal to) a classification threshold 1217 (e.g., 80%). In some examples, the classification threshold may be associated with a level of confidence of the score.

Upon classifying the user within the particular segment, the UN system 1211 may detect an occurrence of a trigger based at least in part on the classification. The trigger may be one of a plurality of triggers 1219 maintained by the UN system 1211. For example, as depicted in FIG. 12, the plurality of triggers 1219 may include a trigger for "breast cancer," "colon cancer," "lung cancer," "cardiac toxicity," etc. In this example, the score 1215 of 0.84 for "breast cancer" may cause the occurrence of the "breast cancer" trigger. As described herein, the "breast cancer" trigger may be associated with a particular user navigation program (e.g., the breast cancer navigation program).

In some examples, as described above, the segmentation model 1209 may output more than one score for a given user. Additionally, each score for a particular segment may be assessed against a respective classification threshold for the particular segment. For example, the segmentation model 1209 may determine a 90% probability score that the user has "cancer" (a broader segment), an 84% probability score that a user has "breast cancer" (i.e., a narrower segment), a 70% probability score that the user has "lung cancer," and a 65% probability score that the user has "stage 1 breast cancer" (i.e., an even narrower segment). In this example, the segment for "cancer" may be associated with a classification threshold whereby at least a 95% score is required to classify the user with cancer (e.g., partially due to low rates of potential error determined from the training process). However the segment for "stage 1 breast cancer" may have a lower threshold, whereby a score that is at least 60% is deemed sufficient to classify the user as having stage 1 breast cancer. In some examples, a particular threshold value may be determined in part to meet a predefined F1 (e.g., precision, recall) goal (e.g., set by an administrator of the system). The threshold value and/or priority (described below) of the user may also be set and/or adjusted based at least in part on a number of available USPs (e.g., user navigators). It should also be understood that the threshold values may differ depending on the segment subject area. For example, while breast cancer and lung cancer are both types of cancer, the segmentation models that are used to predict each type of cancer may use different training parameters and/or have different precision/recall rates. Accordingly, scores output from each model may be compared against different respective threshold values. It should be understood that, while some segments may be more difficult to predict (e.g., a condition of the user), and may thus be associated with lower threshold values, other classifications may require a score of 1.0 to be in accordance with a higher respective classification threshold. For example, in the case where a segment is associated with a service status of the user (e.g., "discharged within the last week," "currently prescribed with XYZ medication," etc.), the system may be expected to determine with 100% confidence the particular segment (e.g., as it may be readily obtained from structured data within the user's service record).

It should further be understood that, just as there may be more than one score and respective segmentation for a given user data, the UN system 1211 may detect an occurrence of more than one trigger (e.g., per segment) based on the user data. Furthermore, in some examples, an occurrence of a particular trigger (e.g., associated with being a candidate for a particular user navigation program) may require a classification in two or more segments. Consider a case where the user was recently released from the service facility within the last couple days. While admitted, the user underwent blood tests that indicated signs of breast cancer as well as metastasis to other areas of the body (e.g., the lung). The UN system 1211 may classify the user within the segments of "recently discharged," "stage 2 breast cancer," and "stage 1 lung cancer." In this example, the UN system 1211 may subsequently detect an occurrence of two triggers. For example, the system may determine, based in part on the "recently discharged" and "stage 2 breast cancer" segmentations, an occurrence of the "breast cancer" trigger (e.g., that the user is a candidate for a breast cancer navigation program). The system may further determine, based in part on the "recently discharged" and "stage 1 lung cancer" segmentations, an occurrence of the "lung cancer" trigger (e.g., that the user is also a candidate for the lung cancer navigation program). Any suitable mappings between user segmentations and triggers may be utilized to perform embodiments of the present disclosure.

At block 1208, the UN system 1211 may assign the user to a user navigation program. In an example, following the detection of an occurrence of one or more triggers, the UN system 1211 may determine a priority for the user based at least in part on the occurrence of the one or more triggers. In some examples, the priority may correspond to a priority for the user (among a plurality of users of the service organization) for being assigned to a user navigation program. For example, a particular trigger may be associated with a severity of a particular condition associated with the classification. A trigger associated with a high severity condition (e.g., classification) may thus be associated with a high priority for the user. In another example, a trigger may be associated with a stage of condition in which there is a high probability that a pairing with a user navigator would lead to positive user outcomes. In this case, as well, the system may determine a higher priority for the user based on the occurrence of the trigger. Any suitable factor(s) may be used to determine the priority for being assigned to a user navigation program (e.g., user data, availability of USP resources, availability of service equipment, a number of users in the queue, etc.).

As described above, the one or more triggers may respectively be associated with a particular user navigation program of a plurality of user navigation programs. For example, a "breast cancer" trigger may be associated with a breast cancer navigation program, a "lung cancer" trigger may be associated with a lung cancer navigation program, etc. In some examples, multiple triggers may be associated with the same user navigation program, although each trigger may be associated with a different (or similar) priority. Continuing with the example depicted in FIG. 12, an occurrence of a "breast cancer" trigger may be associated with a moderate priority to be assigned to a breast cancer navigation program. In this case, the UN system 1211 may determine to assign the user to the breast cancer navigation program, for example, if there is an available user navigator for pairing. In another example, if the user triggered with a "stage 1 breast cancer," the UN system 1211 may determine a high priority level for the user to be assigned to the breast cancer navigation program. This may be partially due to a desire to engage with users earlier in a cancer journey to achieve a higher likelihood of a positive outcome. In some examples, upon assigning the user to a particular user navigation program, the UN system 1211 may transmit a message to a user device 1221 of a USP 1223 (e.g., a user navigator, user navigation coordinator) for presentation (e.g., on a dashboard of the user device 1221). For example, the message may notify a user navigator of their assignment to the user. In another example, the message may include one or more recommendations and/or instructions directing the user navigator on how to help the user navigate their particular user journey.

Figure 13:
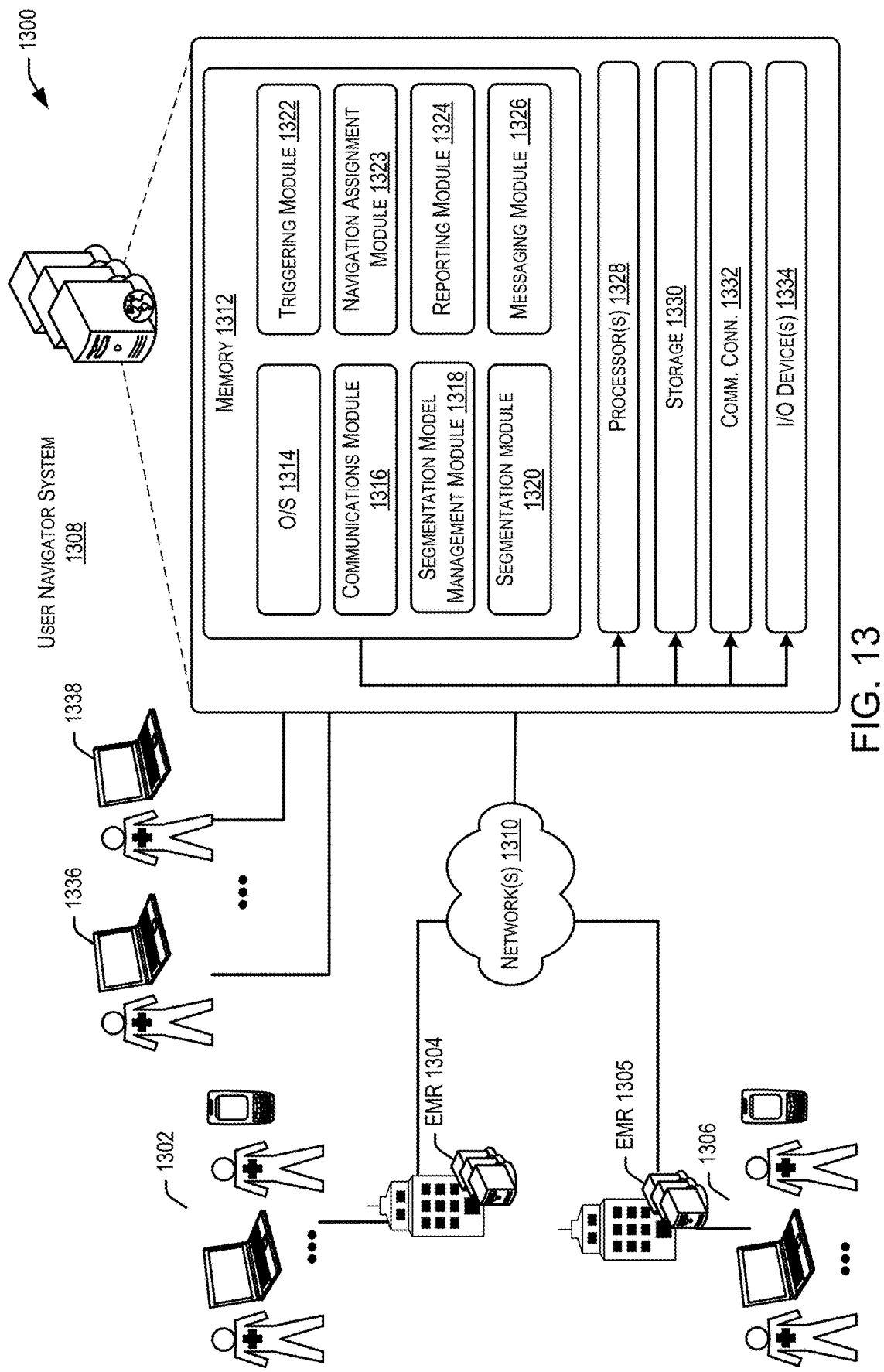
FIG. 13 is another example architecture illustrating a system in which techniques relating to assigning a user to a user navigation program may be implemented, according to at least one example.

FIG. 13 illustrates a simplified block diagram depicting an example architecture 1300 of a UN system, in accordance with at least one example. The diagram depicts a plurality of service facilities, whereby each service facility may be affiliated with a service organization that maintains a service management system. Each service facility may further be associated with (e.g., employ) one or more USPs (e.g., respectively represented in FIG. 13 by USPs 1302 and 1306). Each USP (e.g., including physicians, nurses, etc.) may be responsible for service for one or more users. A device (e.g., tablet, mobile phone, laptop, desktop, server, lab equipment, etc.) associated with the PC may receive input from the USP and generate user data that is transmitted to a system associated with the particular service facility. For example, as depicted in architecture 1300, the respectively service facilities are each associated with an EMR system (e.g., EMR 1304, 1305). Upon receiving user data, an EMR (e.g., EMR 1304) may then transmit the user data over a network 1310 to a UN system 1308 (which may be similar to user navigation system 1102 or 1211). The UN system 1308 may process the user data, as described below, and subsequently transmit data for presentation on one or more devices (e.g., represented by device 1336 and device 1338) to be used in coordinating user navigation.

It should be understood that a service facility may be associated with any number and/or type of suitable systems. Also, it should be understood that, although EMR 1304 and 1305 are depicted in FIG. 13 as being respectively associated with a particular service facility, embodiments should not be construed to be so limited. For example, the service management system (e.g., maintained by the service organization) may be associated with a plurality of EMRs that are distributed in any suitable fashion (e.g., geographically dispersed per division, per department, etc.). Also, the devices 1336 and 1338 may each be associated with different types of USPs and/or present different types of data, depending on the context, as described herein. For example, in one context, device 1336 may be associated with a first user navigator of a first user navigation program, while device 1338 may be associated with a second user navigator of a second user navigation program. In this context, and for example, the first user navigator may be responsible for a subset of users of the service facility associated with EMR 1304. In another example, the first user navigator may be responsible for users across multiple service facilities. In another context, either of device 1336 or 1338 may be associated with a user navigation coordinator of the enterprise. In this context, and for example, the devices 1336 or 1338 may present a GUI interface (e.g., a dashboard) for a USP (e.g., a user navigation coordinator, service facility executive, administrator, etc.) for coordinating user service.

It should further be understood that the user data received by the UN system 1308 may be representative of a large number of users (e.g., over 300,000 users of the service organization). This user data may be used to define one or more sets of training data, as described with reference to FIGS. 9 and 10 (e.g., the data preparation engine 914 of FIG. 9). The one or more sets of training data may be stored in a data store (e.g., data store 915) of the UN system 1308.

Turning to network 1310 in further detail, the network 1310 may include any suitable communication path or channel such as, for instance, a wire or cable, fiber optics, a telephone line, a cellular link, a radio frequency (RF) link, a WAN or LAN network, the Internet, or any other suitable medium. The network 1310 may include any one or a combination of many different types of networks, such as cable networks, the Internet, wireless networks, cellular networks, and other private and/or public networks. In some examples, as described above components of the architecture 1300 (e.g., EMR 1304 and 1305, devices 1302, 1306, 1336, and/or 1338) may communicate over the network 1310 with the user navigator system via HL7 formatted messages or any other suitable format.

Turning to the contents of the UN system 1308 in more detail, the UN system 1308 may be a computer system that includes at least one memory 1312, one or more processing units (or processor(s)) 1328, a storage unit 1330, a communication device 1332, and an I/O device 1334. The processor(s) 1328 may be implemented as appropriate in hardware, computer-executable instructions, firmware or combinations thereof. Computer-executable instructions or firmware implementations of the processor(s) 1328 may include computer-executable or machine executable instructions written in any suitable programming language to perform the various functions described.

The memory 1312 may store program instructions that are loadable and executable on the processor(s) 1328, as well as data generated during the execution of these programs. Depending on the configuration and type of UN system 1308, the memory 1312 may be volatile (such as random access memory (RAM)) and/or non-volatile (such as read-only memory (ROM), flash memory, etc.). In some implementations, the memory 1312 may include multiple different types of memory, such as static random access memory (SRAM), dynamic random access memory (DRAM) or ROM. The UN system 1308 may also include additional storage 1330, such as either removable storage or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some examples, the additional storage 1330 may include (or be affiliated with) one or more data stores of the transformative processing engine 202 of the service management system.

The UN system 1308 may also contain communications connection(s) 1332 that allow the UN system 1308 to communicate with a stored database, another computing device or server, user terminals, and/or other devices on the network(s) 1310. The UN system 1308 may also include input/output (I/O) device(s) and/or ports 1334, such as for enabling connection with a keyboard, a mouse, a pen, a voice input device, a touch input device, a display, speakers, a printer, etc.

Turning to the contents of the memory 1312 in more detail, the memory 1312 may include an operating system 1314 and one or more application programs or services for implementing the features disclosed herein, including a communications component 1316, a rules management component 1318, a segmentation component 1320, a triggering component 1322, a navigation assignment component 1323, a reporting component 1324, and a messaging component 1326.

The operating system 1314 may provide executable program instructions for the general administration and operation of UN system 1308 and typically will include a computer-readable storage medium (e.g., a hard disk, random access memory, read only memory, etc.) storing instructions that, when executed by a processor of the UN system 1308, allow the UN system 1308 to perform its intended functions. Suitable implementations for the operating system and general functionality of the servers are known or commercially available and are readily implemented by persons having ordinary skill in the art, particularly in light of the disclosure herein.

The communications component 1316 may include code that causes the processor 1328 to generate messages, forward messages, reformat messages, and/or otherwise communicate with other entities (e.g., using an HL 7 format or any other suitable format). For example, the communications component 1316 may receive user data associated with a user from an EMR (e.g., 1304) and/or one or more devices (e.g., 1302). As described above, it should be understood that the communications component 1316 may receive data (e.g., user data) from any suitable source (e.g., emergency department (ED) discharge systems, service clinics, etc.). In some examples, the communications component 1316 may further communicate with an enterprise master patient index (EMPI) (e.g., of the service management system) to ensure that user data received from various devices and/or EMRs are consistent for a given user (e.g., utilizing a unique identifier for a given user of the service management system). In some examples, the communications component 1316 may receive messages that correspond to a data stream (e.g., a sequences of messages transmitted in substantially real-time). In some examples, the data stream may be transmitted from one or more sources (e.g., EMRs) to an intermediary data store, before being eventually stored in an electronic data warehouse (EDW). The communications component 1316 may analyze (e.g., parse) the messages from the data stream while stored in the intermediary data store, and determine if they should be further processed (e.g., for user segmentation and trigger occurrence detection) and/or stored by the UN system 1308 (e.g., in storage 1330).

The segmentation model management component 1318 may include code that causes the processor 1328 to generate and maintain one or more segmentation models. In some examples, the segmentation model management component 1318 may perform one or more of the functions of the prediction model management engine 902 of FIG. 9, as described herein. The segmentation model management component 1318 may receive (or generate) one or more rules that correspond to instructions for the operations of a given segmentation model. For example, as described herein, a prediction (e.g., segmentation) model may be trained using training data to infer relationships (e.g., using supervised or unsupervised learning) between data points in order to make predictions about classifying the respective user within one or more segments. The segmentation model management component 1318 may also receive as input, via user device, human-generated rules to be used for segmentation. For example, a service facility administer may determine a rule that users with particular characteristics be classified within newly formed segment (e.g., "users presenting symptoms of stage 1 breast cancer"). A segmentation model may thereafter be trained to identify users that are most likely fitting within this segment.

The segmentation component 1320 may include code that causes the processor 1328 to determine a score for a user that corresponds to a level of confidence of a classification of the user within a particular segment. The segmentation component 1320 may further classify the user within the particular segment based at least in part on the score being in accordance with a classification threshold, as described with reference to FIG. 12. It should be understood that the segmentation component 1320 may execute by utilizing a trained (e.g., configured) segmentation model. In some examples, the segmentation component 1320 may receive user data in substantially real time as updated user data is generated. As new user data is received, the predicted segment for the user may be further refined (e.g., funneled). For example, at a first time, the segmentation component 1320 may receive user data which is used to predict that the user may have cancer. At a later time, the segmentation component 1320 may receive updated user data (e.g., a new pathology report) which it uses to classify the user as having breast cancer. At a yet later time (and/or execution process), the segmentation component 1320 may receive further updated data (e.g., a new radiology report) which is used to classify the user as having stage 1 breast cancer. It should be understood that the segmentation component 1320 may be able to refine (e.g., narrow) a user's classification using the same user data, for example, by executing a different segmentation model that is trained using more narrowly focused training data. It should also be understood that, in some examples, the segmentation component 1320 may utilize new data to classify a user within new segments (e.g., cardiac toxicity), which may or may not be related to a previously classified segment (e.g., stage 1 breast cancer).

The triggering component 1322 may include code that causes the processor 1328 to detect an occurrence of one or more triggers based at least in part on received user data, for example, as described with reference to FIG. 12. For example, the triggering component 1322 may maintain a plurality of triggers. In some examples, a trigger of the plurality of triggers may be automatically generated by the system in the form of a rule (e.g., generating a new trigger based on a newly created segment). A priority for the trigger may be determined by the system based at least in part on the particular segment type (e.g., a stage of cancer, a severity of a condition associated with the segment). In some examples, a trigger rule may be generated (or modified) by a user (e.g., a service facility executive, system administrator, or user navigation coordinator) and received as input from a user device of the user by the triggering component 1322. For example, a user may assign a priority to a trigger based on one or more factors, including business goals (e.g., user navigation program enrollment targets), desired metrics goals (e.g., F1 statistics), new areas user navigation, etc. Upon the occurrence of a trigger, the triggering component 1322 may determine a priority of the user based in part on the assigned priority of the trigger. In another example, a user may map a trigger to a particular user navigation program, which may be later used to assign a user to a particular user navigation program upon the occurrence of the trigger. A trigger may correspond to any suitable format. In one non-limiting example, a trigger format may correspond as follows:

Trigger Name: Stage 1 Breast Cancer
Required Triggering Segments:
 "Recently Discharged"
 "Stage 1 Breast Cancer"
Associated User Navigation Program: Breast Cancer
 Navigation Program
Priority: 1

As described above, as new user data is received (and/or other specialized segmentation models are executed), new triggers may occur. In some examples, these new triggers may be associated with other user navigation programs, and may be used by the UN system 1308 to determine an assignment of the user to one or more user navigation programs. In some examples, the triggers may be used not only for assigning a user to a particular user navigation program, but also for determining one or more tasks (e.g., instructions, recommendations) to be presented for a user navigator to be used in helping the user navigate their user journey.

The navigation assignment component 1323 may include code that causes the processor 1328 to determine an assignment of a user to one or more user navigation programs. The navigation assignment component 1323 may determine an appropriate outcome based on one or more factors, including, but not limited to: whether the user is already enrolled in an existing navigation program, comparing priorities of multiple triggers which may have occurred, determining whether a particular trigger corresponds to a root condition or a metastatic condition, a current level of demand for a particular user navigation program, etc. In one example, where a user may not be enrolled yet in any user navigation program, the navigation assignment component 1323 may assign the user to a particular user navigation program that is associated with the trigger that occurred. In another example, where the user may already be enrolled in a particular navigation program (e.g., already paired with a user navigator), the navigation assignment component 1323 may determine to suppress a new trigger occurrence and route messages to the existing user navigator, as described further below with reference to FIG. 14. In another example, the navigation assignment component 1323 may determine, based on the occurrence of one or more triggers, to assign a user to an additional user navigation program (e.g., in addition to an existing enrolled program). In yet another example, the triggering component 1322 may determine to enroll the user in a customized user navigation program, as described further below.

The reporting component 1324 may include code that causes the processor 1328 to generate one or more reports for presentation on a user device (e.g., device 1336 or 1338). The reports may be used to assist USPs (e.g., user navigators and/or user navigation coordinators) in managing user navigation programs. In one example, a report may be used to indicate progress of one or more users through particular navigation programs. For example, the report may indicate how many users remain engaged once they are enrolled in a particular program. The report may also indicate a likelihood of remaining engaged depending on how early in the process a user is enrolled. The report may further compare outcomes across different users, depending on their levels of engagement. In another example, a report may be used to indicate opportunities for better utilization of user navigation programs. For example, the report may indicate which triggers are most likely to occur together for any given user. The report may also indicate which users are already assigned to more than one user navigation program. A USP may use this information to determine how to improve the coordination, workflow, and availability of the various user navigation programs offered. For example, one or more rules may be generated based on this information, which may be used to improve future segmentation and/or triggering.

The messaging component 1326 may include code that causes the processor 1328 to generate one or more messages for use in coordinating service for a user. In an example, and as described herein, a user may be paired with one or more user navigators, respectively, based on an assignment to one or more user navigation programs. A user device of a user navigator (e.g. device 1336 or 1338) may be configured to receive messages from the UN system 1308, whereby each message may correspond to instructions for coordinating service for the user. In some examples, the UN system 1308 may maintain one or more queues of messages. As new data (e.g., user data) is received from a device (e.g., device 1302), the UN system 1308 may process the data, determine an occurrence of a trigger, and subsequently determine one or more messages (e.g., tasks) to be generated based on the occurrence of the trigger. The one or more messages may be added to a queue for retrieval and presentation on a user device (e.g., device 1336 or 1338) of the user navigator. It should be understood that the entire process, from receiving new data to generating new messages, may be performed within substantially real-time (e.g., seconds or minutes). The messaging component 1326 may further be configured to receive feedback messages from a device (e.g., device 1336 or 1338) and perform further processing. For example, user device 1338 may receive input from a user navigator indicating that a certain task has been performed (e.g., the user was reminded of an upcoming appointment), or that a new event has occurred (e.g., blood lab results have been generated). Upon the messaging component 1326 receiving a feedback message containing this input, the UN system 1308 may process the feedback. For example, the system may determine, based on the feedback, if any new triggers have occurred. If so, the system may generate one or more new messages for addition to a queue. In one example, the messages may be added to a queue for another user navigator (e.g., of device 1336). In this way, the UN system 1308 may facilitate coordination of messaging (e.g., between a user navigator and a user, or between user navigators). In some examples, the processing of feedback messages may further be performed in substantially real-time. It should be understood that messages generated by the messaging component 1326 may correspond to any suitable subject matter, including, but not limited to, a condition and/or service status of the user (e.g., which may be associated with a segmentation that caused an occurrence of a particular trigger).

Figure 14:
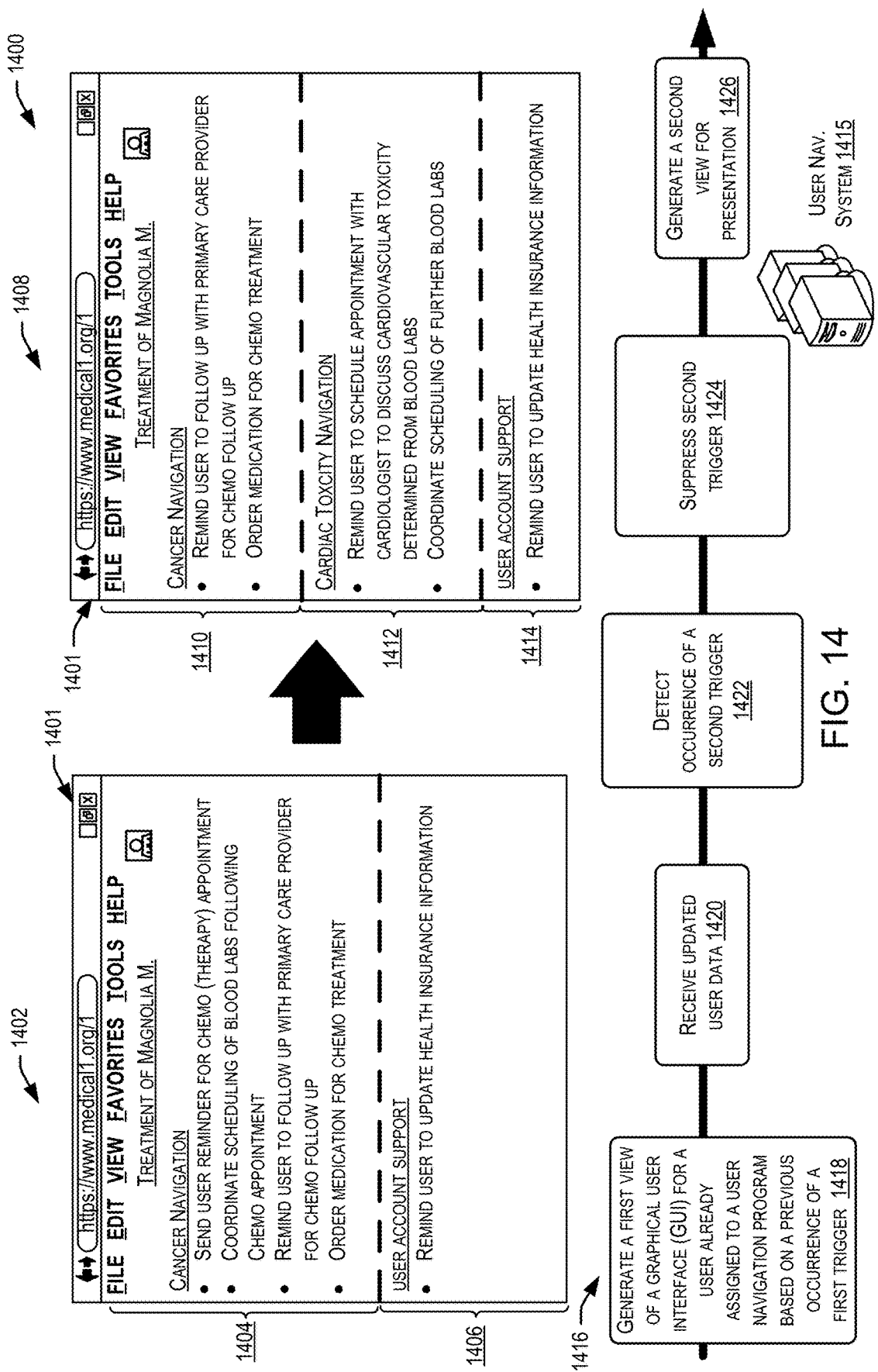
FIG. 14 illustrates an example process for assigning service for a user based on updated user data, according to at least one example.

FIG. 14 illustrates two views 1402, 1408 of a graphical user interface (GUI) 1401 corresponding to an example process 1416, in accordance with at least one example. The process 1416 is an example process for assigning service for a user based on updated user data, and then accordingly updating the GUI 1401 based on the assigned service. In the depiction of FIG. 14, the assignment of user service corresponds to one or more tasks (e.g., instructions, recommendations) assigned to a user navigator for caring for the user. In this example, the user is already assigned to a particular user navigation program (e.g., an oncology cancer navigation program). The tasks may correspond to messages transmitted from a UN system 1415 (e.g., which may be similar to UN system 1308 of FIG. 13) to a navigator device (e.g., device 1336 or 1338) for presentation on the GUI 1401 of the device. As depicted in FIG. 14 and described further below, the one or more tasks may be presented within one or more different navigation support areas within the GUI 1401 (e.g., 1410, 1412, 1414, 1406, 1404). It should be understood that, although the GUI 1401 primarily depicts assignment of service in the context of task management, examples of the present disclosure should not be construed to be so limiting. For example, the GUI 1401 may have other views and/or functions, including, but not limited to, updating user records, sending reminders to the user via the GUI, presenting the user's latest service status (e.g., blood lab results, pulse, blood pressure, etc.), listing other USPs who may currently (and/or previously) provide service for the user, presenting the user's health insurance information, etc.

Certain blocks of the process 1416 correspond to the views 1402, 1408 of the GUI 1401. For example, blocks 1418 and 1426 respectively correspond to the view 1402 (e.g., a first state of the GUI 1401) and the view 1408 (e.g., a second state of the GUI 1401). The blocks 1420, 1422, and 1424 are performed as part of transitioning from the view 1402 to the view 1408. In this example, the views 1402 and 1408 are presented to the same user navigator who is treating a user ("Magnolia M."). The process 1416 corresponds to a process by which the first view 1402 is updated to generate the second view 1408 based on the updated user data (e.g., indicating the user's updated condition or service status) received by the UN system 1415.

The process 1416 begins at block 1418 by the UN system 1415 generating the first view of a GUI for a user that is already assigned to a user navigation program. The user may already be assigned to the user navigation based at least in part on a previous occurrence of a first trigger (e.g., indicating a cancer condition of the user). In some examples, the GUI 1401 may correspond to a web page that is generated and served by the UN system 1415 for presentation on the user navigator's device. In some examples, the GUI 1401 may be associated with an application that is executed locally on the user navigator's device. The application may receive messages generated by the UN system 1415 (e.g., via Extensible Markup Language (XML), or any suitable variant format) suitable for presentation in the GUI 1401. Generating the first view 1402 includes arranging the elements introduced above (e.g., tasks) within the first view 1402. The elements are presented in one or more navigation support areas (e.g., 1404, 1406) of the GUI 1401. For example, the tasks within the Oncology (Cancer) Navigation support area 1404 include, for example: Send user reminder for chemotherapy appointment, Coordinate scheduling of blood labs following chemotherapy appointment, Remind user to follow up with primary service provider for follow up to chemotherapy service, Order medication for chemotherapy service, etc. As described above, these tasks may be determined by the UN system 1415 based on one or more user data inputs (e.g., the user's service record, an appointments management system, known affiliations between the user and one or more USPs, user prescriptions, clinician notes from a recent visit, etc.). These user data inputs may cause the occurrence of one or more triggers, which may in turn cause one or more tasks to be generated and added to a queue. The device of the user navigator may retrieve tasks from the queue for presentation in the GUI 1401. The UN system 1415 may determine tasks for more than one navigation support area. For example, as depicted in GUI 1401, another navigation support area may be User Account Support 1406. Tasks within this support area may include, for example, Remind user to update health insurance information, etc. It should be understood that any number and/or type of user navigation support areas may be presented within the GUI 1401.

At block 1420, the UN system 1415 may receive updated user data. In some examples, the updated user data may correspond to an updated condition or an updated service status of the user. In some examples, the updated data may be generated at least partially in response to action taken by the user and/or the user navigator. For example, continuing with the example depicted in GUI 1401, the user navigator may perform the task of sending the user a reminder for a chemotherapy appointment that was previously schedule. Following the completion of the chemotherapy, the user navigator may also coordinate the scheduling of blood labs for the user. Upon the completion of the blood labs, updated user data (e.g., the results of the blood labs) may be received by the UN system 1415. For example, the updated user data may be received from a user device (e.g., device 1302 or 1306 of FIG. 13) of a USP performing the blood labs. In another example, the updated user data may be received from the user navigator device itself (e.g., device 1336 or 1338), for example, upon the user navigator inputting that one or more tasks have been performed (or other user-related input). In some examples, the updated condition or updated service status may correspond to an anticipated future condition or service status. For example, the updated service status may correspond to an indication that the user is anticipated to be discharged within the next day. In another example, the updated condition may indicate that the user has an increased risk for septic shock.

At block 1422, the UN system 1415 may detect an occurrence of a second trigger. In some examples, the second trigger may indicate that the same user (i.e., Magnolia M.) has been classified within a new segment, for example, as described with reference to FIG. 12. For example, the continuing with the illustration where the updated user data corresponds to blood lab results, the blood labs results may indicate that the user has an increased level of cardiovascular (e.g., cardiac) toxicity (e.g., due in part to the chemotherapy services being received as part of the oncology). Accordingly, the user may be classified as falling within a "cardiac toxicity" segment.

At block 1424, the UN system 1415 may suppress the second trigger. In some examples, the suppression of the second trigger may correspond to the system determining that the user should not be assigned to an additional user navigation program (e.g., for cardiac toxicity). For example, continuing with the above illustration, the system may determine that the increase in cardiac toxicity levels are likely due to the chemotherapy of the user (i.e., it is related condition that may be a byproduct of the root condition). The system may make this determination in any suitable way, as described herein (e.g., comparing priorities and/or severity levels between segments, analyzing historical condition and/or service data of the user, etc.). The system may further determine that the user is already assigned to an existing user navigation program (e.g., the cancer navigation program). Based on at least one or more of these factors, the system may determine that, instead of assigning the user to a new navigation program, messages related to the cardiac toxicity condition should be routed to the existing user navigator for a unified view, as discussed further below. In this case the system may determine that the existing user navigator has a sufficient level of training and expertise to handle tasks related to the additional user condition. In some examples, the determination by the system about whether to suppress a trigger and/or assign the user to a new navigation program may be done automatically be the system. In some examples, the system may receive input from a human administrator (e.g., a USP), for example, to indicate approval of a system recommendation regarding user navigation. In this example, by suppressing the second trigger and not assigning the user to a new navigation program, the system may reduce the risk of collisions between messages that may otherwise be caused if the user were to be concurrently assigned to multiple user navigation programs. For example, if the user were assigned to two different user navigators for two different (but related) conditions (e.g., cancer and cardiac toxicity), the two user navigators may not coordinate messages with each other that are sent to the user, or otherwise be aware of other aspects of the user's overall navigation journey. This might cause message duplication or, alternatively, conflicting messages being sent to the user, which could lead to decreased quality of user service and/or lower system efficiency. Instead, by suppressing the second trigger, and, more generally, by holistically managing the user's overall journey, the UN system 1415 may be more efficient than conventional techniques and improve user outcomes.

At block 1426, the UN system 1415 may generate a second view for presentation on the GUI. Continuing with the example above, following the suppression of the second trigger at block 1424, the UN system 1415 may generate and route new messages related to the occurrence of the second trigger (e.g., associated with the newly discovered cardiac toxicity condition) to the user device of the existing user navigator (e.g., for the cancer navigation program). The GUI 1401 thereafter may be updated to provide a second view 1408 for presentation on the user navigator's device. Similar to the first view 1402, the second view 1408 may arrange elements in one or more navigation support areas (e.g., 1410, 1412, 1414) of the GUI 1401, based in part on the newly routed messages. For example, the UN system 1415 may determine that the first two tasks related to cancer navigation were completed from navigation support area 1404, and that two tasks still remain. However, a new navigation support area 1412 may be created which may present information related to helping the user navigate the journey related to the cardiac toxicity condition. In this example, the tasks within the Cardiac Toxicity Navigation support area include, for example: Remind user to schedule appointment with cardiology to discuss cardiovascular toxicity determined from blood labs, Coordinate scheduling of further blood labs, etc. Similar to the first view 1402, other previous or new navigation support areas may also be presented (e.g., User Account Support 1414, which may be a remaining task from User Account Support 1406). It should be understood that the presentation of elements and the subject matter depicted in FIG. 14 are representative, and other GUI presentations and/or subject matter may be suitable for performing embodiments of the present disclosure. For example, the user may be recommended to undergo blood labs to monitor multiple conditions (e.g., breast cancer, lung cancer, cardiac toxicity, etc.). Instead of presenting a separate task for blood labs under each navigation area (e.g., 1410, 1412), the UN system 1415 may determine to group (e.g., merge, consolidate) tasks as appropriate. In this way, the user navigator can more efficiently visualize relationships (e.g., between condition-related information, tasks, recommendations) and holistically coordinate the user's journey than conventional techniques.

Figure 15:
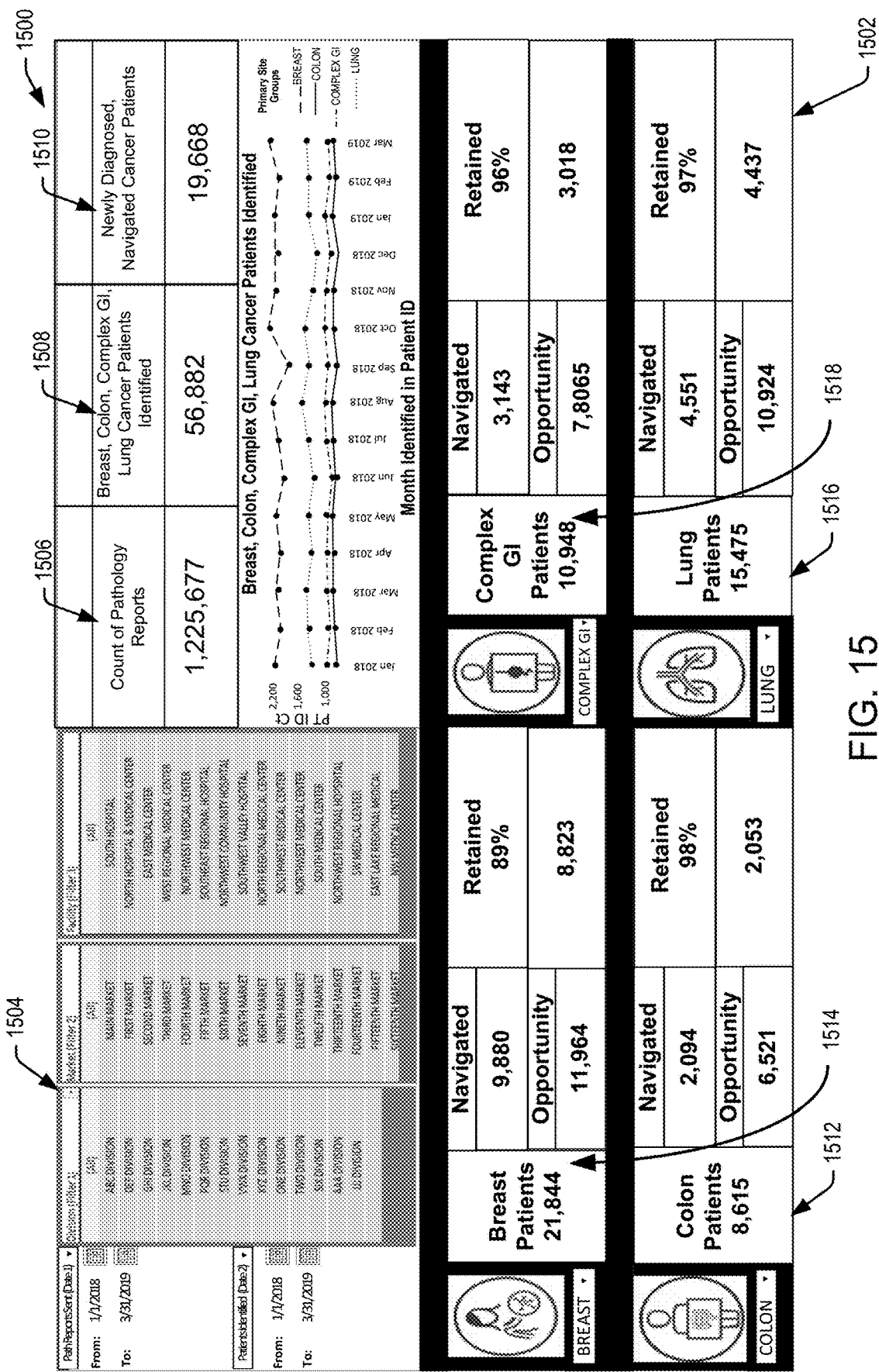
FIG. 15 illustrates an example graphical user interface (GUI) utilizable for coordinating user service among multiple users within a service organization, according to at least one example.

FIG. 15 illustrates a GUI of a display 1500 of a user device, according to at least one example. In some examples, the user device may be similar to device 1336 or 1338 of FIG. 13, and may be associated with a USP (e.g., a user navigation coordinator, a service facility executive, administrator, etc.). In some examples, the GUI 1502 may correspond to a dashboard presentation of an application executing on the user device. The application may allow the USP to see distributions of users according to one or more variables (e.g., applied filters). In some examples, the applied filters may enable a USP to view one or more levels of the organizational hierarchy within the enterprise (e.g., according to division, market, and/or facility). The GUI 1502 of FIG. 15 depicts characteristics (e.g., statistics) of a distribution of users within a selected hierarchical view. These characteristics are associated with, for example, the number of users being processed by the service organization, various segmentations of these users, a number of users enrolled in particular user navigation programs, and opportunities for future user navigation. These characteristics may assist a USP in coordinating user service across one or more user navigation programs to facilitate successful user journey outcomes. It should be understood that other statistical data points (beyond those depicted in GUI 1502) may be suitable for presentation in a GUI for similar usage by USP. For example, as described herein, the GUI 1502 may present data indicating future anticipated demand for service resources (e.g., service equipment, human resources such as user navigators, medication, etc.) based on existing and/or projected enrollment in user navigation programs. The GUI 1502 may also indicate what percentage of users who remain enrolled with a user navigation program have a positive outcome and/or journey experience.

Turning to GUI 1502 in further detail, one or more filters 1504 may present a USP with options for filtering the data. For example, GUI 1502 may allow a USP to filter by Division name, Market, Facility, and one or more date ranges (e.g., a date range of when user reports (e.g., pathology, radiology) were received, a date range for when users were identified).

The GUI 1502 may further present one or more top level statistical data in view of the applied filters. For example, element 1506 depicts a total count (e.g., "1,225,677") of pathology reports received by the system within the selected date range. In some examples, the pathology reports may be indexed according to unique user identifiers (e.g., via an EMPI). Element 1508 depicts a total count (e.g., "56,882") of users with at least one of various types of cancers (e.g., breast cancer, colon cancer, complex gastrointestinal (GI) cancer, or lung cancer) identified by the system. This number represents a subset of the users identified and analyzed from the pathology reports (e.g., by a segmentation model). In particular, the subset corresponds to users that were segmented as having a particular type of cancer. Element 1510 further narrows the subset of element 1508 to encompass a set of users (e.g., "19,668") that are newly diagnosed users that are assigned to one or more user navigation programs. The GUI 1502 may further depict a time chart of users identified with each type of cancer over multiple periods of time.

The GUI 1502 may further present one or more drill-down views that allow a USP to further analyze statistical user data. For examples, each of the drill-down views 1512, 1514, 1516, and 1518 provide a drill-down to a particular segmentation of the cancer users identified by element 1508. For example, view 1512 depicts that, of the total number of users (56,882) identified with a type of cancer, 8,615 users have colon cancer. Of these users, 2,094 users were recently assigned to a colon cancer navigation program (which may be a subset of the number identified by element 1510). Of the number of users recently navigated, 2,053 users may still be currently retained as still being enrolled in the colon cancer navigation program (i.e., 98% retention). Also, of the total number of identified colon cancer users, 6,521 users may represent opportunities for navigation (i.e., the users with colon cancer who have not yet been assigned to the colon cancer navigation program). The depiction may be similar for views 1514, 1516, and 1518. In this way, a USP may be able to analyze opportunities for user service coordination (e.g., within user navigation programs) both at a top-level as well as drilling down into views per user segmentation. For example, a USP may identify that, while navigation programs for colon cancer, complex GI cancer, and lung cancer have high retention rates (e.g., >=95%), breast cancer program retention is below 90%. A USP may conduct further investigation to understand why users may discontinue enrollment with a navigation program. A USP may further explore how to take advantage of identified opportunities to enroll more users in navigation programs for their respective user journeys.

Figure 16:
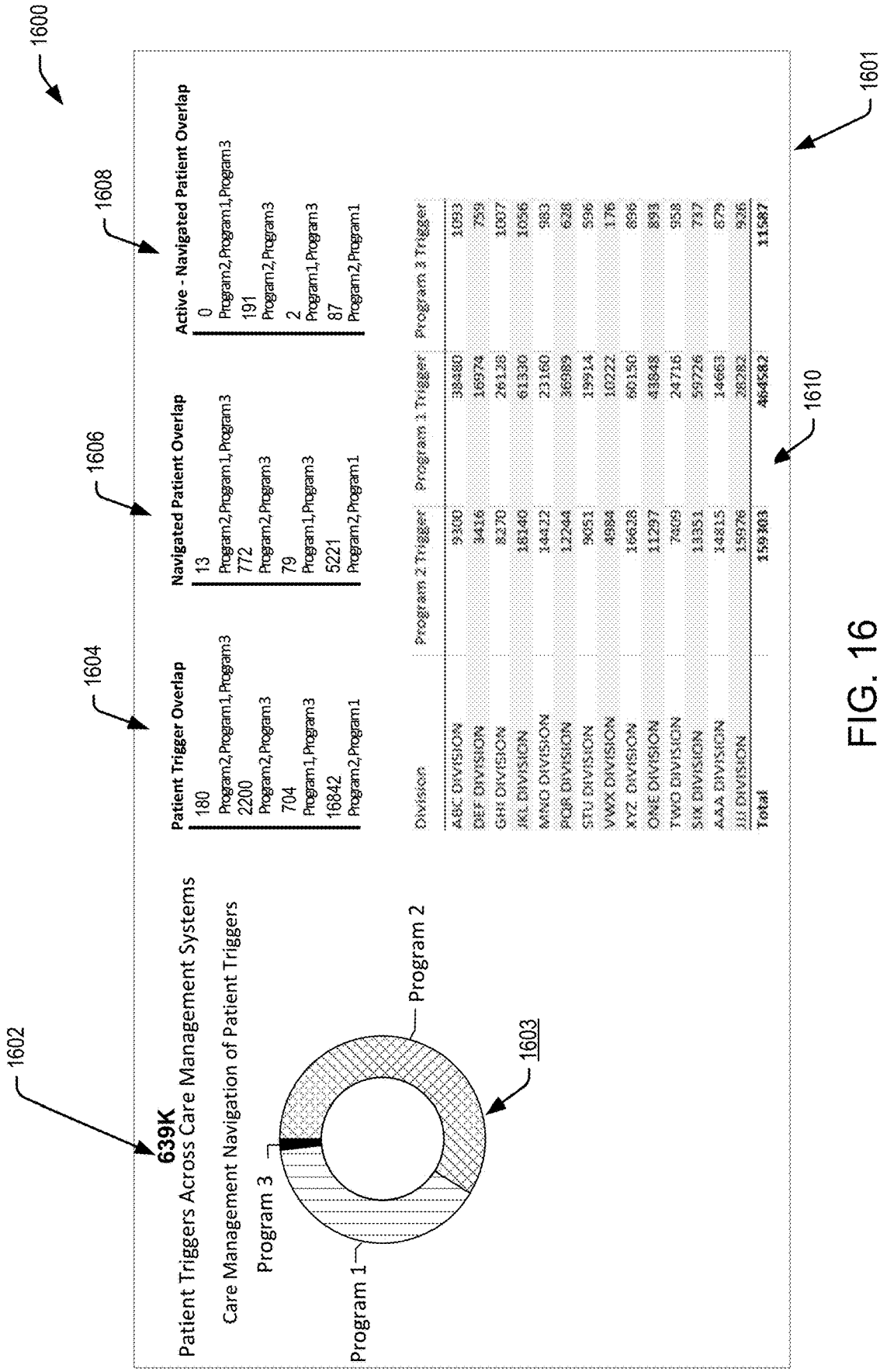
FIG. 16 illustrates another example GUI utilizable for coordinating user service among multiple users within a service organization, according to at least one example.

FIG. 16 illustrates a GUI of a display 1600 of a user device, according to at least one example. The user device may be similar to device 1336 or 1338 of FIG. 13, and may be associated with a USP (e.g., a user navigation coordinator, a service facility executive, administrator, etc.). Also, the GUI 1601 may be similar to GUI 1502 of FIG. 15, and may correspond to a dashboard presentation of an application executing on the user device. In some examples, the GUI 1601 and GUI 1502 may correspond to different views of the same application. In this illustration, the application may allow the USP to view characteristics of users triggered across multiple user navigation programs, as well as users who are assigned to more than one user navigation program. Similar to GUI 1502, these characteristics may assist a USP in coordinating user service across one or more user navigation programs to facilitate successful user journey outcomes.

Turning to GUI 1601 in further detail, the GUI 1601 depicts a top-level statistical data 1602 corresponding to a total number trigger occurrences (e.g., 639,000) for users in the service organization. GUI 1601 further depicts a pie chart 1603 showing a graphical illustration of relative proportions of users which are assigned to one of three user navigation programs. As depicted in FIG. 16, "Program 3" corresponds to one of several breast cancer navigation programs (e.g., breast cancer, lung cancer, etc.), "Program 1" corresponds to a program for users recently discharged from the emergency department (ED) and referred for follow up service, and the "Program 2" corresponds to a program for users who have cardiovascular-condition related triggers (e.g., cardiac toxicity). It should be understood that, although only three top level navigation programs are depicted in FIG. 16, any suitable number of navigation programs may be represented in examples of the present disclosure.

The GUI 1601 further presents three different types of overlap statistics. First, user trigger overlap 1604 corresponds to a number of users for which a trigger has occurred for two or more user navigation programs. For example, as depicted, 180 users have triggered for all three of Program 2, Program 1, and Program 3, while 2200 users have triggered for both Program 2 and Program 3. Similarly 704 users have triggered for both Program 1 and Program 3, and 16,842 users have triggered for both Program 1 and Program 2. A USP may use this data, for example, to determine opportunities for integrating multiple programs together. For example, as discussed with reference to FIG. 14, this overlap data may indicate a relatively larger of users (e.g., 2200) who have both cancer and cardiovascular-related triggers. The system may then receive input by a user device of the USP to suppress one of the triggers (e.g., the cardiac toxicity trigger) under certain conditions, and instead coordinate the user navigation through the Program 3 navigator. A similar analysis may be applied based on a relatively larger number of users (e.g., 16,842) that have been recently released from the ED and referred for follow-up service as well as having triggered for cardiovascular-related conditions.

Second, a navigated user overlap 1606 corresponds to a number of users who have been concurrently enrolled at some point (e.g., within a specified time range) in more than one user navigation program. For example, as depicted, 13 users have been enrolled in all three of Program 2, Program 1, and Program 3, while 772 users have been enrolled in both Program 2 and Program 3. Similarly 79 users have been enrolled in both Program 1 and Program 3, while 5221 users have been enrolled in both Program 2 and Program 1. In some examples, this data may further assist a USP in coordinating user service, for example, in helping to determine scenarios where a higher level of collaboration between navigators is useful. It should be understood that, as described herein (e.g., with reference to FIG. 18, discussed below), the system may achieve improvements in user service coordination even when a user may be assigned to more than one navigation program.

Third, an active-navigated user overlap 1608 corresponds to a number of users who are actively engaged in more than one user navigation program. Active engagement may correspond to any suitable type of interaction with a user navigator (e.g., responding to messages, participating in a service plan, etc.). In this example, 0 users are actively enrolled in all three programs, 191 users are actively enrolled in Program 2 and Program 3, 2 users are actively enrolled in Program 1 and Program 3, and 87 users are actively enrolled in Program 2 and Program 1. In some example, a USP may use this information to determine retention rates of users enrolled in navigation programs.

GUI 1610 further depicts a breakdown of a number of users who trigger for each navigation program described above (e.g., Program 2, Program 1, Program 3) on a per-division basis. It should be understood that, similar to FIG. 15, the application may allow the USP to see distributions of users according to one or more variables (e.g., applied filters). In some examples, the applied filters may enable a USP to view one or more levels of the organizational hierarchy within the enterprise (e.g., according to division, market, and/or facility).

FIG. 17 illustrates an example flow diagram illustrating a process 1700 for a UN system providing user assessment data to a dashboard for coordinating assignments of users to user navigation programs, according to some examples of the present disclosure. In some examples, the UN system that performs the process 1700 (or other processes as described in FIGS. 18-20, variations, and/or combinations thereof) may be similar to any one or more of the UN systems described herein (e.g., UN system 1211 and/or UN system 1308).

The process 1700 may start at block 1702 whereby the UN system may receive user data associated with a user record of a user. The user record may be one of a plurality of user records of users maintained by a service management system of a service organization. In some examples, the user may be associated with (e.g., admitted to) a service facility, whereby the service facility may be one of a plurality of service facilities affiliated with the service organization. In some examples, the user data may be similar to as described with reference to block 1202 of FIG. 12. In some examples, a plurality of user data may be received, respectively, for each of the plurality of users affiliated with the service organization. In some examples, the user data may be received in substantially real-time (e.g., a streaming data).

At block 1704, the UN system may determine an assessment corresponding to at least one of: (1) a segment of a plurality of segments in which the user is classified, or (2) at least one user navigation program for which the user qualifies or is already assigned. In some examples, the classified segment may be associated with an occurrence of a trigger. In some examples, this block may be similar to as described with reference to block 1204 and/or block 1206 of FIG. 12. For example, a segmentation model of the UN system may determine one or more segments in which to classify the user. Then, the UN system may detect an occurrence of one or more triggers based at least in part on the one or more classified segments. In addition to an assessment including an indication of whether the UN system has detected an occurrence of one or more triggers, the assessment may also include an indication of one or more navigation programs which may be associated with the user. For example, the UN system may determine that the user has already been enrolled (e.g., assigned to) one or more user navigation programs. The UN system may also determine, for example, based in part on the detection of one or more triggers, that the user qualifies to be assigned to one or more navigation programs. It should be understood that an assessment may include any information suitable for coordinating user service (e.g., related to user navigation). For example, an assessment may include information associated with whether the user continues to be actively engaged with currently assigned user navigation programs. The assessment may also include demographic information about the user, health record information, etc. It should be understood that, in some examples, the UN system may determine a plurality of assessments that respectively correspond to each of the plurality of user data received for the plurality of users.

At block 1706, the UN system may provide the assessment to a user device of a USP (e.g., a user navigation coordinator) for subsequent presentation on a dashboard of the user device. As described above, the assessment may be one of a plurality of assessments respectively determined for each of the plurality of users and provided to the user device for presentation. In some examples, the dashboard may be presented via a GUI (e.g., GUI 1502 of FIG. 15 or GUI 1601 of FIG. 16). As described herein, the dashboard may be operable for use in coordinating user service. For example, the dashboard may be used to coordinate assignments of users to one or more user navigation programs. The dashboard may also be used to identify ways to improve user navigation (e.g., managing segmentation models, trigger mechanisms, prioritization of users, continued engagement with users who are already assigned to a navigation program, etc.).

FIG. 18 illustrates an example flow diagram illustrating a process 1800 for a UN system updating a user interface of a user device of a USP (e.g., a user navigator), according to some examples of the present disclosure. It should be understood that this example contrasts with the primary example depicted in FIG. 14. For example, in FIG. 14, the user may be already assigned to the cancer navigation program, and then may subsequently trigger for a cardiac toxicity navigation program. The UN system 1415 of FIG. 14 may then suppress the subsequent trigger and determine that the user should not be additionally assigned to the cardiac toxicity navigation program (e.g., instead, routing cardiac toxicity navigation-related messages to the existing cancer navigation program coordinator). Instead, in the example process of FIG. 18, because the user may already be assigned to more than one navigation program (e.g., for conditions that are substantially unrelated), the UN system may facilitate coordination between user navigators to avoid messaging collisions (e.g., duplication, redundancy, etc.).

The process 1800 may start at block 1802 whereby the UN system may receive an indication that a user of a service facility is assigned to a first user navigation program and a second user navigation program of a plurality of user navigation programs. In an example, the first user navigation program may correspond to a cancer navigation program (e.g., for breast cancer), and the second user navigation program may correspond to a cardiovascular user navigation program. In this example, the user have been originally assigned to these programs for separate conditions (e.g., early breast cancer and heart disease).

At block 1804, the UN system may transmit a first message to a first user device of a first user navigator of the first user navigation program. In some examples, the first message may be associated with a first aspect of a first journey of the user through the first navigation program. Continuing with the example above, the UN system may determine the first aspect to correspond to an upcoming chemotherapy appointment and follow-up consultations with a USP (e.g., to obtain a radiology and/or pathology report). These appointments are associated with the user's cancer journey, which the cancer navigator may help the user to navigate. The UN system may transmit the first message including one or more instructions (e.g., reminders) to the cancer navigator for use in assisting the user.

At block 1806, the UN system may receive a feedback message, which may include updated user data associated with an updated condition or an updated service status of the user. Continuing with the example above, upon the user completing the chemotherapy appointment and follow-up consultations, the UN system may receive updated user data of the user. For example, the first user device of the cancer navigator may receive input from the cancer navigator regarding the completion of a task, updated user information (e.g., blood labs, radiology report, pathology report), etc. In another example, the UN system may receive the updated user data automatically from one or more other devices. For example, if the user completes more blood labs, a device (e.g., blood lab equipment) may process the blood lab and automatically transmit a blood lab report to the service management system (e.g., an EMR of the system). The UN system may receive (e.g., retrieve) the blood lab report from a storage associated with the service management system and then analyze the report.

At block 1808, the UN system may generate a second message based at least in part on the received feedback message. The second message may correspond to a second aspect of a second journey of the user through the second user navigation program. Continuing with the example above, following the reception of the feedback message at block 1806, the UN system may analyze the updated user data to detect an occurrence of one or more triggers. In some examples, this analysis and detection may be similar to blocks 1204 and/or 1206 of FIG. 12. In one example, the UN system may detect the occurrence of a trigger related to an increased level of cardiovascular toxicity. This particular trigger may correspond to the second aspect of the user's journey through the second (e.g., cardiac toxicity) user navigation program. Accordingly, the system may generate the second message, which may correspond to an instruction to assist the user in scheduling an appointment with a recommended cardiologist.

At block 1810, the UN system may transmit the second message to a second user device of a second user navigator of the second user navigation program for presentation on the second user device. Continuing with the example above, the UN system may transmit the second message corresponding to an instruction to the cardiac toxicity navigator to assist the user (e.g., with scheduling an appointment). It should be understood that the instruction may be presented on the second user device in any suitable fashion. For example, the instruction may be presented within a navigation support area (e.g., navigation support area 1412) that is curated for the specific (e.g., second) user navigator. In this case, the GUI of the second user device may display instructions only relevant for the second user navigation program. The UN system may thus coordinate messages (e.g. instructions) sent to different devices of user navigators to enable a unified messaging process. It should further be understood that the end-to-end process (e.g., blocks 1802-through blocks 1808) may be performed in substantially real-time. For example, messages transmitted to/from the UN system and other devices (e.g., user navigator devices, or other USP devices) may be processed in real-time to reduce the risk of message collisions among user navigators and users.

Figure 19:
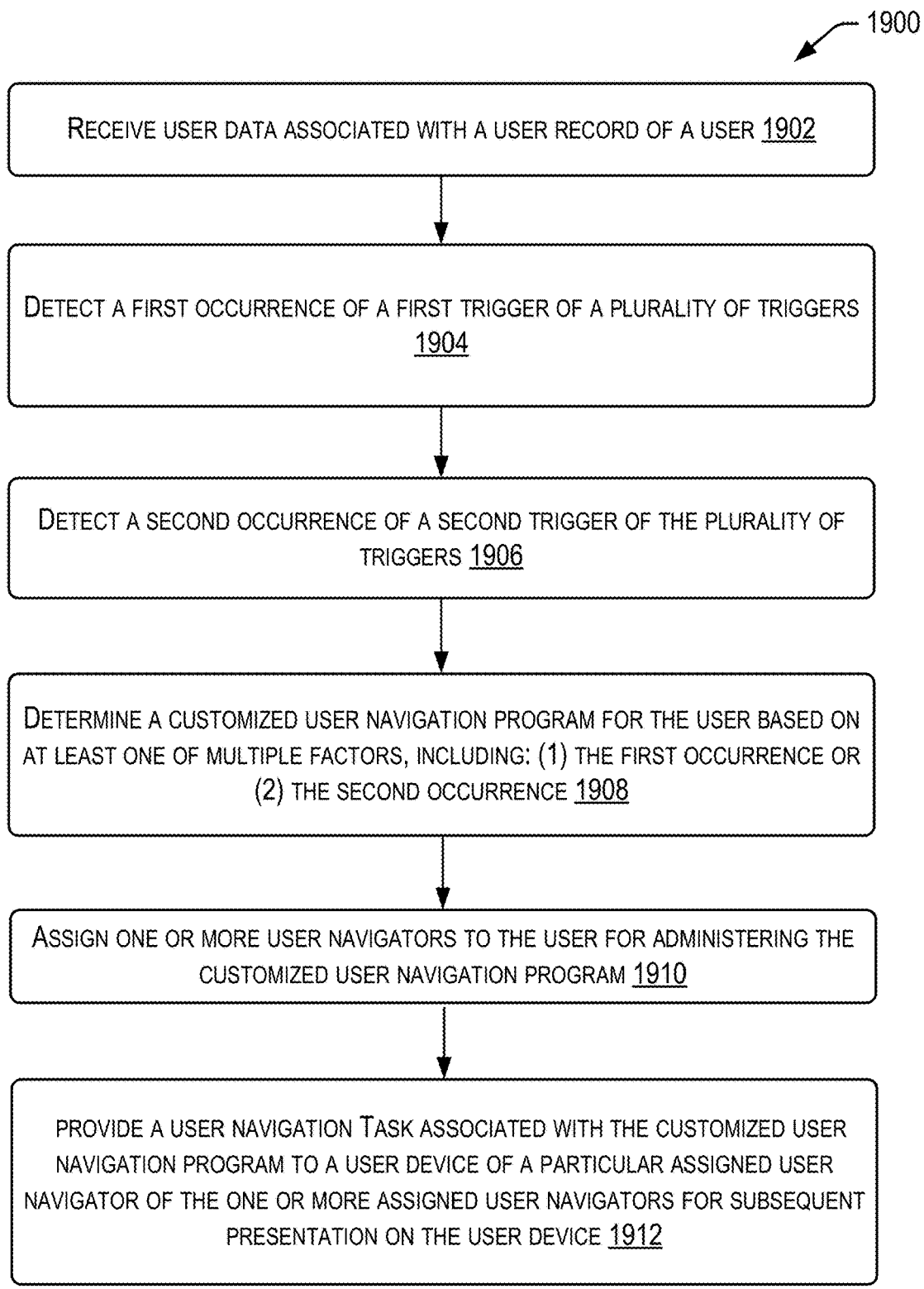
FIG. 19 illustrates an example process for providing a user navigation recommendation to a user interface of a user device of a user service provider, according to at least one example.

FIG. 19 illustrates an example flow diagram illustrating a process 1900 for a UN system presenting a user navigation recommendation to a user interface of a user device of a USP (e.g., a user navigator), according to some examples of the present disclosure. In some examples, the UN system may generate a customized user navigation program for a user, based at least in part on the detection of an occurrence of one or more triggers. The customized user navigation program may assign one or more user navigators to the user on at least one of multiple factors. The UN system may further coordinate messaging between respective user navigators and the user to reduce risk of message collisions.

The process 1900 may start at block 1902 whereby the UN system may receive user data associated with a user record of a user. In some examples, this block may be similar to block 1202 of FIG. 12.

At block 1904, the UN system may detect a first occurrence of a first trigger of a plurality of triggers. In some examples, this block may be similar to blocks 1204 and/or 1206 of FIG. 12. The first trigger may be associated with a first priority of a first segment, whereby the user may be classified within the first segment. In some examples, the first priority of the first segment may be determined by one more factors, including, for example, business rules, a severity of a condition associated with the segment, a demographic of the user, a complexity of the user's condition, etc.

At block 1906, the UN system may detect a second occurrence of a second trigger of the plurality of triggers. The second trigger may be associated with a second priority of a second segment, whereby the user may be classified within the second segment. In some examples, this block may also be similar to blocks 1904. In some examples, the second trigger may be different than the first trigger.

At block 1908, the UN system may determine a customized user navigation program for the user based on at least one of multiple factors, including: (1) the first trigger occurrence or (2) the second trigger occurrence. For example, the UN system may determine a set of recommended tasks that are included within the user navigation program to be performed by one or more USP's (e.g., user navigators). In one example, the system may determine, based at least in part on the user's history of missed appointments, that it would be beneficial to frequently remind the user of upcoming appointments. In some examples, the UN system may determine to schedule appointments on the user's behalf, and/or take extra steps to assist the user in making their appointments. In another example, the system may determine that the first trigger corresponds to a severe condition with a high level of complexity (e.g., brain cancer), while the second trigger may be associated with a metastatic condition that is of less severity. Accordingly, the tasks associated with each trigger may respectively be associated with varying levels of complexity.

At block 1910, the UN system may assign one or more user navigators to the user for administering the customized user navigation program. In some examples, the assignments may be chosen based on at least one of (1) at least one of the multiple factors associated with the first trigger occurrence or the second trigger occurrence, (2) a respective specialty of the one or more user navigators, or (3) a level of complexity the one or more user navigators are trained to handle. The level of complexity may be associated with a condition or a service status of the user. Continuing with the example above from block 1908, the UN system may assign a first user navigator to the user for assisting the user in navigating their journey with respect to the severe condition associated with the first trigger. In this example, the first user navigator may be determined based at least in part on having a high level of expertise in handling the more severe condition. Meanwhile, the UN system may assign a second user navigator to the user for assisting the user in navigating their journey with respect to the less severe metastatic condition.

At block 1912, the UN system may provide a user navigation task associated with the customized user navigation program to a user device of a particular assigned user navigator of the one or more assigned user navigators for subsequent presentation on the user device. Continuing with the above example, the user navigation task may be curated for the particular assigned user navigator. For example, the task may have a level of complexity which the particular assigned user navigator is qualified to handle (e.g., in terms of both specialty and level of training). In one example, the task may involve coordinating with other USPs to determine an appropriate service procedure for the user. In another example, the task may involve explaining to the user a more complex detail regarding their payment options. It should be understood that, similar to other examples, the UN system may track the status and performance of each task performed across the one or more user navigators to enable a higher qualify of experience for the user within the customized navigation program.

Figure 20:
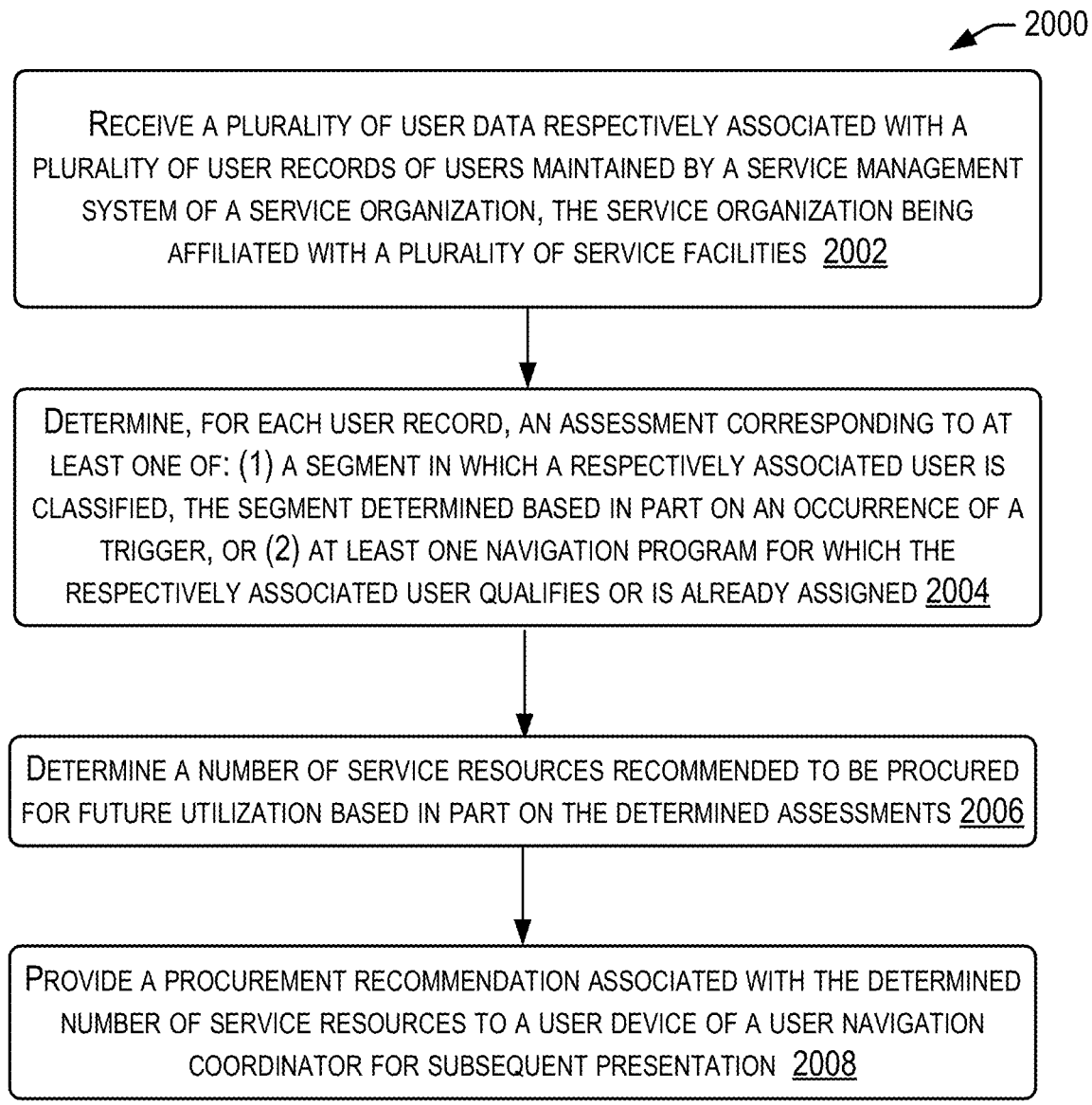
FIG. 20 illustrates an example process for a user navigation system procuring servicing resources based on a trigger occurrence, according to at least one example.

FIG. 20 illustrates an example flow diagram illustrating a process 2000 for a UN system procuring service resources based at least in part on a trigger occurrence, according to some examples of the present disclosure. In some examples, the UN system may forecast future demand for service resources (e.g., service equipment, medication, human resources, etc.) based at least in part on analyzing trigger occurrences (including user assignments to navigation programs) over a plurality of users of the service organization. In this way, the UN system may be able to increase the level of user service quality by meeting anticipated demand.

The process 2000 may start at block 2002 whereby the UN system may receive a plurality of user data respectively associated with a plurality of user records of users maintained by a service management system of a service organization. In some examples, the service organization may be affiliated with a plurality of service facilities. In some examples, this block may be similar to block 1202 of FIG. 12.

At block 2004, the UN system may determine, for each user record, an assessment for the respective user. Each assessment may correspond to at least one of: (1) a segment of a plurality of segments in which the user is classified, or (2) at least one user navigation program for which the user qualifies or is already assigned. In some examples, the classified segment may be associated with an occurrence of a trigger. In some examples, this block may be similar to block 1704 of FIG. 17.

At block 2006, the UN system may determine a number of service resources recommended to be procured for future utilization based in part on the determined assessments. In some examples, service resources may correspond to any type of resource utilizing for user service. For example, the UN system may determine a number of service equipment (e.g., self-service kits suitable for home use as part of a navigation program) that should be procured based on the plurality of assessments. In another example the UN system may determine a number of predicted users who qualify for being assigned to a particular type of user navigator (e.g., who is trained to handle cases of high complexity and/or trained in particular specialty area). The UN system may generate a procurement recommendation that incorporates this predicted number of service resources.

At block 2008, the UN system may provide the procurement recommendation associated with the determined number of service resources to a user device of a user navigation coordinator for subsequent presentation. In some examples, this block may be similar to block 1706 of FIG. 17. For example, the procurement recommendation may be presented within a GUI view of a dashboard of the user device.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method, comprising:
   receiving, by a user navigation system, user data associated with a user record of a user of a service facility, the user record being one of a plurality of user records of users maintained by a service management system of a service organization, the service facility being one of a plurality of service facilities affiliated with the service organization;
   inputting, by the user navigation system, the user data into a segmentation model of the user navigation system, the user data including at least one of structured user data or unstructured user data, and the user data associated with at least one of a present condition or a present service status of the user, the structured user data comprising at least one of a user service record, a test result, and chart information, the unstructured user data being at least one of a clinician's notes, a service image, user feedback, and user correspondence;
   determining, by the segmentation model, a score for the user, the score corresponding to a level of confidence that a classification of the user corresponds to a segment associated with the present condition or the present service status of the user, the segment being one of a plurality of candidate segments and the segmentation model being trained based at least in part on features derived from the plurality of user records of users maintained by the service management system;
   classifying, by the user navigation system and using the score, the user within the segment in accordance with a classification threshold, the classification threshold associated with a level of confidence of the score;
   detecting, by the user navigation system, an occurrence of a trigger of a plurality of triggers based at least in part on the classification of the user within the segment;
   determining, by the user navigation system, a priority of the user among the users for which user records are maintained by the service management system based at least in part on the occurrence of the trigger, the priority corresponding to a particular user navigation program among a plurality of user navigation programs;
   determining, by the user navigation system and based on the priority, a position of the user in a queue of users who are candidates for being assigned to the particular navigation program; and
   assigning, by the user navigation system, the user to the particular user navigation program among the plurality of user navigation programs based at least in part on the determined priority of the user and the position of the user in the queue.

2. The computer-implemented method of claim 1, wherein the structured user data includes a portion of the user record and is formatted in accordance with a particular database format, wherein at least a portion of the unstructured user data is not associated with a pre-defined format, and wherein the portion of the unstructured user data includes at least one of (I) notes of a user service provider, (II) an image, or (III) a video.

3. The computer-implemented method of claim 1, wherein the segmentation model includes (I) a first segmentation model associated with classifying the user according to a first candidate segment of the plurality of candidate segments, and (II) a second segmentation model associated with classifying the user according to a second candidate segment of the plurality of candidate segments, wherein the second candidate segment is a narrower segment from the first candidate segment.

4. The computer-implemented method of claim 3, further comprising:
   receiving, by the user navigation system, first training data samples corresponding to a first subset of the plurality of user records of users of the service organization, the first training data samples being associated with the first candidate segment;
   training, by the user navigation system, the first segmentation model utilizing the first training data samples;
   receiving, by the user navigation system, second training data samples corresponding to a second subset of the plurality of user records of users of the service organization, the second training data samples being associated with the narrower second candidate segment; and
   training, by the user navigation system, the second segmentation model utilizing the second training data samples.

5. The computer-implemented method of claim 3, further comprising:
   determining, by the first segmentation model, a first score associated with the first candidate segment;
   classifying, by the user navigation system, the user within the first candidate segment based at least in part on the first score being in accordance with a first classification threshold;
   executing, by the user navigation system, the second segmentation model based at least in part on the classification of the user within the first candidate segment;
   determining, by the second segmentation model, a second score associated with the second candidate segment, the second score corresponding to the score; and
   classifying, by the user navigation system, the user within the second candidate segment based at least in part on the second score being in accordance with a second classification threshold that corresponds to the classification threshold, the second candidate segment corresponding to the segment.

6. The computer-implemented method of claim 1, wherein the unstructured data comprises user service records, test results, or chart information and the structured data comprises clinician notes, service images, or user correspondence.

7. The computer-implemented method of claim 1, wherein the particular user navigation program is associated with a user navigator and the user receiving a particular course of service associated with the present condition or the present service status of the user, wherein one or more user navigation tasks of the particular course of service are performed by the user navigator.

8. The computer-implemented method of claim 1, further comprising:
receiving, by the user navigation system, a training sample that includes the score, training data associated with the user, and a training label corresponding to a ground truth classification of the user, the training sample being one of a plurality of new training samples and included within the plurality of new training samples based at least in part on a determined accuracy of the classification of the user;
updating, by the user navigation system, the segmentation model using the plurality of new training samples within a re-training process to generate an updated segmentation model;
receiving, by the user navigation system, second user data associated with a new user record of a new user; and
determining, by the updated segmentation model, a new score for the new user.

9. A user navigation system, comprising:
a memory configured to store computer-executable instructions; and
a processor configured to access the memory and execute the computer-executable instructions to at least:
receive user data associated with a user record of a user of a service facility, the user record being one of a plurality of user records of users maintained by a service management system of a service organization, the service facility being one of a plurality of service facilities affiliated with the service organization;
input the user data into a segmentation model of the user navigation system, the user data including at least one of structured user data or unstructured user data, and the user data associated with at least one of a present condition or a present service status of the user, the structured user data comprising at least one of a user service record, a test result, and chart information, the unstructured user data being at least one of a clinician's notes, a service image, user feedback, and user correspondence;
determine, by the segmentation model, a score for the user, the score corresponding to a level of confidence that a classification of the user corresponds to a segment associated with the present condition or the present service status of the user, the segment being one of a plurality of candidate segments and the segmentation model being trained based at least in part on features derived from the plurality of user records of users maintained by the service management system;
classify, using the score, the user within the segment in accordance with a classification threshold, the classification threshold associated with a level of confidence of the score;
detect an occurrence of a trigger of a plurality of triggers based at least in part on the classification of the user within the segment;
determine a priority of the user among the users for which user records are maintained by the service management system based at least in part on the occurrence of the trigger, the priority corresponding to a particular user navigation program among a plurality of user navigation programs;
determine, based on the priority, a position of the user in a queue of users who are candidates for being assigned to the particular navigation program; and
assign the user to the particular user navigation program among the plurality of user navigation programs based at least in part on the determined priority of the user and the position of the user in the queue.

10. The user navigation system of claim 9, wherein the processor is further configured to access the memory and execute additional instructions to at least:
receive updated user data associated with an updated condition or an updated service status of the user;
detect an occurrence of a second trigger of the plurality of triggers, the second trigger associated with a second priority of a second segment, the user being additionally classified within the second segment, the second segment associated with a second navigation program;
determine that the second trigger should be suppressed based on at least one of: (I) the priority exceeding the second priority or (II) an indication that the user is already assigned to the particular user navigation program; and
route messages that would otherwise be directed to a second user navigator of a second user navigation program instead to a first user navigator associated with the particular user navigation program to which the user is already assigned.

11. The user navigation system of claim 9, wherein the processor is further configured to access the memory and execute additional instructions to at least:
provide an assessment to a user device of a user navigation coordinator of the particular user navigation program for subsequent presentation on a dashboard of the user device, the assessment indicating at least one of: (I) the segment of a plurality of candidate segments in which the user is classified, or (II) at least one user navigation program for which the user qualifies or is already assigned.

12. The user navigation system of claim 11, wherein the assessment is one of a plurality of assessments respectively determined for each of a plurality of users of the service organization and provided to the user device for presentation, the dashboard operable for use in coordinating assignment of the plurality of user to one or more user navigation programs.

13. The user navigation system of claim 9, wherein the particular user navigation program is a first user navigation program, the user being assigned to the first user navigation program and a second user navigation program of the plurality of user navigation programs, and wherein the processor is further configured to access the memory and execute additional instructions to at least:

transmit a first message to a first user device of a first user navigator of the first user navigation program, the first message associated with a first aspect of a first journey of the user through the first user navigation program; and receive a feedback message including feedback data resulting from the first message, the feedback data including updated user data associated with an updated condition or an updated treatment status of the user.

14. The user navigation system of claim 13, wherein the processor is further configured to access the memory and execute additional instructions to at least:

generate a second message corresponding to a second aspect of a second journey of the user through the second user navigation program, the second message generated based at least in part on the received feedback message; and transmit the second message to a second user device of a second user navigator of the second user navigation program for presentation on the second user device.

15. The user navigation system of claim 9, wherein the processor is further configured to access the memory and execute additional instructions to at least:

assign the user to a particular user navigator of the particular user navigation program based at least in part on at least one of (I) an occurrence of one or more triggers of the plurality of triggers, (II) a respective specialty of the particular user navigator, or (III) a level of complexity the particular user navigator is trained to handle, the level of complexity associated with the present condition or the present service status of the user.

16. The user navigation system of claim 9, wherein the processor is further configured to access the memory and execute additional instructions to at least:

provide a user navigation task associated with the particular user navigation program to a user device of a particular assigned user navigator of one or more assigned user navigators for subsequent presentation on the user device, the user navigation task curated for the particular assigned user navigator.

17. One or more non-transitory computer-readable storage devices comprising computer-executable instructions that, when executed by one or more computer systems, cause the one or more computer systems to perform operations, comprising:

receiving user data associated with a user record of a user of a service facility, the user record being one of a plurality of user records of users maintained by a service management system of a service organization, the service facility being one of a plurality of service facilities affiliated with the service organization;

inputting the user data into a segmentation model of the one or more computer systems, the user data including at least one of structured user data or unstructured user data, and the user data associated with at least one of a present condition or a present service status of the user, the structured user data comprising at least one of a user service record, a test result, and chart information, the unstructured user data being at least one of a clinician's notes, a service image, user feedback, and user correspondence;

determining, by the segmentation model, a score for the user, the score corresponding to a level of confidence that a classification of the user corresponds to a segment associated with the present condition or the present service status of the user, the segment being one of a plurality of candidate segments and the segmentation model being trained based at least in part on features derived from the plurality of user records of users maintained by the service management system;

classifying, using the score, the user within the segment in accordance with a classification threshold, the classification threshold associated with a level of confidence of the score;

detecting an occurrence of a trigger of a plurality of triggers based at least in part on the classification of the user within the segment;

determining a priority of the user among the users for which user records are maintained by the service management system based at least in part on the occurrence of the trigger, the priority corresponding to a particular user navigation program among a plurality of user navigation programs;

determining, based on the priority, a position of the user in a queue of users who are candidates for being assigned to the particular navigation program; and assigning the user to the particular user navigation program among the plurality of user navigation programs based at least in part on the determined priority of the user and the position of the user in the queue.

18. The one or more non-transitory computer-readable storage devices of claim 17, further comprising additional instructions that, when executed by the one or more computer systems, cause the one or more computer systems to perform additional operations comprising:

determining a number of medical resources recommended to be procured for future utilization based at least in part on assigning the user to the particular user navigation program, the medical resources including at least one of: (I) medical equipment, (II) a user navigator, or (III) a type of medication or treatment.

19. The one or more non-transitory computer-readable storage devices of claim 17, further comprising additional instructions that, when executed by the one or more computer systems, cause the one or more computer systems to perform additional operations comprising:

receiving first training data samples corresponding to a first subset of the plurality of user records of users of the service organization, the first training data samples being associated with a first candidate segment;

training a first segmentation model utilizing the first training data samples;

receiving second training data samples corresponding to a second subset of the plurality of user records of users of the service organization, the second training data samples being associated with a narrower second candidate segment than the first candidate segment; and training a second segmentation model utilizing the second training data samples.

20. The one or more non-transitory computer-readable storage devices of claim 17, further comprising additional instructions that, when executed by the one or more computer systems, cause the one or more computer systems to perform additional operations comprising:

receiving updated user data associated with an updated condition or an updated service status of the user;

detecting an occurrence of a second trigger of the plurality of triggers, the second trigger associated with a second priority of a second segment, the user being additionally classified within the second segment, the second segment associated with a second navigation program;

determining that the second trigger should be suppressed based on at least one of: (I) the priority exceeding the second priority or (II) an indication that the user is already assigned to the particular user navigation program; and routing messages that would otherwise be directed to a second user navigator of a second user navigation program instead to a first user navigator associated with the particular user navigation program to which the user is already assigned.

* * * * *